US006858707B1

(12) United States Patent
Wei et al.

(10) Patent No.: US 6,858,707 B1
(45) Date of Patent: Feb. 22, 2005

(54) HYPERSENSITIVE RESPONSE ELICITOR FRAGMENTS WHICH ARE ACTIVE BUT DO NOT ELICIT A HYPERSENSITIVE RESPONSE

(75) Inventors: Zhong-Min Wei, Kirkland, WA (US); Hao Fan, Bothell, WA (US); Jennifer J. Stephens, Redwood City, CA (US); Steven V. Beer, Ithaca, NY (US); Ron J. Laby, Houston, TX (US)

(73) Assignees: EDEN Bioscience Corporation, Bothell, WA (US); Cornell Research Foundation, Inc., Ithaca, NY (US)

( * ) Notice: Subject to any disclaimer, the term of this patent is extended or adjusted under 35 U.S.C. 154(b) by 67 days.

(21) Appl. No.: 09/412,100

(22) Filed: Oct. 4, 1999

Related U.S. Application Data

(60) Provisional application No. 60/103,050, filed on Oct. 5, 1998.

(51) Int. Cl.[7] .................................................. C07K 1/00

(52) U.S. Cl. ....................... 530/350; 530/300; 800/288; 800/298; 800/305; 800/312; 800/301; 800/200; 435/7.1; 435/410; 435/847; 514/2; 514/12; 424/93

(58) Field of Search ................................ 514/2, 12, 21; 530/350, 300; 424/93; 435/7.1, 410, 847; 800/288, 298, 305, 312, 301, 200

(56) References Cited

U.S. PATENT DOCUMENTS

| | | | | | |
|---|---|---|---|---|---|
| 4,569,841 | A | | 2/1986 | Liu | 424/93 |
| 4,597,972 | A | | 7/1986 | Taylor | 426/36 |
| 4,601,842 | A | | 7/1986 | Caple et al. | 252/70 |
| 4,740,593 | A | | 4/1988 | Gonzalez et al. | 435/243 |
| 4,851,223 | A | | 7/1989 | Sampson | 424/711 |
| 4,886,825 | A | | 12/1989 | Ruess et al. | 514/383 |
| 4,931,581 | A | | 6/1990 | Schurter et al. | 560/18 |
| 5,057,422 | A | | 10/1991 | Bol et al. | 435/240 |
| 5,061,490 | A | | 10/1991 | Paau et al. | 424/93 |
| 5,135,910 | A | | 8/1992 | Blackburn et al. | 514/2 |
| 5,173,403 | A | | 12/1992 | Tang | 435/6 |
| 5,217,950 | A | | 6/1993 | Blackburn et al. | 514/2 |
| 5,243,038 | A | | 9/1993 | Ferrari et al. | 536/23.1 |
| 5,244,658 | A | | 9/1993 | Parke | 509/117 |
| 5,260,271 | A | | 11/1993 | Blackburn et al. | 514/7 |
| 5,348,743 | A | | 9/1994 | Ryals et al. | 424/94.61 |
| 5,494,684 | A | | 2/1996 | Cohen | 424/523 |
| 5,523,311 | A | | 6/1996 | Schurter et al. | 548/361 |
| 5,550,228 | A | | 8/1996 | Godiard et al. | 536/24.1 |
| 5,552,527 | A | | 9/1996 | Godiard et al. | 530/379 |
| 5,708,139 | A | | 1/1998 | Collmer et al. | 530/350 |
| 5,850,015 | A | | 12/1998 | Bauer et al. | 800/205 |
| 5,859,324 | A | * | 1/1999 | Wei et al. | 800/200 |
| 5,977,060 | A | * | 11/1999 | Zitter et al. | 514/2 |
| 6,001,959 | A | | 12/1999 | Bauer et al. | 530/300 |
| 6,235,974 | B1 | * | 5/2001 | Qiu et al. | 800/301 |
| 6,277,814 | B1 | * | 8/2001 | Qiu et al. | 514/2 |

FOREIGN PATENT DOCUMENTS

| | | | |
|---|---|---|---|
| EP | 0 612 848 A3 | | 2/1994 |
| WO | WO 93/23532 | | 11/1993 |
| WO | WO 94/01546 | | 1/1994 |
| WO | WO 94/26782 | | 11/1994 |
| WO | WO 95/19443 | | 7/1995 |
| WO | WO 96/39802 | * | 12/1996 |
| WO | WO 98/15547 | | 4/1998 |
| WO | WO 98/24297 | | 6/1998 |
| WO | WO 98/32844 | | 7/1998 |
| WO | WO 98/37752 | * | 9/1998 |
| WO | WO 98/54214 | | 12/1998 |
| WO | WO 99/07206 | | 2/1999 |
| WO | WO 99/07207 | | 2/1999 |

OTHER PUBLICATIONS

US 5,650,387, 7/1997, Wei et al. (withdrawn)

Honée, et al., "Molecular Characterization of the Interaction Between the Fungal Pathogen *Cladosporium fulvum* and Tomato," *Advances in Molecular Genetics of Plant–Microbe Interactions*, 3:199–206 (1994).

Keller, et al., "Responses of Tobacco to Elicitins, Proteins From *Phytophthora Spp.* Eliciting Acquired Resistance," *Advances in Molecular Genetics of Plant–Microbe Interactions*, 3:327–32 (1994).

Nürnberger et al., "High Affinity Binding of a Fungal Oligopeptide Elicitor to Parsley Plasma Membranes Triggers Multiple Defense Responses," *Cell* 78:449–460 (1994).

Wei et al., "Harpin, an HR Elicitor, Activates Both Defense and Growth Systems in Many Commercially Important Crops," *Phytopathology* 88:S96 (1998) (abstract only).

Niggemeyer et al., "Characterization of the Functional Domains of Harpin," *Phytopathology* 88:S67 (1998) (abstract only).

(List continued on next page.)

*Primary Examiner*—Christopher S. F. Low
*Assistant Examiner*—Hope A. Robinson
(74) *Attorney, Agent, or Firm*—Nixon Peabody LLP

(57) ABSTRACT

The present invention is directed to isolated active fragments of a hypersensitive response elicitor protein or polypeptide which fragment does not elicit a hypersensitive response in plants. Also disclosed are isolated DNA molecules which encode such fragments. Isolated fragments of hypersensitive response elicitor proteins or polypeptides in accordance with the present invention and the isolated DNA molecules that encode them have the following activities: imparting disease resistance to plants, enhancing plant growth, and/or controlling insects on plants. This can be achieved by applying the fragments of a hypersensitive response elicitor in a non-infectious form to plants or plant seeds under conditions effective to impart disease resistance, to enhance plant growth, and/or to control insects on plants or plants grown from the plant seeds. Alternatively, transgenic plants or plant seeds transformed with a DNA molecule encoding the fragment can be provided and the transgenic plants or plants resulting from the trasgenic plant seeds are grown under conditions effective to impart disease resistance, to enhance plant growth, and/or to control insects on plants or plants grown from the plant seeds.

23 Claims, 2 Drawing Sheets

OTHER PUBLICATIONS

Parker et al., "An Extracellular Glycoprotein from *Phytopthora megasperma* f.sp. glycinea Elicits Phytoalexin Synthesis in Cultured Parsley Cells and Protoplasts," *Mol. Plant Microbe Interact*. 4:19–27 (1991).

Hahlbrock et al., "Elicitor–Mediated Defense Gene Activation in Incompatible Plant/Fungus Interactions," *Journal of Cellular Biochemistry Supplement* 19B:144 (1995) (abstract only).

Honée et al., "Induction of Defense–Related Responses in Cf9 Tomato Cells by the AVR9 Elicitor Peptide of *Cladosporium fulvum* is Developmentally Regulated," *Plant Physiol.* 117:809–820 (1998).

Keller et al., "Changes in the Accumulation of Soluble and Cell Wall–Bound Phenolics in Elicitor–Treated Cell Suspension Cultures and Fungus–Infected Leaves of *Solanum tuberosum*," *Phytochemistry* 42(2):389–396 (1996).

Gijsegem et al., "Activation of Defense–Related Genes in Parsley Leaves by Infection with *Erwinia chrysanthemi*," *European Journal of Plant Pathology* 101:549–559 (1995).

Nürnberger et al., Fungal Peptide Elicitors: Signals Mediating Pathogen Recognition in Plants, *Journal of Biosciences* 53: 141–150 (1998).

Sacks et al., "Molecular Characterization of Nucleotide Sequences Encoding the Extracellular Glycoprotein Elicitor from *Phytophthora megasperma*," *Mol. Gen. Genet*. 246:45–55 (1995).

Daniels et al., "Plant and Baceterial Genes Involved in Interactions Between Xanthomonas and Crucifers," *Current Plant Science and Biotechnology in Agriculture* 2(14):423–433 (1993).

Daniels et al., "Interaction Between *Arabidopsis thaliana* and Xanthomonas campestris," *Current Plant Science and Biotechnology in Agriculture* 1(10):84–89 (1991).

Parker et al., "Response of Parsley Cells and Protoplasts to Fungal Elicitor," *J. Cell Biochem*. Suppl 0 (12 Part C) p. 255 (1988) (abstract only).

Collmer et al., "*Erwinia chrysanthemi* and *Pseudomonas syringae*: Plant Pathogens Trafficking in Extracellular Virulence Proteins," pp. 43–78.

Frederick et al., "The WTS Water–Soaking Genes of *Erwinia stewartii* are Related to hrp Genes," Seventh International Symposium on Molecular Plant Microbe Interactions, Abstract No. 191 (Jun. 1994).

Wei et al., "Proteinaceous Elicitors of the Hypersensitive Response from *Xanthomonas campestris* pv. *glycines*," Seventh International Symposium on Molecular Plant Microbe Interactions, Abstract No. 244 (Jun. 1994).

Preston et al., "The HrpZ Proteins of *Pseudomonas syringae* pvs. *syringae, glycinea*, and *tomato* are Encoded by an Operon Containing *Yersinia ysc* Homologs and Elicit the Hypersensitive Response in Tomato but not Soybean," *Mol. Plant–Microbe Interact.*, 8(5):717–32 (1995).

Bauer et al., "*Erwinia chrysanthemi hrp* Genes and their Involvement in Elicitation of the Hypersensitive Response in Tobacco," Sixth International Symposium on Molecular Plant Microbe Interactions, Abstract No. 146 (Jul. 1992).

Stryer, L., "Enzymes are Highly Specific," *Biochemistry*, San Francisco: W.H. Freeman and Company, p. 116 (1975).

Keen et al., "Inhibition of the Hypersensitive Reaction of Soybean Leaves to Imcompatible Pseudomonas spp. by Blasticidin S, Streptomycin or Elevated Temperature," *Physiological Plant Pathology*, 18:325–337 (1981).

Lerner, R.A., "Tapping the Immunological Repertoire to Produce Antibodies of Predetermined Specificity," *Nature*, 299:592–96 (1982).

Staskawicz et al., "Cloned Avirulence Gene of *Pseudomonas syringae* pv. *glycinea* Determines Race–specific Incompatibility on *Glycine max* (L.) Merr.," *Proc. Natl. Acad. Sci. USA*, 81:6024–28 (1984).

Bauer et al., "*Erwinia chrysanthemi* Harpin$_{Ech}$: An Elicitor of the Hypersensitive Response that Contributes to Soft–Rot Pathogenesis," *MPMI*, 8(4):484–91 (1995).

Huang et al., "Characterization of the hrp Cluster from *Pseudomonas syringae* pv. *syringae* 61 and TnphoA Tagging of Genes Encoding Exported or Membrane–Spanning Hrp Proteins," *Molec. Plant–Microbe Interact.*, 4(5):469–76 (1991).

Huang et al., "The *Pseudomonas syringae* pv. *syringae* 61 hrpH Product, an Envelope Protein Required for Elicitation of the Hypersensitive Response in Plants," *J. Bacteriol.*, 174(21):6878–85 (1992).

Bonas, U., "hrp Genes of Phytopathogenic Bacteria," *Current Topics in Mirobio.*, 192:79–98 (1994).

Arlat et al., "PopA1, A Protein Which Induces a Hypersensitivity–Like Response on Specific Protein Petunia Genotypes, is Secreted via the Hrp Pathway of *Pseudomonas solanacearum*," *The EMBO J.*, 13(3):543–53 (1994).

Kessmann et al., "Induction of Systemic Acquired Disease Resistance in Plants By Chemicals," *Ann. Rev. Phytopathol.*, 32:439–59 (1994).

Kelman, A., "The Relationship of Pathogenicity in *Pseudomonas solanacearum* To Colony Appearance on a Tetrazolium Medium," *Phytopathology*, 44:693–95 (1954).

Winstead et al., "Inoculation Techniques For Evaluating Resistance to *Pseudomonas solanacearum*," *Phytopathology*, 42:628–34 (1952).

Ahl et al., "Iron Bound–Siderophores, Cyanic Acid, and Antibiotics Involved in Suppression of *Thielaviopsis basiocola* by a *Pseudomonas fluorescens* Strain," *J. Phytopathology*, 116:121–34 (1986).

Anderson et al., "Responses of Bean to Root Colonization with *Pseudomonas putida* in a Hydroponic System," *Phytopathology*, 75(9):992–95 (1985).

Gardner et al., "Growth Promotion and Inhibition by Antibiotic–Producing Fluorescent Pseudomonads on Citrus Roots," *Plant and Soil*, 77:103–13 (1984).

Kloepper, J.W., "Effect of Seed Piece Inoculation with Plant Growth–Promoting Rhizobacteria on Populations of *Erwinia carotovora* on Potato Roots and in Daughter Tubers," *Phytopathology*, 73(2):217–19 (1983).

Atkinson et al., "The Hypersensitive Reaction of Tobacco to *Pseudomonas syringae* pv. *pisi*," *Plant Physiol.*, 79:843–47 (1985).

Huynh et al., "Bacterial Blight of Soybean: Regulation of a Pathogen Gene Determining Host Cultivar Specificity," *Science*, 245:1374–77 (1986).

Kloepper et al., "Plant Growth–Promoting Rhizobacteria on Canola (Rapeseed)," *Plant Disease*, 72(1):42–6 (1988).

Kloepper et al., "Enhanced Plant Growth by Siderophores Produced by Plant Growth–Promoting Rhizobacteria," *Nature*, 286:885–86 (1980).

Kloepper et al., "Pseudomonas Siderophores: A Mechanism Explaining Disease–Suppressive Soils," *Current Microbiology*, 4:317–20 (1980).

Kloepper et al., "Emergence–Promoting Rhizobacteria: Description and Implications for Agriculture," In: *Iron, Siderophores, and Plant Disease*, Swinborne (ed), Plenum, NY, 155–64 (1986).
Kloepper et al., "Relationship of in vitro Antibiosis of Plant Growth–Promoting Rhizobacteria to Plant Growth and the Displacement of Root Microflora," *Phytopathology*, 71(10):1020–24 (1981).
Kloepper et al., "Effects of Rhizosphere Colonization by Plant Growth–Promoting Rhizobacteria on Potato Plant Development and Yield," *Phytopathology*, 70(11):1078–82 (1980).
Kloepper et al., "Plant Growth Promotion Mediated by Rhizosphere Bacterial Colonizers," In: *The Rhizosphere and Plant Growth*,—315–32, Keister et al. (eds), pp. 315–326 (1991).
Lifshitz et al., "Growth Promotion of Canola (rapeseed) Seedlings by a Strain of *Pseudomonas putida* Under Gnotobiotic Conditions," Conditions, *Microbiol.* 33:390–95 (1987).
Liu et al, "Induction of Systemic Resistance in Cucumber Against Bacterial Angular Leaf Spot by Plant Growth–Promoting Rhizobacteria," *Phytopathology*, 85(8):843–47 (1995).
Loper et al., "Influence of Bacterial Sources of Indole–3–acetic Acid on Root Elongation of Sugar Beet," *Phytopathology*, 76(4):386–89 (1986).
Schroth et al., "Disease–Suppressive Soil and Root–Colonizing Bacteria," *Science*, 216:1376–81 (1982).
Stutz et al., "Naturally Occurring Fluorescent Pseudomonads Involved Suppression of Black Root Rot of Tobacco," *Phytopathology*, 76(2):181–85 (1986).
Lindgren et al., "Gene Cluster of *Pseudomonas syringae* pv. "*phaseolicola*" Controls Pathogenicity of Bean Plants and Hypersensitivity on Nonhost Plants," *J. Bacteriol.*, 168(2):512–22 (1986).
Bauer et al., "Cloning of a Gene from *Erwinia amylovora* Involved in Induction of Hypersensitivity and Pathogenicity," *Plant Pathogenic Bacteria*, Proceedings of the Sixth International Conference on Plant Pathogenic Bacteria, Maryland, pp. 425–429 (1987).
Wei et al., "Induction of Systemic Resistance of Cucumber to *Colletotrichum orbiculare* by Select Strains of Plant Growth–Promoting Rhizobacteria," *Phytopathology*, 81:1508–12 (1991).
Wei et al., "Induction of Systemic Resistance with Seed Treatment by PGPR Strains," pp. 191–194.
Weller, D.M., "Biological Control of Soilborne Plant Pathogens in the Rhizosphere with Bacteria," *Ann. Rev. Phytopathol.*, 26:379–407 (1988).
Young et al., "PGPR: Is There a Relationship Between Plant Growth Regulators and the Stimulation of Plant Growth or Biological Activity?," pp. 182–186.
Wei et al., "Induced Systemic Resistance by Select Plant Growth–Promoting Rhizobacteria Against Bacterial Wilt of Cucumber and the Beetle Vectors," *Phytopathology*, 86:1154, Abstract No. 313 (1995).
Wieringa–Brants et al., Induced Resistance in Hypersensitive Tobacco Against Tobacco Mosaic Virus by Injection of Intercellular Fluid from Tobacco Plants with Systemic Acquired Resistance, *Phytopathology*, 118:165–70 (1987).
Malamy et al., "Salicylic Acid: A Likely Endogenous Signal in the Resistance Response of Tobacco to Viral Infection," *Science*, 250:1002–04 (1990).
Dean et al., "Immunisation Against Disease: The Plant Fights Back," pp. 383–411.
Cameron et al., "Biologically Induced Systemic Acquired Resistance in *Arabidopsis thaliana*," *The Plant Journal*, 5(5):715–25 (1994).
Laby et al., "Structural and Functional Analysis of *Erwinia amylovora* Harpin, An Elicitor of the Plant Hypersensitive Response," *Phytopathology*, 84:345 (1994).
Van Gijsegem et al., "Conservation of Secretion Pathways for Pathogenicity Determinants of Plant and Animal Bacteria," *Trends in Microbiol.* 1(5):175–80 (1993).
Kamoun, et al., "Extracellular Protein Elicitors from Phytophthora: Host–Specificity and Induction of Resistance to Bacterial and Fungal Phytopathogens," *Molecular PlantMicrobe Interactions*, 6(1):15–25 (1993).
Baillieul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance," *The Plant Journal*, 8(4):551–60 (1995).
Collinge et al., "Plant Gene Expression in Response to Pathogens," *Plant Molecular Biology*, 9:389–410 (1987).
Shatzman et al., "Expression, Identification, and Characterization of Recombinant Gene Products in *Escherichia coli*," *Methods in Enzymology*, 152:661–73 (1987).
Tenkahen, et al., "Function of the Oxidative Burst in Hypersensitive Disease Resistance," *Proc. Natl. Acad. Sci. USA*, 92:4158–63 (1995).
Bonnett, et al., "Induction de nécroses foliaires, de protëines b et de résistance dans les interactions tabac Phytophthora," *Agronomie*, 6(9):829–37 (1986).
Gallitelli, et al., "Satellite–Mediated Protection of Tomato Against Cucumber Mosaic Virus: II. Field Test Under Natural Epidemic Conditions in Southern Italy," *Plant Disease*, 75(1):93–5 (1991).
Kang et al., "Control of Tomato Mosaic Disease by Interference of an Attenuated Virus," *Res. Rept. RDA* (*Hort.*), 27(1):17–26 (1985).
Montasser, et al., "Satellite–Mediated Protection of Tomato Against Cucumber Mosaic Virus: I. Greenhouse Experiments and Simulated Epidemic Conditions in the Field," *Plant Disease*, 75(1):86–92 (1991).
Marks, R.J., "Varietal Resistance to Potato Cyst Nematode," pp. 63–67 (1979).
Walton, et al., "Host–Selective Toxins and Disease Specificity: Perspectives and Progress", *Annu. Rev. Phytopathol.*, 31:275–303 (1993).
Atkinson, M.M., "Molecular Mechanisms of Pathogen Recognition by Plants," *Advances in Plant Pathology*, 10:36–64 (1993).
Godiard, et al., "Differential Regulation in Tobacco Cell Suspensions of Genes Involved in Plant–Bacterial Interactions by Pathogen–Related Signals," *Plant Molecular Biology*, 17:409–13 (1991).
Ricci, et al., "Structure and Activity of Proteins from Pathogenic Fungi Phytophthora Eliciting Necrosis and Acquired Resistance in Tobacco," *Eur. J. Biochem.*, 183:555–63 (1989).
Lakhmatova, I.T., "Induction of Plant Resistance to Viral Diseases: Application of Vaccination," *Sel'skokhozyaistvennaya Biologiya, Biologiya*, 3:39–51 (1991).
*Biologicheskii Zhurnal Armenii*, 31(3):305–09 (1978).

Lakhmatova, I.T., "Using Biologically Active Substances to Induced Plant Resistance to Viruses Immunization," *Sel'skokhozyaistvennaya Biologiya*, 3:13–22 (1992).
Shields, R., "Towards Insect–Resistant Plants," *Nature*, 328:12–13 (1987).
Huang et al., "Molecular Cloning of a *Pseudomonas syringae* pv. *syringae* Gene Cluster That Enables *Pseudomonas fluorescens* To Elicit the Hypersensitive Response in Tobacco Plants," *J. Bacteriol.*, 170(10:4748–56 (1988).
Ricci, et al., "Differential Production of Parasiticein, an Elicitor of Necrosis and Resistance in Tobacco, by Isolates of *Phytophthora parasitica*," *Plant Pathology*, 41:298–307 (1992).
Keen, et al., "Bacteria Expressing Avirulence Gene D Produce a Specific Elicitor of the Soybean Hypersensitive Reaction," *Molecular Plant–Microbe Interactions*, 3(2):112–21 (1990).
Bauer, et al., "*Erwinia chrysanthemi hrp* Genes and Their Involvement in Soft Rot Pathogenesis and Elicitation of the Hypersensitive Response," *MPMI*, 7(5):573–81 (1994).
Schottens–Toma et al., "Purification and Primary Structure of a Necrosis–inducing Peptide from the Apoplastic Fluids of Tomato Infected with *Cladosporium fulvum* (syn. *Fulvia fulva*)," *Physiological and Molecular Plant Pathology*, 33:59–67 (1988).
Steinberger et al., "Creation and Complementation of Pathogenicity Mutants of *Erwinia amylovora*," *Molecular Plant-Microbe Interactions*, 1(3):135–44 (1988).
Beer et al., "The Hypersensitive Response is Elicited by *Escherichia coli* Containing a Cluster of Pathogenicity Genes From *Erwinia amylovora*," *Phytopathology*, 79(10):1156 (Abstract 169) (1989).
Hiatt et al., "Production of Antibodies in Transgenic Plants," *Nature*, 342:76–8 (1989).
Hippe et al., "In Situ Localization of a Foreign Protein in Transgenic Plants by Immunoelectron Microscopy Following High Pressure Freezing. Freeze Substitution and Low Temperature Embedding," *European Journal of Cell Biology*, 50:230–34(1989).
Huang et al., "Isolation and Purification of a Factor from *Pseudomonas solanacearum* That Induces a Hypersensitive-like Response in Potato Cells," *Molecular Plant–Microbe Interactions*, 2(3):132–38 (1989).
James et al., "Genetic Transformation of Apple (*Malus pumila* Mill.) Using a Disarmed Ti–binary Vector," *Plant Cell Reports*, 7:658–61 (1989).
Laby et al., "Cloning and Preliminary Characterization of an hrp Gene Cluster of *Erwinia amylovora*," *Phytopathology*, 79(10):1211 (Abstract 607) (1989).
Dow et al., "Extracellular Proteases from *Xanthomonas campestris* pv. Campestris, the Black Rot Pathogen," *Applied and Environmental Microbiology*, 56(10):2994–98 (1990).
Walters et al., "Gene for Pathogenicity and Ability to Cause the Hypersensitive Reaction Cloned from *Erwinia amylovora*," *Physiological and Molecular Plant Pathology*, 36:509–21 (1990).
Wu et al., "Cloning, Genetic Organization, and Characterization of a Structural Gene Encoding Bacillopeptidase F from *Bacillus subtilis*," *The Journal of Biological Chemistry*, 265(12):6854–50 (1990).
Bauer et al., "Further Characterization of an hrp Gene Cluster of *Erwinia amylovora*," *Molecular Plant–Microbe Interactions*, 4(5):493–99 (1991).
Beer et al., "The hrp Gene Cluster of*Erwinia amylovora*," *Advances in Molecular Genetics of Plant–Microbe Interactions*, 1:53–60 (1991).
Benvenuto et al., "'Phytoantibodies': A General Vector for the Expression of Immunoglobulin Domains in Transgenic Plants," *Plant Molecular Biology*, 17:865–74 (1991).
Milat et al., "Physiological and Structural Changes in Tobacco Leaves Treated with Cryptogein, a Proteinaceous Elicitor From *Phytophthora cryptogea*," *Phytopathology*, 81(11):1364–68 (1991).
Ruberti et al., "A Novel Class of Plant Proteins Containing a Homeodomain with a Closely Linked Leucine Zipper Motif," *The EMBO Journal*, 10(7):1787–91 (1991).
Quigley et al., "Nucleotide Sequence and Expression of a Novel Glycine–Rich Protein Gene from *Arabidopsis thaliana*," *Plant Molecular Biology*, 17:949–52 (1991).
Van Kan et al., "Cloning and Characterization of cDNA of Avirulence Gene avr9 of the Fungal Pathogen *Cladosporium fulvum*, Causal Agent of Tomato Leaf Mold," *Molecular Plant–Microbe Interactions*, 4(1):52–9 (1991).
Waldmann, T.A. "Monoclonal Antibodies in Diagnosis and Therapy," *Science*, 252:1657–62 (1991).
Willis et al., "hrp Genes of Phytopahtogenic Bacteria," *Molecular Plant–Microbe Interactions*, 4:(2) 132–38 (1991).
Beer et al., "Are Harpins Universal Elicitors of the Hypersensitive Response of Phytopahtogenic Bacteria?," *Advances in Molecular Genetics of Plant–Microbe Interactions*, 2:281–86 (1992).
Laby et al., "Hybridization and Functional Complementation of the hrp Gene Cluster from *Erwinia amylovora* Strain Ea321 With DNA of Other Bacteria," *Molecular Plant–Microbe Interactions*, 5(5):412–19 (1992).
Sandhu, "Protein Engineering of Antibodies," *Crit. Rev. in Biotech.*, 12(5/6):437–62 (1992).
Wei et al., "Harpin, Elicitor of the Hypersensitive Response Produced by the Plant Pathogen *Erwinia amylovora*," *Science*, 257:85–8 (1992).
He et al., "*Pseudomonas syringae* pv. *syringae* $Harpin_{Pss}$: A Protein that is Secreted via the Hrp Pathway and Elicits the Hypersensitive Response in Plants," *Cell*, 73:1255–66 (1993).
Bonas, U., "Bacterial Home Goal by Harpins," *Trends in Microbiology*, 2:1–2 (1994).
Boccara, et al., "Plant Defense Elicitor Protein Produced by *Erwinia chrysanthemi*," *Mechanisms of Plant Defense Responses*, p. 166 (1993).
Qui et al., "Treatment of Tomato Seed with Harpin Enhances Germination and Growth and Induces Resistance to *Ralstonia solanacearum*," *Phytopathology*, 87:6, S80 (1997) (abstract only).
Burr et al., "Increased Potato Yields by Treatment of Seedpieces with Specific Strains of *Pseudomonas fluorescens* And *P. purida*," *Phytopathology*, 68:1377–1383 (1978).
Ricci et al., "Proteinaceous Elicitors of Plant Defense Responses," B. Fritig eds., *Mechanisms of Plant Defense Responses*, Netherlands, pp. 121–130 (1993).
Keen et al., "Syringolide Elicitors Specified By Avirulence Gene D Alleles In *Pseudomonas syringae*," *Advances in Molecular Genetics of Plant–Microbe Interactions*, 3:41–48 (1994).
Klessig et al., "The Salicylic Acid Signal In Plants," *Plant Molecular Biology*, 26:1439–1458 (1994).

Bogdanove et al., "Unified Nomenclature For Broadly Conserved hrp Genes of Phytopathogenic Bacteria," *Molecular Microbiology*, 20(3):681–683 (1996).

Bonnet et al., "Acquired Resistance Triggered By Elicitins In Tobacco and Other Plants," *European Journal of Plant Pathology*, 102:181–192 (1996).

Cui et al, "The RsmA⁻ Mutants of *Erwinia carotovora* subsp. *carotovora* Strain Ecc71 Overexpress hrpN$_{Ecc}$ and Elicit a Hypersensitive Reaction–like Response in Tobacco Leaves," *Molecular Plant–Microbe Interactions*, 9(7):565–573 (1996).

Gopalan et al., "Bacterial Genes Involved in the Elicitation of Hypersensitive Response and Pathogenesis," *Plant Disease*, 80(6):604–610 (1996).

Hoffland et al., "Comparison of Systemic Resistance Induced by Avirulent and Nonpathogenic Pseudomonas Species," *Phytopathology*, 86(7):757–762 (1996).

Ryals et al., "Systemic Acquired Resistance," *The Plant Cell* , 8:1809–1819 (1996).

Wei et al., "Induced Systemic Resistance to Cucumber Dieseases and Increased Plant Growth by Plant GrowthPromoting Rhizobacteria Under Field Conditions," *Phytopathology*, 86:221–224 (1996).

Wengelnik et al., "Expression and Localization of HrpA1, a Protein of *Xanthomonas campestris* pv. vesicatoria Essential for Pathogenicity and Induction of the Hypersensitive Reaction," *Journal of Bacteriology*, 178:1061–1069 (1996).

Inbar et al., "Elicitors of Plant Defensive Systems Reduce Insect Densities and Disease Incidence," *Journal of Chemical Ecology*, 24(1):135–149 (1998).

Jin et al., "A Truncated Fragment of Harpin$_{Pss}$ Induces Systemic Resistance To *Xanthomonas campetris* pv. *oryzae* In Rice," *Physiological and Molecular Plant Pathology*, 51:243–257 (1997).

Alfano et al., "Analysis of the Role of the Pseudomonas Syringae pv. Syringae HrpZ Harpin in Elicitation of the Hypersensitive Response in Tobacco Using Functionally Non–Polar hrpZ Deletion Mutations, Truncated HrpZ Fragments, and hrmA Mutations," *Molecular Microbiology*, 19:715–728 (1996).

Linthorst et al., "Constitutive Expression of Pathogenesis-Related Proteins RP–1, GRP, and PR–S in Tobacco Has No Effect on Virus Infection," *The Plant Cell*, 1:285–291 (1989).

Malamy et al., Salicylic Acid and Plant Disease Resistance, *The Plant Journal*, 2:643–654 (1992).

McGurl et al., "Structure, Expression, and Antisense Inhibition of the Systemin Precursor Gene," *Science*, 255:1570–1573 (1992).

Wei et al., "hrpL Activates *Erwinia amylovora hrp* Gene Transcription and Is a Member of the ECF Subfamily of σ Factors," *Journal of Bacteriology*, 177:6201–6210 (1995).

Nissinen et al., "Clavibacter Michiganensis Subsp. Sepedonicus Elicits a Hypersensitive Response in Tobacco and Secretes Hypersensitive Response–Inducing Protein," *Phytopathology*, 87:678–684 (1997) (Abstract only).

Schulte et al., Expression of the *Xanthomonas campestris* pv. Vesicatoria hrp Gene Cluster, Which Determines Pathogenicity and Hypersensitivity on Pepper and Tomato, Is Plant Inducible, *Journal of Bacteriology*, 174:815–823 (1992).

Yu, "Elicitins from Phytophthora and Basic Resistance in Tobacco," *Proc. Natl. Acad. Sci. USA*, 92:4088–4094 (1995).

Wu et al., "Disease Resistance Conferred by Expression of a Gene Encoding $H_2O_2$–generating Glucose Oxidase in Transgenic Potato Plants," *The Plant Cell*, 7:1357–1368 (1995).

Kim et al., "HrpW of *Erwinia amylovora*, a New Harpin That Contains a Domain Homologous to Pectate Lyases of a Distinct Class," *Journal of Bacteriology* 180:5203–5210 (1998).

Charkowski et al., "The *Pseudomonas syringae* pv. Tomato HrpW Protein Has Domains Similar to Harpins and Pectate Lyases and Can Elicit the Plant Hypersensitive Response and Bind to Pectate," *Journal of Bacteriology* 180:5211–5217 (1998).

Lorang et al., "Characterization of avrE from *Pseudomonas syringae* pv. Tomato: A hrp–Linked Avirulence Locus Consisting Of a Least Two Transcriptional Units," *MPMI* 8:49–57 (1995).

* cited by examiner

1 ———————— harpin ————————
1                                                                403

C-terminal fragments
3 ——————————————————————
   105                                                           403
4      ————————————————————
        169                                                      403
5            ——————————————
              210                                                403
6                   ———————
                     267                                         403
7                              ———
                                343    403

N-terminal fragments
8  ———
    1   75
9  ——————
    1      104
10 —————————
    1           168
11 ————————————————
    1                    266
12 ——————————————————————
    1                            342

Internal fragments
13     ——————————
        76        209
14     ———————
        76    168
15         ————————
            105     209
16              ———
                 169  209
17         ———
            105   168
18        —————————              Synthesized oligopeptides
           99        209
19            ——————                    ———
               137   204                 150  179
20            ————                       ———
               137 180                   137 166
21         ————————                     ———
            105      180                 121 150
22              ——————                   ———
                 150   209               137 156
23              ———
                 150 180

Harpin fragments derived from HrpN of Erwinia amylovora

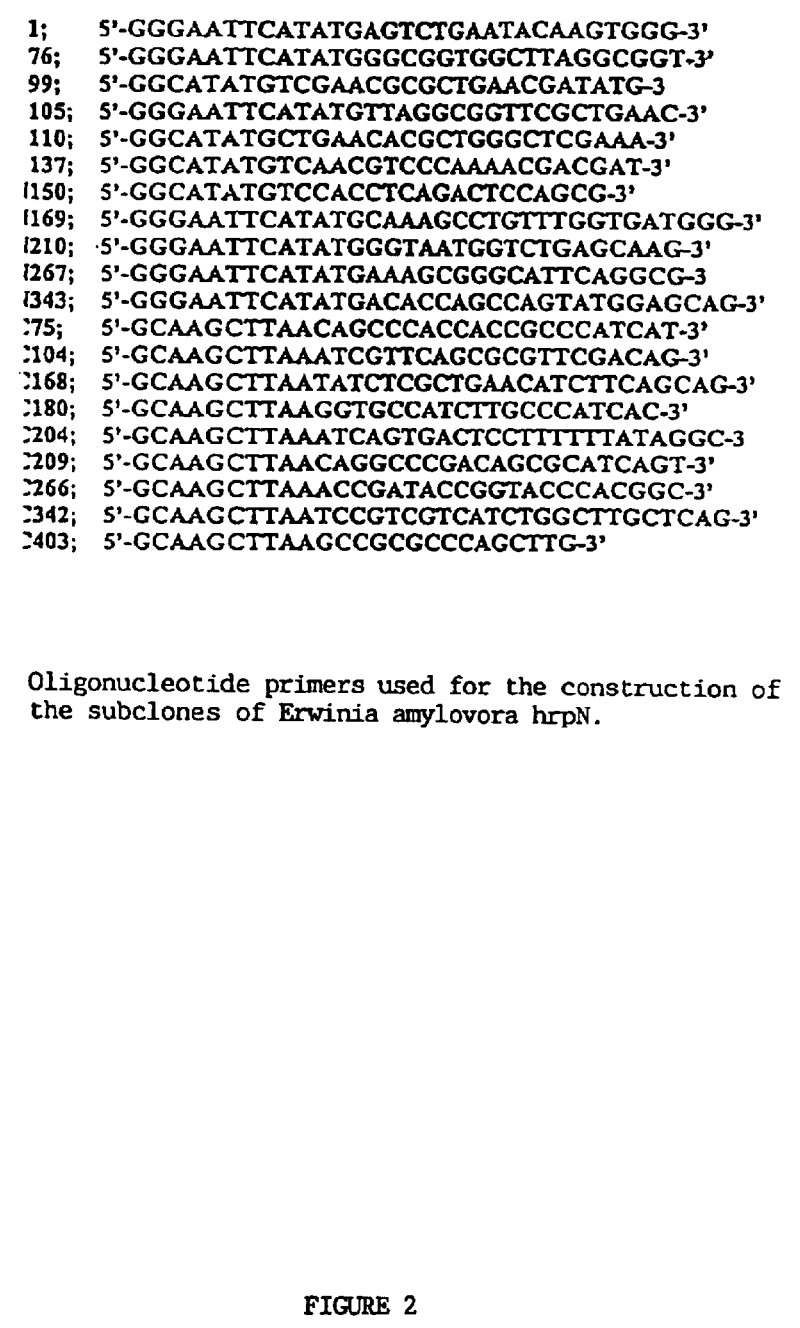

1; 5'-GGGAATTCATATGAGTCTGAATACAAGTGGG-3'
76; 5'-GGGAATTCATATGGGCGGTGGCTTAGGCGGT-3'
99; 5'-GGCATATGTCGAACGCGCTGAACGATATG-3
105; 5'-GGGAATTCATATGTTAGGCGGTTCGCTGAAC-3'
110; 5'-GGCATATGCTGAACACGCTGGGCTCGAAA-3'
137; 5'-GGCATATGTCAACGTCCCAAAACGACGAT-3'
150; 5'-GGCATATGTCCACCTCAGACTCCAGCG-3'
169; 5'-GGGAATTCATATGCAAAGCCTGTTTGGTGATGGG-3'
210; 5'-GGGAATTCATATGGGTAATGGTCTGAGCAAG-3'
267; 5'-GGGAATTCATATGAAAGCGGGCATTCAGGCG-3
343; 5'-GGGAATTCATATGACACCAGCCAGTATGGAGCAG-3'
75; 5'-GCAAGCTTAACAGCCCACCACCGCCCATCAT-3'
104; 5'-GCAAGCTTAAATCGTTCAGCGCGTTCGACAG-3'
168; 5'-GCAAGCTTAATATCTCGCTGAACATCTTCAGCAG-3'
180; 5'-GCAAGCTTAAGGTGCCATCTTGCCCATCAC-3'
204; 5'-GCAAGCTTAAATCAGTGACTCCTTTTTTATAGGC-3
209; 5'-GCAAGCTTAACAGGCCCGACAGCGCATCAGT-3'
266; 5'-GCAAGCTTAAACCGATACCGGTACCCACGGC-3'
342; 5'-GCAAGCTTAATCCGTCGTCATCTGGCTTGCTCAG-3'
403; 5'-GCAAGCTTAAGCCGCGCCCAGCTTG-3'

Oligonucleotide primers used for the construction of the subclones of Erwinia amylovora hrpN.

FIGURE 2

HYPERSENSITIVE RESPONSE ELICITOR FRAGMENTS WHICH ARE ACTIVE BUT DO NOT ELICIT A HYPERSENSITIVE RESPONSE

This application claims benefit of U.S. Provisional Patent Application Ser. No. 60/103,050, filed Oct. 5, 1998.

FIELD OF THE INVENTION

The present invention relates to active fragments of a hypersensitive response elicitor which fragments do not elicit a hypersensitive response.

BACKGROUND OF THE INVENTION

Interactions between bacterial pathogens and their plant hosts generally fall into two categories: (1) compatible (pathogen-host), leading to intercellular bacterial growth, symptom development, and disease development in the host plant; and (2) incompatible (pathogen-nonhost), resulting in the hypersensitive response, a particular type of incompatible interaction occurring, without progressive disease symptoms. During compatible interactions on host plants, bacterial populations increase dramatically and progressive symptoms occur. During incompatible interactions, bacterial populations do not increase, and progressive symptoms do not occur.

The hypersensitive response is a rapid, localized necrosis that is associated with the active defense of plants against many pathogens (Kiraly, Z., "Defenses Triggered by the Invader: Hypersensitivity," pages 201-224 in: *Plant Disease: An Advanced Treatise*, Vol. 5, J. G. Horsfall and E. B. Cowling, ed. Academic Press New York (1980); Klement, Z., "Hypersensitivity," pages 149–177 in: *Phypahogenic Prokaryotes*, Vol. 2, M. S. Mount and G. H. Lacy, ed. Academic Press, New York (1982)). The hypersensitive response elicited by bacteria is readily observed as a tissue collapse if high concentrations ($\geqq 10^7$ cells/ml) of a limited host-range pathogen like *Pseudomonas syringae* or *Erwinia amylovora* are infiltrated into the leaves of nonhost plants (necrosis occurs only in isolated plant cells at lower levels of inoculum) (Klement, Z., "Rapid Detection of Pathogenicity of Phytopathogenic Pseudomonads," *Nature* 199:299–300; Klement, et al., "Hypersensitive Reaction Induced by Phytopathogenic Bacteria in the Tobacco Leaf," *Phytopatholgy* 54:474–477 (1963); Turner, et al., "The Quantitative Relation Between Plant and Bacterial Cells Involved in the Hypersensitive Reaction," *Phytopathology* 64:885–890 (1974); Klement, Z., "Hypersensitivity," pages 149–177 in *Phytopathogenic Prokaryotes*, Vol. 2., M. S. Mount and G. H. Lacy, ed. Academic Press, New York (1982)). The capacities to elicit the hypersensitive response in a nonhost and be pathogenic in a host appear linked. As noted by Klement, Z., "Hypersensitivity," pages 149–177 in *Phytopathogenic Prokaryotes*, Vol. 2., M. S. Mount and G. H. Lacy, ed. Academic Press, New York, these pathogens also cause physiologically similar, albeit delayed, necroses in their interactions with compatible hosts. Furthermore, the ability to produce the hypersensitive response or pathogenesis is dependent on a common set of genes, denoted hrp (Lindgren, P. B., et al., "Gene Cluster of *Pseudomonas syringae* pv. 'phaseolicola' Controls Pathogenicity of Bean Plants and Hypersensitivity on Nonhost Plants," *J. Bacteriol.* 168:512–22 (1986); Willis, D. K., et al., "hrp Genes of Phytopathogenic Bacteria," *Mol. Plant-Microbe Interact.* 4:132–138 (1991)). Consequently, the hypersensitive response may hold clues to both the nature of plant defense and the basis for bacterial pathogenicity.

The hrp genes are widespread in Grain-negative plant pathogens, where they are clustered, conserved, and in some cases interchangeable (Willis, D. K., et al., "hrp Genes of Phytopathogenic Bacteria," Mol. Plant-Microbe Interact. 4:132–138 (1991); Bonas, U., "hrp Genes of Phytopathogenic Bacteria," pages 79–98 in: *Current Topics in Microbiology and Immunology: Bacterial Pathogenesis of Plants and Animals—Molecular and Cellular Mechanisms*, J. L. Dangl, ed. Springer-Verlag, Berlin (1994)). Several hrp genes encode components of a protein secretion pathway similar to one used by Yersinia, Shigella, and Salmonella spp. to secrete proteins essential in animal diseases (Van Gijsegem, et al., "Evolutionary Conservation of Pathogenicity Determinants Among Plant and Animal Pathogenic Bacteria," *Trends Microbiol.* 1 :175–180 (1993)). In *E. amylovora, P. syringae*, and *P. solanacearum*, hrp genes have been shown to control the production and secretion of glycine-rich, protein elicitors of the hypersensitive response (He, S. Y., et al. "Pseudomonas Syringae pv. Syringae HarpinPss: a Protein that is Secreted via the Hrp Pathway and Elicits the Hypersensitive Response in Plants," *Cell* 73:1255–1266 (1993), Wei, Z.-H., et al., "HrpI of *Erwinia amylovora* Functions in Secretion of Harpin and is a Member of a New Protein Family," *J. Bacteriol.* 175:7958–7967 (1993); Arlat, M. et al. "PopA1, a Protein Which Induces a Hypersensitive-like Response on Specific Petunia Genotypes, is Secreted via the Hrp Pathway of *Pseudomonas solanacearum," EMBO J.* 13:543–553 (1994)).

The first of these proteins was discovered in *E. amylovora* Ea321, a bacterium that causes fire blight of rosaceous plants, and was designated harpin (Wei, Z.-M., et al, "Harpin, Elicitor of the Hypersensitive Response Produced by the Plant Pathogen *Erwinia amylovora," Science* 257:85–88 (1992)). Mutations in the encoding hrpN gene revealed that harpin is required for *E. amylovora* to elicit a hypersensitive response in nonhost tobacco leaves and incite disease symptoms in highly susceptible pear fruit. The *P. solanacearum* GMI 1000 PopA1 protein has similar physical properties and also elicits the hypersensitive response in leaves of tobacco, which is not a host of that strain (Arlat, et al. "PopA1, a Protein Which Induces a Hypersensitive-like Response on Specific Petunia Genotypes, is Secreted via the Hrp Pathway of *Pseudomonas solanacearum," EMBO J.* 13:543–53 (1994)). However, *P. solanacearum* popA mutants still elicit the hypersensitive response in tobacco and incite disease in tomato. Thus, the role of these glycine-rich hypersensitive response elicitors can vary widely among Gram-negative plant pathogens.

Other plant pathogenic hypersensitive response elicitors have been isolated, cloned, and sequenced. These include: *Erwinia chrysanthemi* (Bauer, et. al., "*Erwinia chrysanthemi* $Harpin_{Ech}$: Soft-Rot Pathogenesis," *MPMI* 8(4): 484–91 (1995)); *Erwinia carolovora* (Cui, et al., "The $RsmA^-$ Mutants of *Erwinia carotovora* subsp. carotovora Strain Ecc71 Overexpress $hrpN_{Ecc}$ and Elicit a Hypersensitive Reaction-like Response in Tobacco Leaves," *MPMI* 9(7): 565–73 (1996)); *Erwinia stewartii* (Ahmad, et. al., "Harpin is not Necessary for the Pathogenicity of *Erwinia stewartii* on Maize," *8th Int'l Cong. Molec. Plant-Microb. Inter.* Jul. 14–19, 1996 and Ahmad, et. al., "Harpin is not Necessary for the Pathogenicity of *Erwinia stewartii* on Maize," *Ann. Mtg. Am. Phytopath. Soc.* Jul. 27–31, 1996); and *Pseudomonas syringae* pv. syringae (WO 94/26782 to Cornell Research Foundation, Inc.).

The present invention seeks to identify fragments of hypersensitive response elicitor proteins or polypeptides, which fragments do not elicit a hypersensitive response but are active when utilized in conjunction with plants.

SUMMARY OF THE INVENTION

The present invention is directed to isolated fragments of an Erwinia hypersensitive response elicitor protein or polypeptide which fragments do not elicit a hypersensitive response in plants but are otherwise active when utilized in conjunction with plants. Also disclosed are isolated DNA molecules which encode such fragments.

The fragments of hypersensitive response elicitors according to the present invention have the following activity when utilized in conjunction with plants: imparting disease resistance to plants, enhancing plant growth and/or controlling insects. This involves applying the fragments in a non-infectious form to plants or plant seeds under conditions effective to impart disease resistance, to enhance plant growth, and/or to control insects on plants or plants grown from the plant seeds.

As an alternative to applying the fragments to plants or plant seeds in order to impart disease resistance, to enhance plant growth, and/or to control insects on plants, transgenic plants or plant seeds can be utilized. When utilizing transgenic plants, this involves providing a transgenic plant transformed with a DNA molecule encoding a fragment of a hypersensitive response elicitor protein or polypeptide in accordance with the present invention and growing the plant under conditions effective to impart disease resistance, to enhance plant growth, and/or to control insects in the plants or plants grown from the plant seeds. Alternatively, a transgenic plant seed transformed with the DNA molecule encoding such a fragment can be provided and planted in soil. A plant is then propagated under conditions effective to impart disease resistance, to enhance plant growth, and/or to control insects on plants or plants grown from the plant seeds.

BRIEF DESCRIPTION OF THE DRAWINGS

FIG. 2 shows a list of synthesized oligonucleotide primers for construction of truncated harpin proteins. N represents the N-terminus (5' region), and C represents the C-terminus (3' region). The primers correspond to the indicated sequence identification numbers for the present application: N1 (SEQ ID NO: 1), N76 (SEQ ID NO: 2), N99 (SEQ ID NO: 3), N105 (SEQ ID NO: 4), N110 (SEQ ID NO: 5), N137 (SEQ ID NO: 6),N150 (SEQ ID NO: 7), N169 (SEQ ID NO: 8), N210 (SEQ ID NO: 9), N267 (SEQ ID NO: 10), N343 (SEQ ID NO: 11), C75 (SEQ ID NO: 12), C104 (SEQ ID NO: 13), C168 (SEQ ID NO: 14), C180 (SEQ ID NO: 15), C204 (SEQ ID NO: 16), C209 (SEQ ID NO: 17), C266 (SEQ ID NO:. 18), C342 (SEQ ID NO: 19), and C403 (SEQ ID NO: 20).

DETAILED DESCRIPTION OF THE INVENTION

Figure 1:
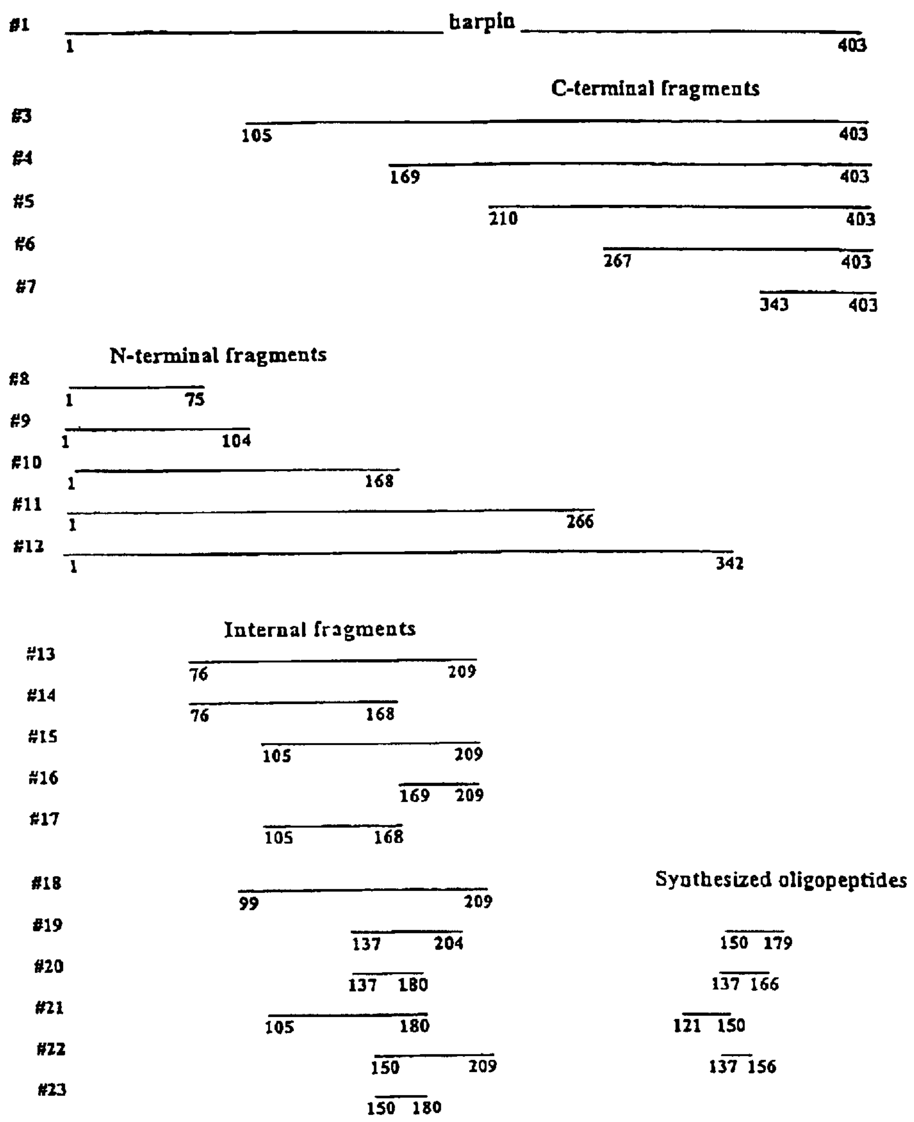
FIG. 1 shows truncated proteins of the hypersensitive response elicitor protein or polypeptide.

The present invention is directed to isolated fragments of a hypersensitive response elicitor protein or polypeptide where the fragments do not elicit a hypersensitive response but have other activity in plants. Also disclosed are DNA molecules encoding such fragments as well as expression systems, host cells, and plants containing such molecules. Uses of the fragments themselves and the DNA molecules encoding them are disclosed.

The fragments of hypersensitive response elicitor polypeptides or proteins according to the present invention are derived from hypersensitive response elicitor polypeptides or proteins of a wide variety of fungal and bacterial pathogens. Such polypeptides or proteins are able to elicit local necrosis in plant tissue contacted by the elicitor. Examples of suitable bacterial sources of polypeptide or protein elicitors include Erwinia, Pseudomonas, and Xanthomonas species (e.g., the following bacteria: *Erwinia amylovora, Erwinia chrysanthemi, Erwinia stewartit, Erwinia carotovora, Pseudomonas syringae, Pseudomonas solancearum, Xanthomonas campestris*, and mixtures thereof).

An example of a fungal source of a hypersensitive response elicitor protein or polypeptide is Phytophthora. Suitable species of Phytophthora include *Phytophihora parasitica, Phytophthora cryptogea, Phytophthora cinnamomi, Phytophthora capsici, Phytophthora megasperma, and Phytophthora citrophihora.*

The hypersensitive response elicitor polypeptide or protein from *Erwinia chrysanthemi* has an amino acid sequence corresponding to SEQ ID NO: 21 as follows:

```
Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
    50                  55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
        115                 120                 125

Leu Ala Asn Ser Met Leu Asn Ala Ser Gln Met Thr Gln Gly Asn Met
    130                 135                 140
```

-continued

```
Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
            180                 185                 190

Gly Asn Ala Ile Gly Met Gly Val Gly Gln Asn Ala Ala Leu Ser Ala
        195                 200                 205

Leu Ser Asn Val Ser Thr His Val Asp Gly Asn Asn Arg His Phe Val
    210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
            260                 265                 270

Pro Asp Asp Asp Gly Met Thr Gly Ala Ser Met Asp Lys Phe Arg Gln
        275                 280                 285

Ala Met Gly Met Ile Lys Ser Ala Val Ala Gly Asp Thr Gly Asn Thr
    290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala
```

This hypersensitive response elicitor polypeptide or protein has a molecular weight of 34 kDa, is heat stable, has a glycine content of greater than 16%, and contains substantially no cysteine. The *Erwinia chrysanthemi* hypersensitive response elicitor polypeptide or protein is encoded by a DNA molecule having a nucleotide sequence corresponding to SEQ ID NO: 22 as follows:

```
CGATTTTACC CGGGTGAACG TGCTATGACC GACAGCATCA CGGTATTCGA CACCGTTACG     60

GCGTTTATGG CCGCGATGAA CCGGCATCAG GCGGCGCGCT GGTCGCCGCA ATCCGGCGTC    120

GATCTGGTAT TTCAGTTTGG GGACACCGGG CGTGAACTCA TGATGCAGAT TCAGCCGGGG    180

CAGCAATATC CCGGCATGTT GCGCACGCTG CTCGCTCGTC GTTATCAGCA GGCGGCAGAG    240

TGCGATGGCT GCCATCTGTG CCTGAACGGC AGCGATGTAT TGATCCTCTG GTGGCCGCTG    300

CCGTCGGATC CCGGCAGTTA TCCGCAGGTG ATCGAACGTT TGTTTGAACT GGCGGGAATG    360

ACGTTGCCGT CGCTATCCAT AGCACCGACG GCGCGTCCGC AGACAGGGAA CGGACGCGCC    420

CGATCATTAA GATAAAGGCG GCTTTTTTTA TTGCAAAACG GTAACGGTGA GGAACCGTTT    480

CACCGTCGGC GTCACTCAGT AACAAGTATC CATCATGATG CCTACATCGG GATCGGCGTG    540

GGCATCCGTT GCAGATACTT TTGCGAACAC CTGACATGAA TGAGGAAACG AAATTATGCA    600

AATTACGATC AAAGCGCACA TCGGCGGTGA TTTGGGCGTC TCCGGTCTGG GGCTGGGTGC    660

TCAGGGACTG AAAGGACTGA ATTCCGCGGC TTCATCGCTG GGTTCCAGCG TGGATAAACT    720

GAGCAGCACC ATCGATAAGT TGACCTCCGC GCTGACTTCG ATGATGTTTG GCGGCGCGCT    780

GGCGCAGGGG CTGGGCGCCA GCTCGAAGGG GCTGGGGATG AGCAATCAAC TGGGCCAGTC    840

TTTCGGCAAT GGCGCGCAGG GTGCGAGCAA CCTGCTATCC GTACCGAAAT CCGGCGGCGA    900

TGCGTTGTCA AAAATGTTTG ATAAAGCGCT GGACGATCTG CTGGGTCATG ACACCGTGAC    960
```

-continued

```
CAAGCTGACT AACCAGAGCA ACCAACTGGC TAATTCAATG CTGAACGCCA GCCAGATGAC    1020

CCAGGGTAAT ATGAATGCGT TCGGCAGCGG TGTGAACAAC GCACTGTCGT CCATTCTCGG    1080

CAACGGTCTC GGCCAGTCGA TGAGTGGCTT CTCTCAGCCT TCTCTGGGGG CAGGCGGCTT    1140

GCAGGGCCTG AGCGGCGCGG GTGCATTCAA CCAGTTGGGT AATGCCATCG GCATGGGCGT    1200

GGGGCAGAAT GCTGCGCTGA GTGCGTTGAG TAACGTCAGC ACCCACGTAG ACGGTAACAA    1260

CCGCCACTTT GTAGATAAAG AAGATCGCGG CATGGCGAAA GAGATCGGCC AGTTTATGGA    1320

TCAGTATCCG GAAATATTCG GTAAACCGGA ATACCAGAAA GATGGCTGGA GTTCGCCGAA    1380

GACGGACGAC AAATCCTGGG CTAAAGCGCT GAGTAAACCG GATGATGACG GTATGACCGG    1440

CGCCAGCATG GACAAATTCC GTCAGGCGAT GGGTATGATC AAAAGCGCGG TGGCGGGTGA    1500

TACCGGCAAT ACCAACCTGA ACCTGCGTGG CGCGGGCGGT GCATCGCTGG GTATCGATGC    1560

GGCTGTCGTC GGCGATAAAA TAGCCAACAT GTCGCTGGGT AAGCTGGCCA ACGCCTGATA    1620

ATCTGTGCTG GCCTGATAAA GCGGAAACGA AAAAAGAGAC GGGGAAGCCT GTCTCTTTTC    1680

TTATTATGCG GTTTATGCGG TTACCTGGAC CGGTTAATCA TCGTCATCGA TCTGGTACAA    1740

ACGCACATTT TCCCGTTCAT TCGCGTCGTT ACGCGCCACA ATCGCGATGG CATCTTCCTC    1800

GTCGCTCAGA TTGCGCGGCT GATGGGGAAC GCCGGGTGGA ATATAGAGAA ACTCGCCGGC    1860

CAGATGGAGA CACGTCTGCG ATAAATCTGT GCCGTAACGT GTTTCTATCC GCCCCTTTAG    1920

CAGATAGATT GCGGTTTCGT AATCAACATG GTAATGCGGT TCCGCCTGTG CGCCGGCCGG    1980

GATCACCACA ATATTCATAG AAAGCTGTCT TGCACCTACC GTATCGCGGG AGATACCGAC    2040

AAAATAGGGC AGTTTTTGCG TGGTATCCGT GGGGTGTTCC GGCCTGACAA TCTTGAGTTG    2100

GTTCGTCATC ATCTTTCTCC ATCTGGGCGA CCTGATCGGT T                        2141
```

The hypersensitive response elicitor polypeptide or protein derived from *Erwinia* amylovora has an amino acid sequence corresponding to SEQ ID NO: 23 as follows:

```
Met Ser Leu Asn Thr Ser Gly Leu Gly Ala Ser Thr Met Gln Ile Ser
1               5                   10                  15

Ile Gly Gly Ala Gly Gly Asn Asn Gly Leu Leu Gly Thr Ser Arg Gln
            20                  25                  30

Asn Ala Gly Leu Gly Gly Asn Ser Ala Leu Gly Leu Gly Gly Gly Asn
        35                  40                  45

Gln Asn Asp Thr Val Asn Gln Leu Ala Gly Leu Leu Thr Gly Met Met
    50                  55                  60

Met Met Met Ser Met Met Gly Gly Gly Gly Leu Met Gly Gly Gly Leu
65                  70                  75                  80

Gly Gly Gly Leu Gly Asn Gly Leu Gly Gly Ser Gly Gly Leu Gly Glu
                85                  90                  95

Gly Leu Ser Asn Ala Leu Asn Asp Met Leu Gly Gly Ser Leu Asn Thr
            100                 105                 110

Leu Gly Ser Lys Gly Gly Asn Asn Thr Thr Ser Thr Thr Asn Ser Pro
        115                 120                 125

Leu Asp Gln Ala Leu Gly Ile Asn Ser Thr Ser Gln Asn Asp Asp Ser
    130                 135                 140

Thr Ser Gly Thr Asp Ser Thr Ser Asp Ser Ser Asp Pro Met Gln Gln
145                 150                 155                 160

Leu Leu Lys Met Phe Ser Glu Ile Met Gln Ser Leu Phe Gly Asp Gly
                165                 170                 175
```

-continued

```
Gln Asp Gly Thr Gln Gly Ser Ser Ser Gly Gly Lys Gln Pro Thr Glu
            180                 185                 190

Gly Glu Gln Asn Ala Tyr Lys Lys Gly Val Thr Asp Ala Leu Ser Gly
        195                 200                 205

Leu Met Gly Asn Gly Leu Ser Gln Leu Leu Gly Asn Gly Gly Leu Gly
    210                 215                 220

Gly Gly Gln Gly Gly Asn Ala Gly Thr Gly Leu Asp Gly Ser Ser Leu
225                 230                 235                 240

Gly Gly Lys Gly Leu Gln Asn Leu Ser Gly Pro Val Asp Tyr Gln Gln
                245                 250                 255

Leu Gly Asn Ala Val Gly Thr Gly Ile Gly Met Lys Ala Gly Ile Gln
            260                 265                 270

Ala Leu Asn Asp Ile Gly Thr His Arg His Ser Ser Thr Arg Ser Phe
        275                 280                 285

Val Asn Lys Gly Asp Arg Ala Met Ala Lys Glu Ile Gly Gln Phe Met
    290                 295                 300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330                 335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
        355                 360                 365

Gly Asn Leu Gln Ala Arg Gly Ala Gly Gly Ser Ser Leu Gly Ile Asp
    370                 375                 380

Ala Met Met Ala Gly Asp Ala Ile Asn Asn Met Ala Leu Gly Lys Leu
385                 390                 395                 400

Gly Ala Ala
```

This hypersensitive response elicitor polypeptide or protein has a molecular weight of about 39 kDa, has a pI of approximately 4.3, and is heat stable at 100° C. for at least 10 minutes. This hypersensitive response elicitor polypeptide or protein has substantially no cysteine. The hypersensitive response elicitor polypeptide or protein derived from *Erwinia amylovora* is more fully described in Wei, Z.-M., R. J. Laby, C. H. Zumoff, D. W. Bauer, S.-Y. He, A. Collmer, and S. V. Beer, "Harpin, Elicitor of the Hypersensitive Response Produced by the Plant Pathogen *Erwinia amylovora*," *Science* 257:85–88 (1992), which is hereby incorporated by reference. The DNA molecule encoding this polypeptide or protein has a nucleotide sequence corresponding to SEQ ID NO: 24 as follows:

```
AAGCTTCGGC ATGGCACGTT TGACCGTTGG GTCGGCAGGG TACGTTTGAA TTATTCATAA     60

GAGGAATACG TTATGAGTCT GAATACAAGT GGGCTGGGAG CGTCAACGAT GCAAATTTCT    120

ATCGGCGGTG CGGGCGGAAA TAACGGGTTG CTGGGTACCA GTCGCCAGAA TGCTGGGTTG    180

GGTGGCAATT CTGCACTGGG GCTGGGCGGC GGTAATCAAA ATGATACCGT CAATCAGCTG    240

GCTGGCTTAC TCACCGGCAT GATGATGATG ATGAGCATGA TGGGCGGTGG TGGGCTGATG    300

GGCGGTGGCT TAGGCGGTGG CTTAGGTAAT GGCTTGGGTG GCTCAGGTGG CCTGGGCGAA    360

GGACTGTCGA ACGCGCTGAA CGATATGTTA GGCGGTTCGC TGAACACGCT GGGCTCGAAA    420

GGCGGCAACA ATACCACTTC AACAACAAAT TCCCCGCTGG ACCAGGCGCT GGGTATTAAC    480

TCAACGTCCC AAAACGACGA TTCCACCTCC GGCACAGATT CCACCTCAGA CTCCAGCGAC    540

CCGATGCAGC AGCTGCTGAA GATGTTCAGC GAGATAATGC AAAGCCTGTT TGGTGATGGG    600

CAAGATGGCA CCCAGGGCAG TTCCTCTGGG GGCAAGCAGC CGACCGAAGG CGAGCAGAAC    660

GCCTATAAAA AAGGAGTCAC TGATGCGCTG TCGGGCCTGA TGGGTAATGG TCTGAGCCAG    720
```

-continued

```
CTCCTTGGCA ACGGGGGACT GGGAGGTGGT CAGGGCGGTA ATGCTGGCAC GGGTCTTGAC     780
GGTTCGTCGC TGGGCGGCAA AGGGCTGCAA AACCTGAGCG GGCCGGTGGA CTACCAGCAG     840
TTAGGTAACG CCGTGGGTAC CGGTATCGGT ATGAAAGCGG GCATTCAGGC GCTGAATGAT     900
ATCGGTACGC ACAGGCACAG TTCAACCCGT TCTTTCGTCA ATAAAGGCGA TCGGGCGATG     960
GCGAAGGAAA TCGGTCAGTT CATGGACCAG TATCCTGAGG TGTTTGGCAA GCCGCAGTAC    1020
CAGAAAGGCC CGGGTCAGGA GGTGAAAACC GATGACAAAT CATGGGCAAA AGCACTGAGC    1080
AAGCCAGATG ACGACGGAAT GACACCAGCC AGTATGGAGC AGTTCAACAA AGCCAAGGGC    1140
ATGATCAAAA GGCCCATGGC GGGTGATACC GGCAACGGCA ACCTGCAGGC ACGCGGTGCC    1200
GGTGGTTCTT CGCTGGGTAT TGATGCCATG ATGGCCGGTG ATGCCATTAA CAATATGGCA    1260
CTTGGCAAGC TGGGCGCGGC TTAAGCTT                                       1288
```

Another potentially suitable hypersensitive response elicitor from *Erwinia amylovora* is disclosed in U.S. patent application Ser. No. 09/120,927, which is hereby incorporated by reference. The protein is encoded by a DNA molecule having a nucleic acid sequence of SEQ ID NO: 25 as follows:

```
ATGTCAATTC TTACGCTTAA CAACAATACC TCGTCCTCGC CGGGTCTGTT CCAGTCCGGG      60
GGGGACAACG GGCTTGGTGG TCATAATGCA AATTCTGCGT TGGGGCAACA ACCCATCGAT     120
CGGCAAACCA TTGAGCAAAT GGCTCAATTA TTGGCGGAAC TGTTAAAGTC ACTGCTATCG     180
CCACAATCAG GTAATGCGGC AACCGGAGCC GGTGGCAATG ACCAGACTAC AGGAGTTGGT     240
AACGCTGGCG GCCTGAACGG ACGAAAAGGC ACAGCAGGAA CCACTCCGCA GTCTGACAGT     300
CAGAACATGC TGAGTGAGAT GGGCAACAAC GGGCTGGATC AGGCCATCAC GCCCGATGGC     360
CAGGGCGGCG GGCAGATCGG CGATAATCCT TTACTGAAAG CCATGCTGAA GCTTATTGCA     420
CGCATGATGG ACGGCCAAAG CGATCAGTTT GGCCAACCTG GTACGGGCAA CAACAGTGCC     480
TCTTCCGGTA CTTCTTCATC TGGCGGTTCC CCTTTTAACG ATCTATCAGG GGGGAAGGCC     540
CCTTCCGGCA ACTCCCCTTC CGGCAACTAC TCTCCCGTCA GTACCTTCTC ACCCCCATCC     600
ACGCCAACGT CCCCTACCTC ACCGCTTGAT TTCCCTTCTT CTCCCACCAA AGCAGCCGGG     660
GGCAGCACGC CGGTAACCGA TCATCCTGAC CCTGTTGGTA GCGCGGGCAT CGGGGCCGGA     720
AATTCGGTGG CCTTCACCAG CGCCGGCGCT AATCAGACGG TGCTGCATGA CACCATTACC     780
GTGAAAGCGG GTCAGGTGTT TGATGGCAAA GGACAAACCT TCACCGCCGG TTCAGAATTA     840
GGCGATGGCG GCCAGTCTGA AAACCAGAAA CCGCTGTTTA TACTGGAAGA CGGTGCCAGC     900
CTGAAAAACG TCACCATGGG CGACGACGGG GCGGATGGTA TTCATCTTTA CGGTGATGCC     960
AAAATAGACA ATCTGCACGT CACCAACGTG GGTGAGGACG CGATTACCGT TAAGCCAAAC    1020
AGCGCGGGCA AAAAATCCCA CGTTGAAATC ACTAACAGTT CCTTCGAGCA CGCCTCTGAC    1080
AAGATCCTGC AGCTGAATGC CGATACTAAC CTGAGCGTTG ACAACGTGAA GGCCAAAGAC    1140
TTTGGTACTT TTGTACGCAC TAACGGCGGT CAACAGGGTA ACTGGGATCT GAATCTGAGC    1200
CATATCAGCG CAGAAGACGG TAAGTTCTCG TTCGTTAAAA GCGATAGCGA GGGGCTAAAC    1260
GTCAATACCA GTGATATCTC ACTGGGTGAT GTTGAAAACC ACTACAAAGT GCCGATGTCC    1320
GCCAACCTGA AGGTGGCTGA ATGA                                           1344
```

See GenBank Accession No. U94513. The isolated DNA molecule of the present invention encodes a hypersensitive response elicitor protein or polypeptide having an amino acid sequence of SEQ ID NO: 26 as follows:

```
Met Ser Ile Leu Thr Leu Asn Asn Asn Thr Ser Ser Ser Pro Gly Leu
1               5                   10                  15

Phe Gln Ser Gly Gly Asp Asn Gly Leu Gly Gly His Asn Ala Asn Ser
            20                  25                  30

Ala Leu Gly Gln Gln Pro Ile Asp Arg Gln Thr Ile Glu Gln Met Ala
        35                  40                  45

Gln Leu Leu Ala Glu Leu Leu Lys Ser Leu Leu Ser Pro Gln Ser Gly
    50                  55                  60

Asn Ala Ala Thr Gly Ala Gly Gly Asn Asp Gln Thr Thr Gly Val Gly
65                  70                  75                  80

Asn Ala Gly Gly Leu Asn Gly Arg Lys Gly Thr Ala Gly Thr Thr Pro
                85                  90                  95

Gln Ser Asp Ser Gln Asn Met Leu Ser Glu Met Gly Asn Asn Gly Leu
            100                 105                 110

Asp Gln Ala Ile Thr Pro Asp Gly Gln Gly Gly Gly Gln Ile Gly Asp
        115                 120                 125

Asn Pro Leu Leu Lys Ala Met Leu Lys Leu Ile Ala Arg Met Met Asp
    130                 135                 140

Gly Gln Ser Asp Gln Phe Gly Gln Pro Gly Thr Gly Asn Asn Ser Ala
145                 150                 155                 160

Ser Ser Gly Thr Ser Ser Ser Gly Gly Ser Pro Phe Asn Asp Leu Ser
                165                 170                 175

Gly Gly Lys Ala Pro Ser Gly Asn Ser Pro Ser Gly Asn Tyr Ser Pro
            180                 185                 190

Val Ser Thr Phe Ser Pro Pro Ser Thr Pro Thr Ser Pro Thr Ser Pro
        195                 200                 205

Leu Asp Phe Pro Ser Ser Pro Thr Lys Ala Ala Gly Gly Ser Thr Pro
    210                 215                 220

Val Thr Asp His Pro Asp Pro Val Gly Ser Ala Gly Ile Gly Ala Gly
225                 230                 235                 240

Asn Ser Val Ala Phe Thr Ser Ala Gly Ala Asn Gln Thr Val Leu His
                245                 250                 255

Asp Thr Ile Thr Val Lys Ala Gly Gln Val Phe Asp Gly Lys Gly Gln
            260                 265                 270

Thr Phe Thr Ala Gly Ser Glu Leu Gly Asp Gly Gly Gln Ser Glu Asn
        275                 280                 285

Gln Lys Pro Leu Phe Ile Leu Glu Asp Gly Ala Ser Leu Lys Asn Val
    290                 295                 300

Thr Met Gly Asp Asp Gly Ala Asp Gly Ile His Leu Tyr Gly Asp Ala
305                 310                 315                 320

Lys Ile Asp Asn Leu His Val Thr Asn Val Gly Glu Asp Ala Ile Thr
                325                 330                 335

Val Lys Pro Asn Ser Ala Gly Lys Lys Ser His Val Glu Ile Thr Asn
            340                 345                 350

Ser Ser Phe Glu His Ala Ser Asp Lys Ile Leu Gln Leu Asn Ala Asp
        355                 360                 365

Thr Asn Leu Ser Val Asp Asn Val Lys Ala Lys Asp Phe Gly Thr Phe
    370                 375                 380

Val Arg Thr Asn Gly Gly Gln Gln Gly Asn Trp Asp Leu Asn Leu Ser
385                 390                 395                 400
```

-continued

```
His Ile Ser Ala Glu Asp Gly Lys Phe Ser Phe Val Lys Ser Asp Ser
                405                 410                 415

Glu Gly Leu Asn Val Asn Thr Ser Asp Ile Ser Leu Gly Asp Val Glu
            420                 425                 430

Asn His Tyr Lys Val Pro Met Ser Ala Asn Leu Lys Val Ala Glu
        435                 440                 445
```

This protein or polypeptide is acidic, rich in glycine and serine, and lacks cysteine. It is also heat stable, protease sensitive, and suppressed by inhibitors of plant metabolism. The protein or polypeptide of the present invention has a predicted molecular size of ca. 4.5 kDa.

Another potentially suitable hypersensitive response elicitor from *Erwinia amylovora* is disclosed in U.S. patent application Ser. No. 09/120,663 which is hereby incorporated by reference. The protein is encoded by a DNA molecule having a nucleic acid sequence of SEQ ID NO: 27 as follows:

```
ATGGAATTAA AATCACTGGG AACTGAACAC AAGGCGGCAG TACACACAGC GGCGCACAAC      60
CCTGTGGGGC ATGGTGTTGC CTTACAGCAG GGCAGCAGCA GCAGCAGCCC GCAAAATGCC     120
GCTGCATCAT TGGCGGCAGA AGGCAAAAAT CGTGGGAAAA TGCCGAGAAT TCACCAGCCA     180
TCTACTGCGG CTGATGGTAT CAGCGCTGCT CACCAGCAAA AGAAATCCTT CAGTCTCAGG     240
GGCTGTTTGG GGACGAAAAA ATTTTCCAGA TCGGCACCGC AGGGCCAGCC AGGTACCACC     300
CACAGCAAAG GGGCAACATT GCGCGATCTG CTGGCGCGGG ACGACGGCGA AACGCAGCAT     360
GAGGCGGCCG CGCCAGATGC GGCGCGTTTG ACCCGTTCGG GCGGCGTCAA ACGCCGCAAT     420
ATGGACGACA TGGCCGGGCG GCCAATGGTG AAAGGTGGCA GCGGCGAAGA TAAGGTACCA     480
ACGCAGCAAA AACGGCATCA GCTGAACAAT TTTGGCCAGA TGCGCCAAAC GATGTTGAGC     540
AAAATGGCTC ACCCGGCTTC AGCCAACGCC GGCGATCGCC TGCAGCATTC ACCGCCGCAC     600
ATCCCGGGTA GCCACCACGA AATCAAGGAA GAACCGGTTG GCTCCACCAG CAAGGCAACA     660
ACGGCCCACG CAGACAGAGT GGAAATCGCT CAGGAAGATG ACGACAGCGA ATTCCAGCAA     720
CTGCATCAAC AGCGGCTGGC GCGCGAACGG GAAAATCCAC CGCAGCCGCC CAAACTCGGC     780
GTTGCCACAC CGATTAGCGC CAGGTTTCAG CCCAAACTGA CTGCGGTTGC GGAAAGCGTC     840
CTTGAGGGGA CAGATACCAC GCAGTCACCC CTTAAGCCGC AATCAATGCT GAAAGGAAGT     900
GGAGCCGGGG TAACGCCGCT GGCGGTAACG CTGGATAAAG GCAAGTTGCA GCTGGCACCG     960
GATAATCCAC CCGCGCTCAA TACGTTGTTG AAGCAGACAT TGGGTAAAGA CACCCAGCAC    1020
TATCTGGCGC ACCATGCCAG CAGCGACGGT AGCCAGCATC TGCTGCTGGA CAACAAAGGC    1080
CACCTGTTTG ATATCAAAAG CACCGCCACC AGCTATAGCG TGCTGCACAA CAGCCACCCC    1140
GGTGAGATAA AGGGCAAGCT GGCGCAGGCG GGTACTGGCT CCGTCAGCGT AGACGGTAAA    1200
AGCGGCAAGA TCTCGCTGGG GAGCGGTACG CAAAGTCACA ACAAAACAAT GCTAAGCCAA    1260
CCGGGGGAAG CGCACCGTTC CTTATTAACC GGCATTTGGC AGCATCCTGC TGGCGCAGCG    1320
CGGCCGCAGG GCGAGTCAAT CCGCCTGCAT GACGACAAAA TTCATATCCT GCATCCGGAG    1380
CTGGGCGTAT GGCAATCTGC GGATAAAGAT ACCCACAGCC AGCTGTCTCG CCAGGCAGAC    1440
GGTAAGCTCT ATGCGCTGAA AGACAACCGT ACCCTGCAAA ACCTCTCCGA TAATAAATCC    1500
TCAGAAAAGC TGGTCGATAA AATCAAATCG TATTCCGTTG ATCAGCGGGG GCAGGTGGCG    1560
ATCCTGACGG ATACTCCCGG CCGCCATAAG ATGAGTATTA TGCCCTCGCT GGATGCTTCC    1620
CCGGAGAGCC ATATTTCCCT CAGCCTGCAT TTTGCCGATG CCCACCAGGG GTTATTGCAC    1680
GGGAAGTCGG AGCTTGAGGC ACAATCTGTC GCGATCAGCC ATGGGCGACT GGTTGTGGCC    1740
```

-continued

```
GATAGCGAAG GCAAGCTGTT TAGCGCCGCC ATTCCGAAGC AAGGGGATGG AAACGAACTG    1800
AAAATGAAAG CCATGCCTCA GCATGCGCTC GATGAACATT TTGGTCATGA CCACCAGATT    1860
TCTGGATTTT TCCATGACGA CCACGGCCAG CTTAATGCGC TGGTGAAAAA TAACTTCAGG    1920
CAGCAGCATG CCTGCCCGTT GGGTAACGAT CATCAGTTTC ACCCCGGCTG GAACCTGACT    1980
GATGCGCTGG TTATCGACAA TCAGCTGGGG CTGCATCATA CCAATCCTGA ACCGCATGAG    2040
ATTCTTGATA TGGGGCATTT AGGCAGCCTG GCGTTACAGG AGGGCAAGCT TCACTATTTT    2100
GACCAGCTGA CCAAAGGGTG GACTGGCGCG GAGTCAGATT GTAAGCAGCT GAAAAAAGGC    2160
CTGGATGGAG CAGCTTATCT ACTGAAAGAC GGTGAAGTGA AACGCCTGAA TATTAATCAG    2220
AGCACCTCCT CTATCAAGCA CGGAACGGAA AACGTTTTTT CGCTGCCGCA TGTGCGCAAT    2280
AAACCGGAGC CGGGAGATGC CCTGCAAGGG CTGAATAAAG ACGATAAGGC CCAGGCCATG    2340
GCGGTGATTG GGGTAAATAA ATACCTGGCG CTGACGGAAA AAGGGGACAT TCGCTCCTTC    2400
CAGATAAAAC CCGGCACCCA GCAGTTGGAG CGGCCGGCAC AAACTCTCAG CCGCGAAGGT    2460
ATCAGCGGCG AACTGAAAGA CATTCATGTC GACCACAAGC AGAACCTGTA TGCCTTGACC    2520
CACGAGGGAG AGGTGTTTCA TCAGCCGCGT GAAGCCTGGC AGAATGGTGC CGAAAGCAGC    2580
AGCTGGCACA AACTGGCGTT GCCACAGAGT GAAAGTAAGC TAAAAAGTCT GGACATGAGC    2640
CATGAGCACA AACCGATTGC CACCTTTGAA GACGGTAGCC AGCATCAGCT GAAGGCTGGC    2700
GGCTGGCACG CCTATGCGGC ACCTGAACGC GGGCCGCTGG CGGTGGGTAC CAGCGGTTCA    2760
CAAACCGTCT TTAACCGACT AATGCAGGGG GTGAAAGGCA AGGTGATCCC AGGCAGCGGG    2820
TTGACGGTTA AGCTCTCGGC TCAGACGGGG GGAATGACCG GCGCCGAAGG GCGCAAGGTC    2880
AGCAGTAAAT TTTCCGAAAG GATCCGCGCC TATGCGTTCA ACCCAACAAT GTCCACGCCG    2940
CGACCGATTA AAAATGCTGC TTATGCCACA CAGCACGGCT GGCAGGGGCG TGAGGGGTTG    3000
AAGCCGTTGT ACGAGATGCA GGGAGCGCTG ATTAAACAAC TGGATGCGCA TAACGTTCGT    3060
CATAACGCGC CACAGCCAGA TTTGCAGAGC AAACTGGAAA CTCTGGATTT AGGCGAACAT    3120
GGCGCAGAAT TGCTTAACGA CATGAAGCGC TTCCGCGACG AACTGGAGCA GAGTGCAACC    3180
CGTTCGGTGA CCGTTTTAGG TCAACATCAG GGAGTGCTAA AAAGCAACGG TGAAATAAAT    3240
AGCGAATTTA AGCCATCGCC CGGCAAGGCG TTGGTCCAGA GCTTTAACGT CAATCGCTCT    3300
GGTCAGGATC TAAGCAAGTC ACTGCAACAG GCAGTACATG CCACGCCGCC ATCCGCAGAG    3360
AGTAAACTGC AATCCATGCT GGGGCACTTT GTCAGTGCCG GGGTGGATAT GAGTCATCAG    3420
AAGGGCGAGA TCCCGCTGGG CCGCCAGCGC GATCCGAATG ATAAAAACCGC ACTGACCAAA   3480
TCGCGTTTAA TTTTAGATAC CGTGACCATC GGTGAACTGC ATGAACTGGC CGATAAGGCG    3540
AAACTGGTAT CTGACCATAA ACCCGATGCC GATCAGATAA AACAGCTGCG CCAGCAGTTC    3600
GATACGCTGC GTGAAAAGCG GTATGAGAGC AATCCGGTGA AGCATTACAC CGATATGGGC    3660
TTCACCCATA ATAAGGCGCT GGAAGCAAAC TATGATGCGG TCAAAGCCTT TATCAATGCC    3720
TTTAAGAAAG AGCACCACGG CGTCAATCTG ACCACGCGTA CCGTACTGGA ATCACAGGGC    3780
AGTGCGGAGC TGGCGAAGAA GCTCAAGAAT ACGCTGTTGT CCCTGGACAG TGGTGAAAGT    3840
ATGAGCTTCA GCCGGTCATA TGGCGGGGGC GTCAGCACTG TCTTTGTGCC TACCCTTAGC    3900
AAGAAGGTGC CAGTTCCGGT GATCCCCGGA GCCGGCATCA CGCTGGATCG CGCCTATAAC    3960
CTGAGCTTCA GTCGTACCAG CGGCGGATTG AACGTCAGTT TTGGCCGCGA CGGCGGGGTG    4020
AGTGGTAACA TCATGGTCGC TACCGGCCAT GATGTGATGC CCTATATGAC CGGTAAGAAA    4080
ACCAGTGCAG GTAACGCCAG TGACTGGTTG AGCGCAAAAC ATAAAATCAG CCCGGACTTG    4140
```

-continued

```
CGTATCGGCG CTGCTGTGAG TGGCACCCTG CAAGGAACGC TACAAAACAG CCTGAAGTTT    4200

AAGCTGACAG AGGATGAGCT GCCTGGCTTT ATCCATGGCT TGACGCATGG CACGTTGACC    4260

CCGGCAGAAC TGTTGCAAAA GGGGATCGAA CATCAGATGA AGCAGGGCAG CAAACTGACG    4320

TTTAGCGTCG ATACCTCGGC AAATCTGGAT CTGCGTGCCG GTATCAATCT GAACGAAGAC    4380

GGCAGTAAAC CAAATGGTGT CACTGCCCGT GTTTCTGCCG GGCTAAGTGC ATCGGCAAAC    4440

CTGGCCGCCG GCTCGCGTGA ACGCAGCACC ACCTCTGGCC AGTTTGGCAG CACGACTTCG    4500

GCCAGCAATA ACCGCCCAAC CTTCCTCAAC GGGGTCGGCG CGGGTGCTAA CCTGACGGCT    4560

GCTTTAGGGG TTGCCCATTC ATCTACGCAT GAAGGGAAAC CGGTCGGGAT CTTCCCGGCA    4620

TTTACCTCGA CCAATGTTTC GGCAGCGCTG GCGCTGGATA ACCGTACCTC ACAGAGTATC    4680

AGCCTGGAAT TGAAGCGCGC GGAGCCGGTG ACCAGCAACG ATATCAGCGA GTTGACCTCC    4740

ACGCTGGGAA AACACTTTAA GGATAGCGCC ACAACGAAGA TGCTTGCCGC TCTCAAAGAG    4800

TTAGATGACG CTAAGCCCGC TGAACAACTG CATATTTTAC AGCAGCATTT CAGTGCAAAA    4860

GATGTCGTCG GTGATGAACG CTACGAGGCG GTGCGCAACC TGAAAAAACT GGTGATACGT    4920

CAACAGGCTG CGGACAGCCA CAGCATGGAA TTAGGATCTG CCAGTCACAG CACGACCTAC    4980

AATAATCTGT CGAGAATAAA TAATGACGGC ATTGTCGAGC TGCTACACAA ACATTTCGAT    5040

GCGGCATTAC CAGCAAGCAG TGCCAAACGT CTTGGTGAAA TGATGAATAA CGATCCGGCA    5100

CTGAAAGATA TTATTAAGCA GCTGCAAAGT ACGCCGTTCA GCAGCGCCAG CGTGTCGATG    5160

GAGCTGAAAG ATGGTCTGCG TGAGCAGACG GAAAAAGCAA TACTGGACGG TAAGGTCGGT    5220

CGTGAAGAAG TGGGAGTACT TTTCCAGGAT CGTAACAACT TGCGTGTTAA ATCGGTCAGC    5280

GTCAGTCAGT CCGTCAGCAA AAGCGAAGGC TTCAATACCC CAGCGCTGTT ACTGGGGACG    5340

AGCAACAGCG CTGCTATGAG CATGGAGCGC AACATCGGAA CCATTAATTT TAAATACGGC    5400

CAGGATCAGA ACACCCCACG GCGATTTACC CTGGAGGGTG GAATAGCTCA GGCTAATCCG    5460

CAGGTCGCAT CTGCGCTTAC TGATTTGAAG AAGGAAGGGC TGGAAATGAA GAGCTAA       5517
```

This DNA molecule is known as the dspE gene for *Erwinia amylovora*. This isolated DNA molecule of the present invention encodes a protein or polypeptide which elicits a plant pathogen's hypersensitive response having an amino acid sequence of SEQ ID NO: 28 as follows:

```
Met Glu Leu Lys Ser Leu Gly Thr Glu His Lys Ala Ala Val His Thr
1               5                   10                  15

Ala Ala His Asn Pro Val Gly His Gly Val Ala Leu Gln Gln Gly Ser
            20                  25                  30

Ser Ser Ser Ser Pro Gln Asn Ala Ala Ala Ser Leu Ala Ala Glu Gly
        35                  40                  45

Lys Asn Arg Gly Lys Met Pro Arg Ile His Gln Pro Ser Thr Ala Ala
    50                  55                  60

Asp Gly Ile Ser Ala Ala His Gln Gln Lys Lys Ser Phe Ser Leu Arg
65                  70                  75                  80

Gly Cys Leu Gly Thr Lys Lys Phe Ser Arg Ser Ala Pro Gln Gly Gln
                85                  90                  95

Pro Gly Thr Thr His Ser Lys Gly Ala Thr Leu Arg Asp Leu Leu Ala
            100                 105                 110

Arg Asp Asp Gly Glu Thr Gln His Glu Ala Ala Ala Pro Asp Ala Ala
        115                 120                 125

Arg Leu Thr Arg Ser Gly Gly Val Lys Arg Arg Asn Met Asp Asp Met
    130                 135                 140
```

-continued

```
Ala Gly Arg Pro Met Val Lys Gly Gly Ser Gly Glu Asp Lys Val Pro
145                 150                 155                 160

Thr Gln Gln Lys Arg His Gln Leu Asn Asn Phe Gly Gln Met Arg Gln
                165                 170                 175

Thr Met Leu Ser Lys Met Ala His Pro Ala Ser Ala Asn Ala Gly Asp
            180                 185                 190

Arg Leu Gln His Ser Pro Pro His Ile Pro Gly Ser His His Glu Ile
        195                 200                 205

Lys Glu Glu Pro Val Gly Ser Thr Ser Lys Ala Thr Thr Ala His Ala
    210                 215                 220

Asp Arg Val Glu Ile Ala Gln Glu Asp Asp Asp Ser Glu Phe Gln Gln
225                 230                 235                 240

Leu His Gln Gln Arg Leu Ala Arg Glu Arg Glu Asn Pro Pro Gln Pro
                245                 250                 255

Pro Lys Leu Gly Val Ala Thr Pro Ile Ser Ala Arg Phe Gln Pro Lys
            260                 265                 270

Leu Thr Ala Val Ala Glu Ser Val Leu Glu Gly Thr Asp Thr Thr Gln
        275                 280                 285

Ser Pro Leu Lys Pro Gln Ser Met Leu Lys Gly Ser Gly Ala Gly Val
    290                 295                 300

Thr Pro Leu Ala Val Thr Leu Asp Lys Gly Lys Leu Gln Leu Ala Pro
305                 310                 315                 320

Asp Asn Pro Pro Ala Leu Asn Thr Leu Leu Lys Gln Thr Leu Gly Lys
                325                 330                 335

Asp Thr Gln His Tyr Leu Ala His His Ala Ser Ser Asp Gly Ser Gln
            340                 345                 350

His Leu Leu Leu Asp Asn Lys Gly His Leu Phe Asp Ile Lys Ser Thr
        355                 360                 365

Ala Thr Ser Tyr Ser Val Leu His Asn Ser His Pro Gly Glu Ile Lys
    370                 375                 380

Gly Lys Leu Ala Gln Ala Gly Thr Gly Ser Val Ser Val Asp Gly Lys
385                 390                 395                 400

Ser Gly Lys Ile Ser Leu Gly Ser Gly Thr Gln Ser His Asn Lys Thr
                405                 410                 415

Met Leu Ser Gln Pro Gly Glu Ala His Arg Ser Leu Leu Thr Gly Ile
            420                 425                 430

Trp Gln His Pro Ala Gly Ala Ala Arg Pro Gln Gly Glu Ser Ile Arg
        435                 440                 445

Leu His Asp Asp Lys Ile His Ile Leu His Pro Glu Leu Gly Val Trp
    450                 455                 460

Gln Ser Ala Asp Lys Asp Thr His Ser Gln Leu Ser Arg Gln Ala Asp
465                 470                 475                 480

Gly Lys Leu Tyr Ala Leu Lys Asp Asn Arg Thr Leu Gln Asn Leu Ser
                485                 490                 495

Asp Asn Lys Ser Ser Glu Lys Leu Val Asp Lys Ile Lys Ser Tyr Ser
            500                 505                 510

Val Asp Gln Arg Gly Gln Val Ala Ile Leu Thr Asp Thr Pro Gly Arg
        515                 520                 525
```

-continued

```
His Lys Met Ser Ile Met Pro Ser Leu Asp Ala Ser Pro Glu Ser His
    530                 535                 540

Ile Ser Leu Ser Leu His Phe Ala Asp Ala His Gln Gly Leu Leu His
545                 550                 555                 560

Gly Lys Ser Glu Leu Glu Ala Gln Ser Val Ala Ile Ser His Gly Arg
                565                 570                 575

Leu Val Val Ala Asp Ser Glu Gly Lys Leu Phe Ser Ala Ala Ile Pro
            580                 585                 590

Lys Gln Gly Asp Gly Asn Glu Leu Lys Met Lys Ala Met Pro Gln His
        595                 600                 605

Ala Leu Asp Glu His Phe Gly His Asp His Gln Ile Ser Gly Phe Phe
    610                 615                 620

His Asp Asp His Gly Gln Leu Asn Ala Leu Val Lys Asn Asn Phe Arg
625                 630                 635                 640

Gln Gln His Ala Cys Pro Leu Gly Asn Asp His Gln Phe His Pro Gly
                645                 650                 655

Trp Asn Leu Thr Asp Ala Leu Val Ile Asp Asn Gln Leu Gly Leu His
            660                 665                 670

His Thr Asn Pro Glu Pro His Glu Ile Leu Asp Met Gly His Leu Gly
        675                 680                 685

Ser Leu Ala Leu Gln Glu Gly Lys Leu His Tyr Phe Asp Gln Leu Thr
    690                 695                 700

Lys Gly Trp Thr Gly Ala Glu Ser Asp Cys Lys Gln Leu Lys Lys Gly
705                 710                 715                 720

Leu Asp Gly Ala Ala Tyr Leu Leu Lys Asp Gly Glu Val Lys Arg Leu
                725                 730                 735

Asn Ile Asn Gln Ser Thr Ser Ser Ile Lys His Gly Thr Glu Asn Val
            740                 745                 750

Phe Ser Leu Pro His Val Arg Asn Lys Pro Glu Pro Gly Asp Ala Leu
        755                 760                 765

Gln Gly Leu Asn Lys Asp Asp Lys Ala Gln Ala Met Ala Val Ile Gly
    770                 775                 780

Val Asn Lys Tyr Leu Ala Leu Thr Glu Lys Gly Asp Ile Arg Ser Phe
785                 790                 795                 800

Gln Ile Lys Pro Gly Thr Gln Gln Leu Glu Arg Pro Ala Gln Thr Leu
                805                 810                 815

Ser Arg Glu Gly Ile Ser Gly Glu Leu Lys Asp Ile His Val Asp His
            820                 825                 830

Lys Gln Asn Leu Tyr Ala Leu Thr His Glu Gly Glu Val Phe His Gln
        835                 840                 845

Pro Arg Glu Ala Trp Gln Asn Gly Ala Glu Ser Ser Ser Trp His Lys
    850                 855                 860

Leu Ala Leu Pro Gln Ser Glu Ser Lys Leu Lys Ser Leu Asp Met Ser
865                 870                 875                 880

His Glu His Lys Pro Ile Ala Thr Phe Glu Asp Gly Ser Gln His Gln
                885                 890                 895

Leu Lys Ala Gly Gly Trp His Ala Tyr Ala Ala Pro Glu Arg Gly Pro
            900                 905                 910

Leu Ala Val Gly Thr Ser Gly Ser Gln Thr Val Phe Asn Arg Leu Met
        915                 920                 925

Gln Gly Val Lys Gly Lys Val Ile Pro Gly Ser Gly Leu Thr Val Lys
    930                 935                 940

Leu Ser Ala Gln Thr Gly Gly Met Thr Gly Ala Glu Gly Arg Lys Val
945                 950                 955                 960
```

-continued

```
Ser Ser Lys Phe Ser Glu Arg Ile Arg Ala Tyr Ala Phe Asn Pro Thr
                965                 970                 975

Met Ser Thr Pro Arg Pro Ile Lys Asn Ala Ala Tyr Ala Thr Gln His
            980                 985                 990

Gly Trp Gln Gly Arg Glu Gly Leu Lys Pro Leu Tyr Glu Met Gln Gly
        995                 1000                1005

Ala Leu Ile Lys Gln Leu Asp Ala His Asn Val Arg His Asn Ala Pro
    1010                1015                1020

Gln Pro Asp Leu Gln Ser Lys Leu Glu Thr Leu Asp Leu Gly Glu His
1025                1030                1035                1040

Gly Ala Glu Leu Leu Asn Asp Met Lys Arg Phe Arg Asp Glu Leu Glu
                1045                1050                1055

Gln Ser Ala Thr Arg Ser Val Thr Val Leu Gly Gln His Gln Gly Val
            1060                1065                1070

Leu Lys Ser Asn Gly Glu Ile Asn Ser Glu Phe Lys Pro Ser Pro Gly
        1075                1080                1085

Lys Ala Leu Val Gln Ser Phe Asn Val Asn Arg Ser Gly Gln Asp Leu
    1090                1095                1100

Ser Lys Ser Leu Gln Gln Ala Val His Ala Thr Pro Pro Ser Ala Glu
1105                1110                1115                1120

Ser Lys Leu Gln Ser Met Leu Gly His Phe Val Ser Ala Gly Val Asp
                1125                1130                1135

Met Ser His Gln Lys Gly Glu Ile Pro Leu Gly Arg Gln Arg Asp Pro
            1140                1145                1150

Asn Asp Lys Thr Ala Leu Thr Lys Ser Arg Leu Ile Leu Asp Thr val
        1155                1160                1165

Thr Ile Gly Glu Leu His Glu Leu Ala Asp Lys Ala Lys Leu Val Ser
    1170                1175                1180

Asp His Lys Pro Asp Ala Asp Gln Ile Lys Gln Leu Arg Gln Gln Phe
1185                1190                1195                1200

Asp Thr Leu Arg Glu Lys Arg Tyr Glu Ser Asn Pro Val Lys His Tyr
                1205                1210                1215

Thr Asp Met Gly Phe Thr His Asn Lys Ala Leu Glu Ala Asn Tyr Asp
            1220                1225                1230

Ala Val Lys Ala Phe Ile Asn Ala Phe Lys Lys Glu His His Gly Val
        1235                1240                1245

Asn Leu Thr Thr Arg Thr Val Leu Glu Ser Gln Gly Ser Ala Glu Leu
    1250                1255                1260

Ala Lys Lys Leu Lys Asn Thr Leu Leu Ser Leu Asp Ser Gly Glu Ser
1265                1270                1275                1280

Met Ser Phe Ser Arg Ser Tyr Gly Gly Gly Val Ser Thr Val Phe Val
                1285                1290                1295

Pro Thr Leu Ser Lys Lys Val Pro Val Pro Val Ile Pro Gly Ala Gly
            1300                1305                1310

Ile Thr Leu Asp Arg Ala Tyr Asn Leu Ser Phe Ser Arg Thr Ser Gly
        1315                1320                1325

Gly Leu Asn Val Ser Phe Gly Arg Asp Gly Gly Val Ser Gly Asn Ile
    1330                1335                1340

Met Val Ala Thr Gly His Asp Val Met Pro Tyr Met Thr Gly Lys Lys
1345                1350                1355                1360

Thr Ser Ala Gly Asn Ala Ser Asp Trp Leu Ser Ala Lys His Lys Ile
                1365                1370                1375

Ser Pro Asp Leu Arg Ile Gly Ala Ala Val Ser Gly Thr Leu Gln Gly
```

-continued

```
            1380                1385                1390

Thr Leu Gln Asn Ser Leu Lys Phe Lys Leu Thr Glu Asp Glu Leu Pro
        1395                1400                1405

Gly Phe Ile His Gly Leu Thr His Gly Thr Leu Thr Pro Ala Glu Leu
    1410                1415                1420

Leu Gln Lys Gly Ile Glu His Gln Met Lys Gln Gly Ser Lys Leu Thr
1425                1430                1435                1440

Phe Ser Val Asp Thr Ser Ala Asn Leu Asp Leu Arg Ala Gly Ile Asn
                1445                1450                1455

Leu Asn Glu Asp Gly Ser Lys Pro Asn Gly Val Thr Ala Arg Val Ser
            1460                1465                1470

Ala Gly Leu Ser Ala Ser Ala Asn Leu Ala Ala Gly Ser Arg Glu Arg
        1475                1480                1485

Ser Thr Thr Ser Gly Gln Phe Gly Ser Thr Thr Ser Ala Ser Asn Asn
    1490                1495                1500

Arg Pro Thr Phe Leu Asn Gly Val Gly Ala Gly Ala Asn Leu Thr Ala
1505                1510                1515                1520

Ala Leu Gly Val Ala His Ser Ser Thr His Glu Gly Lys Pro Val Gly
                1525                1530                1535

Ile Phe Pro Ala Phe Thr Ser Thr Asn Val Ser Ala Ala Leu Ala Leu
            1540                1545                1550

Asp Asn Arg Thr Ser Gln Ser Ile Ser Leu Glu Leu Lys Arg Ala Glu
        1555                1560                1565

Pro Val Thr Ser Asn Asp Ile Ser Glu Leu Thr Ser Thr Leu Gly Lys
    1570                1575                1580

His Phe Lys Asp Ser Ala Thr Thr Lys Met Leu Ala Ala Leu Lys Glu
1585                1590                1595                1600

Leu Asp Asp Ala Lys Pro Ala Glu Gln Leu His Ile Leu Gln Gln His
                1605                1610                1615

Phe Ser Ala Lys Asp Val Val Gly Asp Glu Arg Tyr Glu Ala Val Arg
            1620                1625                1630

Asn Leu Lys Lys Leu Val Ile Arg Gln Gln Ala Ala Asp Ser His Ser
        1635                1640                1645

Met Glu Leu Gly Ser Ala Ser His Ser Thr Thr Tyr Asn Asn Leu Ser
    1650                1655                1660

Arg Ile Asn Asn Asp Gly Ile Val Glu Leu Leu His Lys His Phe Asp
1665                1670                1675                1680

Ala Ala Leu Pro Ala Ser Ser Ala Lys Arg Leu Gly Glu Met Met Asn
                1685                1690                1695

Asn Asp Pro Ala Leu Lys Asp Ile Ile Lys Gln Leu Gln Ser Thr Pro
            1700                1705                1710

Phe Ser Ser Ala Ser Val Ser Met Glu Leu Lys Asp Gly Leu Arg Glu
        1715                1720                1725

Gln Thr Glu Lys Ala Ile Leu Asp Gly Lys Val Gly Arg Glu Glu val
    1730                1735                1740

Gly Val Leu Phe Gln Asp Arg Asn Asn Leu Arg Val Lys Ser Val Ser
1745                1750                1755                1760

Val Ser Gln Ser Val Ser Lys Ser Glu Gly Phe Asn Thr Pro Ala Leu
                1765                1770                1775

Leu Leu Gly Thr Ser Asn Ser Ala Ala Met Ser Met Glu Arg Asn Ile
            1780                1785                1790

Gly Thr Ile Asn Phe Lys Tyr Gly Gln Asp Gln Asn Thr Pro Arg Arg
        1795                1800                1805
```

-continued

```
Phe Thr Leu Glu Gly Gly Ile Ala Gln Ala Asn Pro Gln Val Ala Ser
    1810                1815                1820

Ala Leu Thr Asp Leu Lys Lys Glu Gly Leu Glu Met Lys Ser
1825                1830                1835
```

This protein or polypeptide is about 198 kDa and has a pI of 8.98.

The present invention relates to an isolated DNA molecule having a nucleotide sequence of SEQ ID NO: 29 as follows:

```
ATGACATCGT CACAGCAGCG GGTTGAAAGG TTTTTACAGT ATTTCTCCGC CGGGTGTAAA     60

ACGCCCATAC ATCTGAAAGA CGGGGTGTGC GCCCTGTATA ACGAACAAGA TGAGGAGGCG    120

GCGGTGCTGG AAGTACCGCA ACACAGCGAC AGCCTGTTAC TACACTGCCG AATCATTGAG    180

GCTGACCCAC AAACTTCAAT AACCCTGTAT TCGATGCTAT TACAGCTGAA TTTTGAAATG    240

GCGGCCATGC GCGGCTGTTG GCTGGCGCTG GATGAACTGC ACAACGTGCG TTTATGTTTT    300

CAGCAGTCGC TGGAGCATCT GGATGAAGCA AGTTTTAGCG ATATCGTTAG CGGCTTCATC    360

GAACATGCGG CAGAAGTGCG TGAGTATATA GCGCAATTAG ACGAGAGTAG CGCGGCATAA    420
```

This is known as the dspF gene. This isolated DNA molecule of the present invention encodes a hypersensitive response elicitor protein or polypeptide having an amino acid sequence of SEQ ID NO: 30 as follows:

```
Met Thr Ser Ser Gln Gln Arg Val Glu Arg Phe Leu Gln Tyr Phe Ser
1               5                   10                  15

Ala Gly Cys Lys Thr Pro Ile His Leu Lys Asp Gly Val Cys Ala Leu
            20                  25                  30

Tyr Asn Glu Gln Asp Glu Glu Ala Ala Val Leu Glu Val Pro Gln His
        35                  40                  45

Ser Asp Ser Leu Leu Leu His Cys Arg Ile Ile Glu Ala Asp Pro Gln
    50                  55                  60

Thr Ser Ile Thr Leu Tyr Ser Met Leu Leu Gln Leu Asn Phe Glu Met
65                  70                  75                  80

Ala Ala Met Arg Gly Cys Trp Leu Ala Leu Asp Glu Leu His Asn Val
                85                  90                  95

Arg Leu Cys Phe Gln Gln Ser Leu Glu His Leu Asp Glu Ala Ser Phe
            100                 105                 110

Ser Asp Ile Val Ser Gly Phe Ile Glu His Ala Ala Glu Val Arg Glu
        115                 120                 125

Tyr Ile Ala Gln Leu Asp Glu Ser Ser Ala Ala
    130                 135
```

This protein or polypeptide is about 16 kDa and has a pI of 4.45.

The hypersensitive response elicitor polypeptide or protein derived from *Pseudomonas syringae* has an amino acid sequence corresponding to SEQ ID NO: 31 as follows:

```
Met Gln Ser Leu Ser Leu Asn Ser Ser Ser Leu Gln Thr Pro Ala Met
1               5                   10                  15

Ala Leu Val Leu Val Arg Pro Glu Ala Glu Thr Thr Gly Ser Thr Ser
            20                  25                  30

Ser Lys Ala Leu Gln Glu Val Val Val Lys Leu Ala Glu Glu Leu Met
        35                  40                  45

Arg Asn Gly Gln Leu Asp Asp Ser Ser Pro Leu Gly Lys Leu Leu Ala
    50                  55                  60

Lys Ser Met Ala Ala Asp Gly Lys Ala Gly Gly Gly Ile Glu Asp Val
65                  70                  75                  80

Ile Ala Ala Leu Asp Lys Leu Ile His Glu Lys Leu Gly Asp Asn Phe
                85                  90                  95

Gly Ala Ser Ala Asp Ser Ala Ser Gly Thr Gly Gln Gln Asp Leu Met
            100                 105                 110

Thr Gln Val Leu Asn Gly Leu Ala Lys Ser Met Leu Asp Asp Leu Leu
        115                 120                 125

Thr Lys Gln Asp Gly Gly Thr Ser Phe Ser Glu Asp Asp Met Pro Met
    130                 135                 140

Leu Asn Lys Ile Ala Gln Phe Met Asp Asp Asn Pro Ala Gln Phe Pro
145                 150                 155                 160

Lys Pro Asp Ser Gly Ser Trp Val Asn Glu Leu Lys Glu Asp Asn Phe
                165                 170                 175

Leu Asp Gly Asp Glu Thr Ala Ala Phe Arg Ser Ala Leu Asp Ile Ile
            180                 185                 190

Gly Gln Gln Leu Gly Asn Gln Gln Ser Asp Ala Gly Ser Leu Ala Gly
        195                 200                 205

Thr Gly Gly Gly Leu Gly Thr Pro Ser Ser Phe Ser Asn Asn Ser Ser
    210                 215                 220

Val Met Gly Asp Pro Leu Ile Asp Ala Asn Thr Gly Pro Gly Asp Ser
225                 230                 235                 240

Gly Asn Thr Arg Gly Glu Ala Gly Gln Leu Ile Gly Glu Leu Ile Asp
                245                 250                 255

Arg Gly Leu Gln Ser Val Leu Ala Gly Gly Gly Leu Gly Thr Pro Val
            260                 265                 270

Asn Thr Pro Gln Thr Gly Thr Ser Ala Asn Gly Gly Gln Ser Ala Gln
        275                 280                 285

Asp Leu Asp Gln Leu Leu Gly Gly Leu Leu Leu Lys Gly Leu Glu Ala
    290                 295                 300

Thr Leu Lys Asp Ala Gly Gln Thr Gly Thr Asp Val Gln Ser Ser Ala
305                 310                 315                 320

Ala Gln Ile Ala Thr Leu Leu Val Ser Thr Leu Leu Gln Gly Thr Arg
                325                 330                 335

Asn Gln Ala Ala Ala
            340
```

This hypersensitive response elicitor polypeptide or protein has a molecular weight of 34–35 kDa It is rich in glycine (about 13.5%) and lacks cysteine and tyrosine. Further information about the hypersensitive response elicitor derived from *Pseudomonas syringae* is found in He, S. Y., H. C. Huang, and A. Collmer, "*Pseudomonas syringae* pv. syringae Harpin$_{Pss}$: a Protein that is Secreted via the Hrp Pathway and Elicits the Hypersensitive Response in Plants," *Cell* 73:1255–1266 (1993), which is hereby incorporated by reference. The DNA molecule encoding the hypersensitive response elicitor from *Pseudomonas syringae* has a nucleotide sequence corresponding to SEQ ID NO: 32 as follows:

```
ATGCAGAGTC TCAGTCTTAA CAGCAGCTCG CTGCAAACCC CGGCAATGGC CCTTGTCCTG      60
GTACGTCCTG AAGCCGAGAC GACTGGCAGT ACGTCGAGCA AGGCGCTTCA GGAAGTTGTC     120
GTGAAGCTGG CCGAGGAACT GATGCGCAAT GGTCAACTCG ACGACAGCTC GCCATTGGGA     180
AAACTGTTGG CCAAGTCGAT GGCCGCAGAT GGCAAGGCGG GCGGCGGTAT TGAGGATGTC     240
ATCGCTGCGC TGGACAAGCT GATCCATGAA AAGCTCGGTG ACAACTTCGG CGCGTCTGCG     300
GACAGCGCCT CGGGTACCGG ACAGCAGGAC CTGATGACTC AGGTGCTCAA TGGCCTGGCC     360
AAGTCGATGC TCGATGATCT TCTGACCAAG CAGGATGGCG GGACAAGCTT CTCCGAAGAC     420
GATATGCCGA TGCTGAACAA GATCGCGCAG TTCATGGATG ACAATCCCGC ACAGTTTCCC     480
AAGCCGGACT CGGGCTCCTG GGTGAACGAA CTCAAGGAAG ACAACTTCCT TGATGGCGAC     540
GAAACGGCTG CGTTCCGTTC GGCACTCGAC ATCATTGGCC AGCAACTGGG TAATCAGCAG     600
AGTGACGCTG GCAGTCTGGC AGGGACGGGT GGAGGTCTGG GCACTCCGAG CAGTTTTTCC     660
AACAACTCGT CCGTGATGGG TGATCCGCTG ATCGACGCCA ATACCGGTCC CGGTGACAGC     720
GGCAATACCC GTGGTGAAGC GGGGCAACTG ATCGGCGAGC TTATCGACCG TGGCCTGCAA     780
TCGGTATTGG CCGGTGGTGG ACTGGGCACA CCCGTAAACA CCCCGCAGAC CGGTACGTCG     840
GCGAATGGCG GACAGTCCGC TCAGGATCTT GATCAGTTGC TGGGCGGCTT GCTGCTCAAG     900
GGCCTGGAGG CAACGCTCAA GGATGCCGGG CAAACAGGCA CCGACGTGCA GTCGAGCGCT     960
GCGCAAATCG CCACCTTGCT GGTCAGTACG CTGCTGCAAG GCACCCGCAA TCAGGCTGCA    1020
GCCTGA                                                               1026
```

Another potentially suitable hypersensitive response elicitor from *Pseudomonas syningae* is disclosed in U.S. patent application Ser. No. 09/120,817, which is hereby incorporated by reference. The protein has a nucleotide sequence of SEQ ID NO: 33 as follows:

```
TCCACTTCGC TGATTTTGAA ATTGGCAGAT TCATAGAAAC GTCCAGGTGT GGAAATCAGG      60
CTGAGTGCGC AGATTTCGTT GATAAGGGTG TGGTACTGGT CATTGTTGGT CATTTCAAGG     120
CCTCTGAGTG CGGTGCGGAG CAATACCAGT CTTCCTGCTG GCGTGTGCAC ACTGAGTCGC     180
AGGCATAGGC ATTTCAGTTC CTTGCGTTGG TTGGGCATAT AAAAAAAGGA ACTTTTAAAA     240
ACAGTGCAAT GAGATGCCGG CAAAACGGGA ACCGGTCGCT GCGCTTTGCC ACTCACTTCG     300
AGCAAGCTCA ACCCCAAACA TCCACATCCC TATCGAACGG ACAGCGATAC GGCCACTTGC     360
TCTGGTAAAC CCTGGAGCTG GCGTCGGTCC AATTGCCCAC TTAGCGAGGT AACGCAGCAT     420
GAGCATCGGC ATCACACCCC GGCCGCAACA GACCACCACG CCACTCGATT TTTCGGCGCT     480
AAGCGGCAAG AGTCCTCAAC CAAACACGTT CGGCGAGCAG AACACTCAGC AAGCGATCGA     540
CCCGAGTGCA CTGTTGTTCG GCAGCGACAC ACAGAAAGAC GTCAACTTCG GCACGCCCGA     600
CAGCACCGTC CAGAATCCGC AGGACGCCAG CAAGCCCAAC GACAGCCAGT CCAACATCGC     660
TAAATTGATC AGTGCATTGA TCATGTCGTT GCTGCAGATG CTCACCAACT CCAATAAAAA     720
GCAGGACACC AATCAGGAAC AGCCTGATAG CCAGGCTCCT TTCCAGAACA ACGGCGGGCT     780
CGGTACACCG TCGGCCGATA GCGGGGGCGG CGGTACACCG GATGCGACAG GTGGCGGCGG     840
CGGTGATACG CCAAGCGCAA CAGGCGGTGG CGGCGGTGAT ACTCCGACCG CAACAGGCGG     900
TGGCGGCAGC GGTGGCGGCG GCACACCCAC TGCAACAGGT GGCGGCAGCG GTGGCACACC     960
CACTGCAACA GGCGGTGGCG AGGGTGGCGT AACACCGCAA ATCACTCCGC AGTTGGCCAA    1020
CCCTAACCGT ACCTCAGGTA CTGGCTCGGT GTCGGACACC GCAGGTTCTA CCGAGCAAGC    1080
```

-continued

```
CGGCAAGATC AATGTGGTGA AAGACACCAT CAAGGTCGGC GCTGGCGAAG TCTTTGACGG    1140

CCACGGCGCA ACCTTCACTG CCGACAAATC TATGGGTAAC GGAGACCAGG GCGAAAATCA    1200

GAAGCCCATG TTCGAGCTGG CTGAAGGCGC TACGTTGAAG AATGTGAACC TGGGTGAGAA    1260

CGAGGTCGAT GGCATCCACG TGAAAGCCAA AAACGCTCAG GAAGTCACCA TTGACAACGT    1320

GCATGCCCAG AACGTCGGTG AAGACCTGAT TACGGTCAAA GGCGAGGGAG GCGCAGCGGT    1380

CACTAATCTG AACATCAAGA ACAGCAGTGC CAAAGGTGCA GACGACAAGG TTGTCCAGCT    1440

CAACGCCAAC ACTCACTTGA AAATCGACAA CTTCAAGGCC GACGATTTCG GCACGATGGT    1500

TCGCACCAAC GGTGGCAAGC AGTTTGATGA CATGAGCATC GAGCTGAACG GCATCGAAGC    1560

TAACCACGGC AAGTTCGCCC TGGTGAAAAG CGACAGTGAC GATCTGAAGC TGGCAACGGG    1620

CAACATCGCC ATGACCGACG TCAAACACGC CTACGATAAA ACCCAGGCAT CGACCCAACA    1680

CACCGAGCTT TGAATCCAGA CAAGTAGCTT GAAAAAAGGG GGTGGACTC                1729
```

This DNA molecule is known as the dspE gene for *Pseudomonas syringae*. This isolated DNA molecule of the present invention encodes a protein or polypeptide which elicits a plant pathogen's hypersensitive response having an amino acid sequence of SEQ ID NO: 34 as follows:

```
Met Ser Ile Gly Ile Thr Pro Arg Pro Gln Gln Thr Thr Thr Pro Leu
1               5                   10                  15

Asp Phe Ser Ala Leu Ser Gly Lys Ser Pro Gln Pro Asn Thr Phe Gly
            20                  25                  30

Glu Gln Asn Thr Gln Gln Ala Ile Asp Pro Ser Ala Leu Leu Phe Gly
        35                  40                  45

Ser Asp Thr Gln Lys Asp Val Asn Phe Gly Thr Pro Asp Ser Thr Val
    50                  55                  60

Gln Asn Pro Gln Asp Ala Ser Lys Pro Asn Asp Ser Gln Ser Asn Ile
65                  70                  75                  80

Ala Lys Leu Ile Ser Ala Leu Ile Met Ser Leu Leu Gln Met Leu Thr
                85                  90                  95

Asn Ser Asn Lys Lys Gln Asp Thr Asn Gln Glu Gln Pro Asp Ser Gln
            100                 105                 110

Ala Pro Phe Gln Asn Asn Gly Gly Leu Gly Thr Pro Ser Ala Asp Ser
        115                 120                 125

Gly Gly Gly Gly Thr Pro Asp Ala Thr Gly Gly Gly Gly Gly Asp Thr
    130                 135                 140

Pro Ser Ala Thr Gly Gly Gly Gly Gly Asp Thr Pro Thr Ala Thr Gly
145                 150                 155                 160

Gly Gly Gly Ser Gly Gly Gly Gly Thr Pro Thr Ala Thr Gly Gly Gly
                165                 170                 175

Ser Gly Gly Thr Pro Thr Ala Thr Gly Gly Gly Glu Gly Gly Val Thr
            180                 185                 190

Pro Gln Ile Thr Pro Gln Leu Ala Asn Pro Asn Arg Thr Ser Gly Thr
        195                 200                 205

Gly Ser Val Ser Asp Thr Ala Gly Ser Thr Glu Gln Ala Gly Lys Ile
    210                 215                 220

Asn Val Val Lys Asp Thr Ile Lys Val Gly Ala Gly Glu Val Phe Asp
225                 230                 235                 240

Gly His Gly Ala Thr Phe Thr Ala Asp Lys Ser Met Gly Asn Gly Asp
                245                 250                 255

Gln Gly Glu Asn Gln Lys Pro Met Phe Glu Leu Ala Glu Gly Ala Thr
            260                 265                 270
```

-continued

```
Leu Lys Asn Val Asn Leu Gly Glu Asn Glu Val Asp Gly Ile His Val
        275                 280                 285

Lys Ala Lys Asn Ala Gln Glu Val Thr Ile Asp Asn Val His Ala Gln
    290                 295                 300

Asn Val Gly Glu Asp Leu Ile Thr Val Lys Gly Glu Gly Gly Ala Ala
305                 310                 315                 320

Val Thr Asn Leu Asn Ile Lys Asn Ser Ser Ala Lys Gly Ala Asp Asp
            325                 330                 335

Lys Val Val Gln Leu Asn Ala Asn Thr His Leu Lys Ile Asp Asn Phe
            340                 345                 350

Lys Ala Asp Asp Phe Gly Thr Met Val Arg Thr Asn Gly Gly Lys Gln
        355                 360                 365

Phe Asp Asp Met Ser Ile Glu Leu Asn Gly Ile Glu Ala Asn His Gly
    370                 375                 380

Lys Phe Ala Leu Val Lys Ser Asp Ser Asp Asp Leu Lys Leu Ala Thr
385                 390                 395                 400

Gly Asn Ile Ala Met Thr Asp Val Lys His Ala Tyr Asp Lys Thr Gln
            405                 410                 415

Ala Ser Thr Gln His Thr Glu Leu
            420
```

This protein or polypeptide is about 43.9 kDa.

The hypersensitive response elicitor polypeptide or protein derived from *Pseudomonas solanacearum* has an amino acid sequence corresponding to SEQ ID NO: 35 as follows:

```
Met Ser Val Gly Asn Ile Gln Ser Pro Ser Asn Leu Pro Gly Leu Gln
1               5                   10                  15

Asn Leu Asn Leu Asn Thr Asn Thr Asn Ser Gln Gln Ser Gly Gln Ser
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly Asn Thr Gly
    50                  55                  60

Asn Thr Gly Asn Ala Pro Ala Lys Asp Gly Asn Ala Asn Ala Gly Ala
65                  70                  75                  80

Asn Asp Pro Ser Lys Asn Asp Pro Ser Lys Ser Gln Ala Pro Gln Ser
                85                  90                  95

Ala Asn Lys Thr Gly Asn Val Asp Asp Ala Asn Asn Gln Asp Pro Met
            100                 105                 110

Gln Ala Leu Met Gln Leu Leu Glu Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gly Gln Gly Gly Leu Ala
145                 150                 155                 160

Glu Ala Leu Gln Glu Ile Glu Gln Ile Leu Ala Gln Leu Gly Gly Gly
                165                 170                 175

Gly Ala Gly Ala Gly Gly Ala Gly Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205

Asp Gly Gly Asn Gly Val Asn Gly Asn Gln Ala Asn Gly Pro Gln Asn
    210                 215                 220
```

-continued

```
Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
                245                 250                 255

Ala Leu Val Gln Met Met Gln Gln Gly Gly Leu Gly Gly Gly Asn Gln
            260                 265                 270

Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
    290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
                325                 330                 335

Gln Ser Thr Ser Thr Gln Pro Met
            340
```

It is encoded by a DNA molecule having a nucleotide sequence corresponding to SEQ ID NO: 36 as follows:

```
ATGTCAGTCG GAAACATCCA GAGCCCGTCG AACCTCCCGG GTCTGCAGAA CCTGAACCTC      60

AACACCAACA CCAACAGCCA GCAATCGGGC CAGTCCGTGC AAGACCTGAT CAAGCAGGTC     120

GAGAAGGACA TCCTCAACAT CATCGCAGCC CTCGTGCAGA AGGCCGCACA GTCGGCGGGC     180

GGCAACACCG GTAACACCGG CAACGCGCCG GCGAAGGACG GCAATGCCAA CGCGGGCGCC     240

AACGACCCGA GCAAGAACGA CCCGAGCAAG AGCCAGGCTC CGCAGTCGGC CAACAAGACC     300

GGCAACGTCG ACGACGCCAA CAACCAGGAT CCGATGCAAG CGCTGATGCA GCTGCTGGAA     360

GACCTGGTGA AGCTGCTGAA GGCGGCCCTG CACATGCAGC AGCCCGGCGG CAATGACAAG     420

GGCAACGGCG TGGGCGGTGC CAACGGCGCC AAGGGTGCCG GCGGCCAGGG CGGCCTGGCC     480

GAAGCGCTGC AGGAGATCGA GCAGATCCTC GCCCAGCTCG GCGGCGGCGG TGCTGGCGCC     540

GGCGGCGCGG GTGGCGGTGT CGGCGGTGCT GGTGGCGCGG ATGGCGGCTC CGGTGCGGGT     600

GGCGCAGGCG GTGCGAACGG CGCCGACGGC GGCAATGGCG TGAACGGCAA CCAGGCGAAC     660

GGCCCGCAGA ACGCAGGCGA TGTCAACGGT GCCAACGGCG CGGATGACGG CAGCGAAGAC     720

CAGGGCGGCC TCACCGGCGT GCTGCAAAAG CTGATGAAGA TCCTGAACGC GCTGGTGCAG     780

ATGATGCAGC AAGGCGGCCT CGGCGGCGGC AACCAGGCGC AGGGCGGCTC GAAGGGTGCC     840

GGCAACGCCT CGCCGGCTTC CGGCGCGAAC CCGGGCGCGA ACCAGCCCGG TTCGGCGGAT     900

GATCAATCGT CCGGCCAGAA CAATCTGCAA TCCCAGATCA TGGATGTGGT GAAGGAGGTC     960

GTCCAGATCC TGCAGCAGAT GCTGGCGGCG CAGAACGGCG GCAGCCAGCA GTCCACCTCG    1020

ACGCAGCCGA TGTAA                                                     1035
```

Further information regarding the hypersensitive response elicitor polypeptide or protein derived from *Pseudomonas solanacearum* is set forth in Arlat, M., F. Van Gijsegem, J. C. Huet, J. C. Pemollet, and C. A. Boucher, "PopA I, a Protein which Induces a Hypersensitive-like Response in Specific Petunia Genotypes, is Secreted via the Hrp Pathway of *Pseudomonas solanacearum*," *EMBO J.* 13:543–533 (1994), which is hereby incorporated by reference.

The hypersensitive response elicitor polypeptide or protein from *Xanthomonas campestris* pv. glycines has an amino acid sequence corresponding to SEQ ID NO: 37 as follows:

```
Thr Leu Ile Glu Leu Met Ile Val Val Ala Ile Ile Ala Ile Leu Ala
1               5                   10                  15

Ala Ile Ala Leu Pro Ala Tyr Gln Asp Tyr
            20                  25
```

This sequence is an amino terminal sequence having only 26 residues from the hypersensitive response elicitor polypeptide or protein of *Xanthomonas campestris* pv. glycines. It matches with fimbrial subunit proteins determined in other *Xanthomonas campestris* pathovars.

The hypersensitive response elicitor polypeptide or protein from *Xanthomonas campestris* pv. pelargonii is heat stable, protease sensitive, and has a molecular weight of 20 kDa. It includes an amino acid sequence corresponding to SEQ ID NO: 38 as follows:

```
Ser Ser Gln Gln Ser Pro Ser Ala Gly Ser Glu Gln Gln Leu Asp Gln
1               5                   10                  15

Leu Leu Ala Met
            20
```

Isolation of *Erwinia carotovora hypersensitve response elictor protein or polypeptide is described in Cui et al., "The Rsm Mutants of Erwinia carotovora* subsp. carotovora Strain Ecc71 Overexpress hro $N_{Ecc}$ and Elicit a Hypersensitive Reason-like Response is Tobacco Leaves, " *MPMI*, 9(7) :563 . 73)1996), which is hereby incorporated by reference. The hypersensitve response elicitor protein or polypeptide of *Erwinia stewartii* is set forth in Ahmad et al., "Harpin is Not Necessary for the Pathogenicity of *Erwinia stewartii* on Maize," *8th Int'l. Cong. Molec. Plant-Microbe Interact*., Jul. 14–19, 1996 and Ahmad, et al., "Harpin is Not Necessary for the Pathogenicity of *Erwinia stewartii* on Maize," *Ann. Mtg. Am. Phytopath. Soc*., Jul. 27–31, 1996, which are hereby incorporated by reference.

Hypersensitive response elicitor proteins or polypeptides from *Phytophthoraparasitica, Phytophthora cryptogea, Phytophihora cinnamoni, Phytophthora capsici, Phytophthora megasperma*, and *Phytophora citrophthora* are described in Karnan, et al., "Extracellular Protein Elicitors from Phytophthora: Most Specificity and Induction of Resistance to Bacterial and Fungal Phytopathogens," *Molec. Plant-Microbe Interact*., 6(1):15–25 (1993), Ricci et al., "Structure and Activity of Proteins from Pathogenic Fungi Phytophthora Eliciting Necrosis and Acquired Resistance in Tobacco," *Eur. J. Biochem*., 183:555–63 (1989), Ricci et al., "Differential Production of Parasiticein, and Elicitor of Necrosis and Resistance in Tobacco, by Isolates of *Phytophthora parasitica," Plant Path*. 41:298–307 (1992), Baillreul et al, "A New Elicitor of the Hypersensitive Response in Tobacco: A Fungal Glycoprotein Elicits Cell Death, Expression of Defence Genes, Production of Salicylic Acid, and Induction of Systemic Acquired Resistance," *Plant J*., 8(4) :551–60 (1995), and Bonnet et al., "Acquired Resistance Triggered by Elicitors in Tobacco and Other Plants," *Eur. J. Plant Path*., 102:181–92 (1996), which are hereby incorporated by reference.

Another hypersensitive response elicitor in accordance with the present invention is from *Clavibacter michiganensis* subsp. *sepedonicus* which is fully described in U.S. patent application Ser. No. 09/136,625, which is hereby incorporated by reference.

The above elicitors are exemplary. Other elicitors can be identified by growing fungi or bacteria that elicit a hypersensitive response under conditions which genes encoding an elicitor are expressed. Cell-free preparations from culture supernatants can be tested for elicitor activity (i.e. local necrosis) by using them to infiltrate appropriate plant tissues.

Fragments of the above hypersensitive response elicitor polypeptides or proteins as well as fragments of full length elicitors from other pathogens are encompassed by the present invention.

Suitable fragments can be produced by several means. In the first, subclones of the gene encoding a known elicitor protein are produced by conventional molecular genetic manipulation by subcloning gene fragments. The subclones then are expressed in vitro or in vivo in bacterial cells to yield a smaller protein or peptide that can be tested for elicitor activity according to the procedure described below.

As an alternative, fragments of an elicitor protein can be produced by digestion of a full-length elicitor protein with proteolytic enzymes like chymotrypsin or Staphylococcus proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for expression of a truncated peptide or protein.

Chemical synthesis can also be used to make suitable fragments. Such a synthesis is carried out using known amino acid sequences for the elicitor being produced. Alternatively, subjecting a full length elicitor to high temperatures and pressures will produce fragments. These fragments can then be separated by conventional procedures (e.g., chromatography, SDS-PAGE).

An example of suitable fragments of a hypersensitive response elicitor which do not elicit a hypersensitive response include fragments of the *Erwinia amylovora* hypersensitive response elicitor. Suitable fragments include a C-terminal fragment of the amino acid sequence of SEQ ID NO: 23, an N-terminal fragment of the amino acid sequence of SEQ ID NO: 23, or an internal fragment of the amino acid sequence of SEQ ID NO: 23. The C-terminal fragment of the amino acid sequence of SEQ ID NO: 23 can span the Following amino acids of SEQ ID NO: 23: 169 and 403, 210 and 403, 267 and 403, or 343 and 403. The internal fragment of the amino acid sequence of SEQ ID NO: 23 can span the following amino acids of SEQ ID NO: 23: 150 and 179, 137 and 166, 121 and 150, 76 and 168, 105 and 168, or 137 and 156. Other suitable fragments can be identified in accordance with the present invention.

Another example of a useful fragment of a hypersensitive response elicitor which fragment does not itself elicit a hypersensitive response is the protein fragment containing amino acids 190 to 294 of the amino acid sequence (SEQ ID NO: 31) for the *Pseudomonas syringae* pv. syringae hypersensitive response elicitor. This fragment is useful in imparting disease resistance and enhancing plant growth.

Yet another example of a useful fragment of a hypersensitive response elicitor is the peptide having an amino acid sequence corresponding to SEQ ID NO: 39. This peptide is derived from the hypersensitive response eliciting glycoprotein of *Phytophthora megasperma* and enhances plant growth.

Variants may be made by, for example, the deletion or addition of amino acids that have minimal influence on the properties, secondary structure, and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The fragment of the present invention is preferably in isolated form (i.e. separated from its host organism) and more preferably produced in purified form (preferably at least about 60%, more preferably 80%, pure) by conventional techniques. Typically, the fragment of the present invention is produced but not secreted into the growth medium of recombinant host cells. Alternatively, the protein or polypeptide of the present invention is secreted into growth medium. In the case of unsecreted protein, to isolate the protein fragment, the host cell (e.g., *E. coli*) carrying a recombinant plasmid is propagated, lysed by sonication, heat, or chemical treatment, and the homogenate is centrifuged to remove bacterial debris. The supernatant is then subjected to heat treatment and the fragment is separated by centriugation. The supernatant fraction containing the fragment is subjected to gel filtration in an appropriately sized dextran or polyacrylamide column to separate the fragment. If necessary, the protein fraction may be further purified by ion exchange or HPLC.

The DNA molecule encoding the fragment of the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system, and, further, procaryotic promotors are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in *E. coli*, its bacteriophages, or plasmids, promoters such as the T7 phage promotor, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coil* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coil* tryptophan E, D, C, B or A genes. Additionally, any SD-ATG combination produced by recombinant DNA or other techniques involving incorporation of synthetic nucleotides may be used.

Once the isolated DNA molecule encoding the fragment of a hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention further relates to methods of imparting disease resistance to plants, enhancing plant growth, and/or effecting insect control for plants These methods involve applying the fragment of a hypersensitive response elicitor polypeptide or protein which does not elicit a hypersensitive response in a non-infectious form to all or part of a plant or a plant seed under conditions effective for the fragment to impart disease resistance, enhance growth, and/or control insects. Alternatively, these fragments of a hypersensitive response elicitor protein or polypeptide can be applied to plants such that seeds recovered from such plants themselves are able to impart disease resistance in plants, to enhance plant growth, and/or to effect insect control.

As an alternative to applying a fragment of a hypersensitive response elicitor polypeptide or protein to plants or plant seeds in order to impart disease resistance in plants, to effect plant growth, and/,or to control insects on the plants or plants grown from the seeds, transgenic plants or plant seeds can be utilized. When utilizing transgenic plants, this involves providing a transgenic plant transformed with a DNA molecule encoding a fragment of a hypersensitive response elicitor polypeptide or protein, which fragment does not elicit a hypersensitive response, and growing the plant under conditions effective to permit that DNA molecule to impart disease resistance to plants, to enhance plant growth, and/or to control insects. Alternatively, a transgenic plant seed transformed with a DNA molecule encoding a fragment of a hypersensitive response elicitor polypeptide or protein which fragment does not elicit a hypersensitive response can be provided and planted in soil. A plant is then propagated from the planted seed under conditions effective to permit that DNA molecule to impart disease resistance to plants, to enhance plant growth, and/or to control insects.

The embodiment of the present invention where the hypersensitive response elicitor polypeptide or protein is applied to the plant or plant seed can be carried out in a number of ways, including: 1) application of an isolated fragment or 2) application of bacteria which do not cause disease and are transformed with a gene encoding the fragment. In the latter embodiment, the fragment can be applied to plants or plant seeds by applying bacteria containing the DNA molecule encoding the fragment of the hypersensitive response elicitor polypeptide or protein which fragment does not elicit a hypersensitive response. Such bacteria must be capable of secreting or exporting the fragment so that the fragment can contact plant or plant seed cells. In these embodiments, the fragment is produced by the bacteria in plants or on seeds or just prior to introduction of the bacteria to the plants or plant seeds.

The methods of the present invention can be utilized to treat a wide variety of plants or their seeds to impart disease resistance, enhance growth, and/or control insects. Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Examples of suitable ornamental plants are: *Arabidopsis thaliana*, Sainipaulia, petunia, pelargonium, poinsettia, chrysanthemum, carnation, and zinnia.

With regard to the use of the fragments of the hypersensitive response elicitor protein or polypeptide of the present invention in imparting disease resistance, absolute immunity against infection may not be conferred, but the severity of the disease is reduced and symptom development is delayed. Lesion number, lesion size, and extent of sporulation of fungal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi. Resistance, inter alia, to the following viruses can be achieved by the method of the present invention: Tobacco mosaic virus and Tomato mosaic virus. Resistance, inter alia, to the following bacteria can also be imparted to plants in accordance with present invention: *Pseudomonas solanacearum, Pseudomonas syringae* pv. *tabaci*, and *Xanthamonas campestris* pv. *pelargonil.* Plants can be made resistant, inter alia, to the following fungi by use of the method of the present invention: *Fusarium oxysporum* and *Phytophthora infestans.*

With regard to the use of the fragments of the hypersensitive response elicitor protein or polypeptide of the present invention to enhance plant growth, various forms of plant growth enhancement or promotion can be achieved. This can occur as early as when plant growth begins from seeds or later in the life of a plant. For example, plant growth according to the present invention encompasses greater yield, increased quantity of seeds produced, increased percentage of seeds germinated, increased plant size, greater biomass, more and bigger fruit, earlier fruit coloration, and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

Another aspect of the present invention is directed to effecting any form of insect control for plants. For example, insect control according to the present invention encompasses preventing insects from contacting plants to which the hypersensitive response elicitor has been applied, preventing direct insect damage to plants by feeding injury, causing insects to depart from such plants, killing insects proximate to such plants, interfering with insect larval feeding on such plants, preventing insects from colonizing host plants, preventing colonizing insects from releasing phytotoxins, etc. The present invention also prevents subsequent disease damage to plants resulting from insect infection.

The present invention is effective against a wide variety of insects. European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, tomato pinworm, and maggots. Collectively, this group of insect pests represents the most economically important group of pests for vegetable production worldwide.

The method of the present invention involving application of the fragment of a hypersensitive response elicitor polypeptide or protein, which fragment does not elicit a hypersensitive response, can be carried out through a variety of procedures when all or part of the plant is treated, including leaves, stems, roots, propagules (e.g., cuttings), etc. This may (but need not) involve infiltration of the fragment of the hypersensitive response elicitor polypeptide or protein into the plant. Suitable application methods include high or low pressure spraying, injection, and leaf abrasion proximate to when elicitor application takes place. When treating plant seeds or propagules (e.g., cuttings), in accordance with the application embodiment of the present invention, the fragment of the hypersensitive response elicitor protein or polypeptide, in accordance with present invention, can be applied by low or high pressure spraying, coating, immersion, or injection. Other suitable application procedures can be envisioned by those skilled in the art provided they are able to effect contact of the fragment with cells of the plant or plant seed. Once treated with the fragment of the hypersensitive response elicitor of the present invention, the seeds can be planted in natural or artificial soil and cultivated using conventional procedures to produce plants. After plants have been propagated from seeds treated in accordance with the present invention, the plants may be treated with one or more applications of the fragment of the hypersensitive response elicitor protein or polypeptide or whole elicitors to impart disease resistance to plants, to enhance plant growth, and/or to control insects on the plants.

The fragment of the hypersensitive response elicitor polypeptide or protein, in accordance with the present invention, can be applied to plants or plant seeds alone or in a mixture with other materials. Alternatively, the fragment can be applied separately to plants with other materials being applied at different times.

A composition suitable for treating plants or plant seeds in accordance with the application embodiment of the present invention contains a fragment of a hypersensitive response elicitor polypeptide or protein which fragment does not elicit a hypersensitive response in a carrier. Suitable carriers include water, aqueous solutions, slurries, or dry powders. In this embodiment, the composition contains greater than 500 nM of the fragment.

Although not required, this composition may contain additional additives including fertilizer, insecticide, fungicide, nematacide, and mixtures thereof. Suitable fertilizers include $(NH4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the hypersensitive response eliciting fragment can be applied to plant seeds with other conventional seed formulation and treatment materials, including clays and polysaccharides.

In the alternative embodiment of the present invention involving the use of transgenic plants and transgenic seeds, a fragment of a hypersensitive response elicitor need not be applied topically to the plants or seeds. Instead, transgenic plants transformed with a DNA molecule encoding such a fragment are produced according to procedures well known in the art. The vector described above can be microinjected directly into plant cells by use of micropipettes to transfer mechanically the recombinant DNA. Crossway, *Mol. Gen. Genetics*, 202:179–85 (1985), which is hereby incorporated by reference. The genetic material may also be transferred into the plant cell using polyethylene glycol. Krens, et al., *Nature*, 296:72–74 (1982), which is hereby incorporated by reference.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes, or other fusible lipid-surfaced bodies. Fraley, et al., *Proc. Natl. Acad. Sci. USA*, 79:1859–63 (1982), which is hereby incorporated by reference.

The DNA molecule may also be introduced into the plant cells by electroporation. From et al., *Proc. Natl. Acad. Sci. USA*, 82:5824 (1985), which is hereby incorporated by reference. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

Agrobacterium is a representative genus of the Gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. lumefaciens* or the Ri plasmid of *A. rhizogenes*. The Ti or Ri plasmid is transmitted to plant cells on infection by Agrobacterium and is stably integrated into the plant genome. J. Schell, *Science*, 237:1176–83 (1987), which is hereby incorporated by reference.

After transformation, the transformed plant cells must be regenerated.

Plant regeneration from cultured protoplasts is described in Evans et al., *Handbook of Plant Cell Cultures*. Vol. 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the gene encoding the fragment of the hypersensitive response elicitor resulting in disease resistance, enhanced plant growth, and/or control of insects on the plant. Alternatively, transgenic seeds or propagules (e.g., cuttings) are recovered from the transgenic plants. The seeds can then be planted in the soil and cultivated using conventional procedures to produce transgenic plants. The transgenic plants are propagated from the planted transgenic seeds under conditions effective to impart disease resistance to plants, to enhance plant growth, and/or to control insects. While not wishing to be bound by theory, such disease resistance, growth enhancement, and/or insect control may be RNA mediated or may result from expression of the polypeptide or protein fragment.

When transgenic plants and plant seeds are used in accordance with the present invention, they additionally can be treated with the same materials as are used to treat the plants and seeds to which a fragment of a hypersensitive response elicitor in accordance with the present invention is applied. These other materials, including a fragment of a hypersensitive response elicitor in accordance with the present invention, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of the fragment of a hypersensitive response elicitor in accordance with the present invention to impart disease resistance, enhance growth, and/or control insects. Such plants may also be treated with conventional plant treatment agents (e.g., insecticides, fertilizers, etc.).

EXAMPLES

Example 1

Bacterial Strains and Plasmids

*Escherichia coli* strains used in the following examples include DH5α and BL21(DE3) purchased from Gibco BRL (Grand Island, N.Y.) and Stratagene (La Jolla, Calif.), respectively. The pET28(b) vector was purchased from Novagen (Madison, Wis.). Eco DH5α/2139 contained the complete hrpN gene. The 2139 construct was produced by D. Bauer at Cornell University. The hrpN gene was cleaved from the 2139 plasmid by restriction enzyme digestion with HindIII, then purified from an agarose gel to serve as the DNA template for PCR synthesis of truncated hrpN clones. These clones were subsequently inserted into the $(His)_6$ vector pET28(b) which contained a $Kan^r$ gene for selection of transformants.

Example 2

DNA Manipulation

Restriction enzymes were obtained from Boehringer Mannheim (Indianapolis, Ind.) or Gibco BRL. T4 DNA ligase, Calf Intestinal Alkaline Phosphatase (CIAP), and PCR Supermix198 were obtained from Gibco BRL. The QIAprep Spin Miniprep Kit, the Qiagen Plasmid Mini Kit, and the QIAquick PCR Purification Kit were purchased from Qiagen (Hilden, Germany). The PCR primers were synthesized by Lofstnd Labs Limited (Gaithersburg, Md.).

The oligopeptides were synthesized by Bio-Synthesis, Inc. (Lewisville, Tex.). All DNA manipulations such as plasmid isolation, restriction enzyme digestion, DNA ligation, and PCR were performed according to standard techniques (Sambrook, et al., Laboratory Manual, Second Edition, Cold Spring Harbor Laboratory Press (1989)) or protocols provided by the manufacturer.

Example 3

Fragmentation of hrpN Gene

A series of N-terminal and C-terminal truncated hrpN genes and internal fragments were generated via PCR (FIG. 1). The full length hrpN gene was used as the DNA template and 3' and 5' primers were designed for each truncated clone (FIG. 2). The 3' primers contained an NdeI enzyme cutting site which contained the start codon ATG (methionine) and the 5' primers contained the stop codon TAA and a HindIII enzyme cutting site for ligation into the pET28(b) vector. PCR was carried out in 0.5 ml tubes in a GeneAmp™ 9700 (Perkin-Elmer, Foster City, Calif.). 45 $\mu$l of Supermix™ (Life Technology, Gaithersburg, Md.) were mixed with 20 pmoles of each pair of DNA primers, 10 ng of full length harpin DNA, and deionized $H_2O$ to a final volume of 50 $\mu$l. After heating the mixture at 95° C. for 2 min, the PCR was performed for 30 cycles at 94° C. for 1 min, 58° C. for 1 min and 72° C. for 1.5 min. The PCR products were verified on a 6% TBE gel (Novex, San Diego, Calif.). Amplified DNA was purified with the QIAquick PCR purification kit, digested with Nde I and Hind III at 37° C. for 5 hours, extracted once with phenol:chloroform:isoamylalcohol (25:25:1) and precipitated with ethanol. 5 $\mu$g of pET28(b) vector DNA were digested with 15 units of NdeI and 20 units of Hind III at 37° C. for 3 hours followed with CIAP treatment to reduce the background resulting from incomplete single enzyme digestion. Digested vector DNA was purified with the QIAquick PCR purification kit and directly used for ligation. Ligation was carried out at 14–16° C. for 5–12 hours in a 15 $\mu$l mixture containing ca. 200 ng of digested pET28(b), 30 ng of targeted PCR fragment, and 1 unit T4 DNA ligase. 5–7.5 $\mu$l of ligation solution were added to 100 $\mu$l of DH5$\alpha$ competent cells in a 15 ml Falcon tube and incubated on ice for 30 min. After a heat shock at 42° C. for 45 seconds, 0.9 ml SOC solution or 0.45 ml LB media were added to each tube and incubated at 37° C. for 1 hour. 20, 100, and 200 $\mu$l of transformed cells were placed onto LB agar with 30 $\mu$g/ml of kanamycin and incubated at 37° C. overnight. Single colonies were transferred to 3 ml LB-media and incubated overnight at 37° C. Plasmid DNA was prepared from 2 ml of culture with the QIAprep Miniprep kit (QIAGEN, Hilden, Germany). The DNA from the transformed cells was analyzed by restriction enzyme digestion or partial sequencing to verify the success of the transformations. Plasmids with the desired DNA sequence were transferred into the BL21 strain using the standard chemical transformation method as indicated above. A clone containing the fill length harpin protein in the pET28(b) vector was generated as a positive control, and a clone with only the pET28(b) vector was generated as a negative control.

Example 4

Expression of Hypersensitive Response Elicitor Truncated Proteins

*Escherichia coli* BL21 (DE3) strains containing the hrpN clones were grown in Luria broth medium (5 g/L Difco Yeast extract, 10 g/L Difco Tryptone, 5 g/L NaCl, and 1 mM NaOH) containing 30 $\mu$g/ml of kanamycin at 37° C. overnight. The bacteria were then inoculated into 100 volumes of the same medium and grown at 37° C. to an OD620 of 0.6–0.8. The bacteria were then inoculated into 250 volumes of the same medium and grown at 37° C. to an $OD_{620}$ of ca. 0.3 or 0.6–0.8. One milli molar IPTG was then added and the cultures grown at 19° C. overnight (ca. 18 hours). Not all of the clones were successfully expressed using this strategy. Several of the clones had to be grown in Terrific broth (12 g/L Bacto Tryptone, 24 g/L Bacto yeast, 0.4% glycerol, 0.17 M KH2PO4, and 0.72 $K_2HPO_4$), and/or grown at 37° C. after IPTG induction, and/or harvested earlier than overnight (Table 1).

TABLE 1

Expression of hypersensitive response elicitor truncated proteins

| Fragment | amino acids (SEQ ID NO: 23) | Growth medium | Induction O.D. | Expression temp. | Harvest time |
|---|---|---|---|---|---|
| 1 (+ control) | 1-403 | LB | ca. 0.3 or 0.6-0.8 | 19° C. or 25° C. | 16–18 hr |
| 2 (+ control) | — | LB and TB | ca. 0.3 or 0.6-0.8 | 19° C. and 37° C. | 16–18 hr |
| 3 | 105-403 | LB | 0.6-0.8 | 19° C. | 16–18 hr |
| 4 | 169-403 | TB | ca. 0.3 | 19° C. | 16–18 hr |
| 5 | 210-403 | LB or M9ZB | 0.6-0.8 | 19° C. | 16–18 hr |
| 6 | 257-403 | LB or M9ZB | 0.6-0.8 | 19° C. | 16–18 hr |
| 7 | 343-403 | LB | ca. 0.3 | 19° C. | 5 hr |
| 8 | 1-75 | TB | ca. 0.3 | 37° C. | 16–18 hr |
| 9 | 1-104 | TB | ca. 0.3 | 37° C. | 16–18 hr |
| 10 | 1-168 | TB | ca. 0.3 | 37° C. | 16–18 hr |
| 11 | 1-266 | LB | ca. 0.3 | 37° C. | 4 hr |
| 12 | 1-342 | LB | 0.6-0.8 | 19° C. | 16–18 hr |
| 13 | 76-209 | LB | ca. 0.3 | 37° C. | 5 hr |
| 14 | 76-168 | TB or LB | ca. 0.3 | 37° C. | 3 hr or 16–18 hr |
| 15 | 105-209 | M9ZB | ca. 0.3 | 37° C. | 3 hr |
| 16 | 169-209 | | no expression | | |
| 17 | 105-168 | LB | ca. 0.3 | 37° C. | 3–5 hr |
| 18 | 99-209 | LB | ca. 0.3 | 37° C. | 3 hr |
| 19 | 137-204 | LB | ca. 0.3 | 37° C. | 3 hr |
| 20 | 137-180 | LB | ca. 0.3 | 37° C. | 16-18 hr. |
| 21 | 105-180 | LB | ca. 0.3 | 37° C. | 3 hr |
| 22 | 150-209 | | no expression | | |
| 23 | 150-180 | | no expression | | |

Example 5

Small Scale Purification of Hypersensitive Response Elicitor Truncated Proteins (Verification of Expression)

A 50 ml culture of a hrpN clone was grown as above to induce expression of the truncated protein. Upon harvesting of the culture, 1.5 ml of the cell suspension were centrifuged at 14,000 rpm for 5 minutes, re-suspended in urea lysis buffer (8 M urea, 0.1 M $Na_2HPO_4$, and 0.01 M Tris—pH 8.0), incubated at room temperature for 10 minutes, then centrifuged again at 14,000 rpm for 10 minutes, and the supernatant saved. A 50 $\mu$l aliquot of a 50% slurry of an equilibrated $(His)_6$-binding nickel agarose resin was added to the supernatant and mixed at 4° C. for one hour. The nickel agarose was then washed three times with urea washing buffer (8 M urea, 0.1 M $Na_2HPO_4$, and 0.01 M Tris—pH 6.3), centrifuging at 5,000 rpm for five minutes between washings. The protein was eluted from the resin with 50 $\mu$l of urea elution buffer (8 M urea, 0.1 M $Na_2HPO_4$, 0.01 M Tris, and 0.1 M EDTA—pH 6.3). The eluate was run on a 4–20%, a 16%, or a 10–20% Tris-Glycine pre-cast gel depending upon the size of the truncated protein to verify the expression.

Example 6

Induction of HR in Tobacco

A 1.5 ml aliquot from the 50 ml cultures grown for small scale purification of the truncated proteins was centrifuged at 14,000 rpm for four minutes and re-suspended in an equal volume of 5 mM potassium phosphate buffer, pH 6.8. The cell suspension was sonicated for ca. 30 seconds then diluted 1:2 and 1:10 with phosphate buffer. Both dilutions plus the neat cell lysate were infiltrated into the fourth to ninth leaves of 10–15 leaf tobacco plants by making a hole in single leaf panes and infiltrating the bacterial lysate into the intercellular leaf space using a syringe without a needle. The HR response was recorded 24–48 hr post infiltration. Tobacco (*Nicotiana tabacum* v. Xanthi) seedlings were grown in an environmental chamber at 20–25° C. with a photoperiod of 12-h light/12-h dark and ca. 40% RH. Cell lysate was used for the initial HR assays (in order to screen the truncated proteins for HR activity) as the small scale urea purification yielded very little protein which was denatured due to the purification process.

Example 7

Large Scale Native Purification of Hypersensitive Response Elicitor Truncated Proteins for Comprehensive Biological Activity Assays Six 500 ml cultures of a hrpN clone were grown as described earlier to induce expression of the truncated protein. Upon harvesting of the culture, the cells were centrifuged at 7,000 rpm for 5 minutes, re-suspended in imidazole lysis buffer (5 mM imidazole, 0.5 M NaCl, 20 mM Tris) plus Triton X-100 at 0.05% and lysozyme at 0.1 mg/ml, incubated at 30° C. for 15 minutes, sonicated for two minutes, centrifuged again at 15,000 rpm for 20 minutes, and the supernatant was saved. A 4 ml aliquot of a 50% slurry of an equilibrated $(His)_6$-binding nickel agarose resin was added to the supernatant and mixed at 4° C. for ca. four hours. The nickel agarose was then washed three times with imidazole washing buffer (20 mM imidazole, 0.5 M NaCl, and 20 mM Tris), centrifuging at 5,000 rpm for five minutes between washings, then placed in a disposable chromatography column. The column was centrifuged at 1100 rpm for one minute to remove any residual wash buffer and then the protein was eluted from the resin with 4 ml of imidazole elution buffer (1 M imidazole, 0.5 M NaCl, and 20 mM Tris) by incubating the column with the elution buffer for ten minutes at room temperature and then centrifuging the column at 1100 rpm for one minute. The eluate was run on a 4–20%, a 16%, or a 10–20% Tris-Glycine pre-cast gel depending upon the size of the truncated protein to verify the expression. The concentration of the proteins was determined by comparison of the protein bands with a standard protein in the Mark 12 molecular weight marker.

Example 8

Large Scale Urea Purification of Hypersensitive Response Elicitor Truncated Proteins For Comprehensive Biological Activity Assay The procedure was the same as the large scale native purification except that urea lysis buffer, washing buffer, and elution buffer were used, and the cells were not sonicated as in the native purification. After purification, the protein was renatured by dialyzing against lower and lower concentrations of urea over an eight hour period, then dialyzing overnight against 10 mM Tris/20 mM NaCl. The renaturing process caused the N-terminal proteins to precipitate. The precipitated 1–168 protein was solubilized by the addition of 100 mM Tris-HCl at pH 10.4 then heating the protein at 30° C. for ca. one hour. The concentration of the protein was determined by comparison of the protein bands with a standard protein in the Mark 12 molecular weight marker. The 1–75 and 1–104 protein fragments were not successfully solubilized using this strategy so they were sonicated in 100 mM Tris-HCl at pH 10.4 to solubilize as much of the protein as possible and expose the active sites of the protein for the biological activity assays.

Example 9

Induction of Growth Enhancement (GE)

Sixty tomato (Lycopersicon spp. cv. Marglobe) seeds were soaked overnight in 10 and 20 μg/ml of the truncated protein diluted with 5mM potassium phosphate buffer, pH 6.8. The next morning, the sixty seeds were sewn in three pots and 12–15 days later and again 18–20 days later the heights of the 10 tallest tomato plants per pot were measured and compared with the heights of the control plants treated only with phosphate buffer. Analyses were done on the heights to determine if there was a significant difference in the height of the plants treated with the truncated proteins compared with the buffer control, and thereby determine whether the proteins induced growth enhancement.

Example 10

Induction of Systemic Acquired Resistance (SAR)

Three tobacco (*Nicotiana tabacum* cv. Xanthi) plants with 8–12 leaves (ca. 75 day old plants) were used in the assay. One leaf of the tobacco plants was covered up and the rest of the leaves were sprayed with ca. 50 ml of a 20 μg/ml solution of the truncated proteins diluted with 5 mM potassium phosphate buffer. Five to seven days later two leaves (the unsprayed leaf and the sprayed leaf opposite and just above the unsprayed leaf) were inoculated with 20 μl of a 1.8 μg/ml solution of TMV along with a pinch of diatomaceous earth by rubbing the mixture along the top surface of the leaves. The TMV entered the plants through tiny lesions made by the diatomaceous earth. Ca. 3–4 days post TMV inolucation, the number of TMV lesions was counted on both leaves compared with the number of lesions on the negative control buffer treated leaves. Analyses were done to determine the efficacy of reducing the number of TWV lesions by the protein fragents compared to the buffer control. Percentage of efficacy was calculated as: Reduction in TMV lesions (% efficacy)=100×(1−mean # of lesions on treated leaves/mean # of lesions on buffer control leaves).

Example 11

Expression of Hypersensitive Response Elicitor Truncated Proteins

The small scale expression and purification of the fragment proteins was done expression and HR activity (Table 2).

TABLE 2

Expression and HR activity of hypersensitive response elicitor truncated proteins (small scale screening)

| Fragment # | Amino Acids (SEQ ID NO:23) | Expression | HR activity |
|---|---|---|---|
| 1(+control) | 1-403 | + | + |
| 2(−control) | — | background protein only | − |
| 3 | 105-403 | + | + |
| 4 | 169-403 | + | − |
| 5 | 210-403 | + | − |
| 6 | 267-403 | + | − |
| 7 | 343-403 | +/− | − |
| 8 | 1-75 | + | − |
| 9 | 1-104 | + | +/− |
| 10 | 1-168 | + | + |
| 11 | 1-266 | + | + |
| 12 | 1-342 | + | + |
| 13 | 76-209 | + | + |
| 14 | 76-168 | + | − |
| 15 | 105-209 | + | + |
| 16 | 169-209 | − | − |
| 17 | 105-168 | + | − |
| 18 | 99-209 | + | + |
| 19 | 137-204 | + | + |
| 20 | 137-180 | + | + |
| 21 | 105-180 | + | + |
| 22 | 150-209 | − | − |
| 23 | 150-180 | − | − |

All of the cloned fragment proteins were expressed at varying levels except for three small fragment (amino acids 169–209, 150–209, and 150–180). Fragments 210–403 and 267–403 were expressed very well, yielding a high concentration of protein from a small scale purification, resulting in a substantial protein band on SDS gel electrophoresis. Other fragments (such as a.a. 1–168 and 1–104) produced much less protein, resulting in faint protein bands upon electrophoresis. It was difficult to determine whether fragment 343–403, the smallest C-terminal protein, was expressed, as there were several background proteins apparent on the gel, in addition to the suspected 343–403 protein. The positive and negative control proteins, consisting of the full length hypersensitive response elicitor protein and only background proteins, respectively, were tested for expression and HR activity as well.

The large scale expression and purification of the fragment proteins was done to determine the level of expression and titer of the HR activity (Table 3).

TABLE 3

Expression level and HR titer of hypersensitive response elicitor truncated proteins (large sale purification)

| Fragment # | Amino acids (SEQ ID NO: 23) | Expression | HR titer |
|---|---|---|---|
| 1(+control) | 1-403 | 3.7 mg/ml | 5-7 μg/ml |
| 2(−control) | — | — | 1:2 dilution |
| 4 | 169-403 | 2 mg/ml | — |
| 5 | 210-403 | 5 mg/ml | — |
| 6 | 267-403 | 4 mg/ml | — |
| 7 | 343-402 | 200 μg/ml | — |
| 8 | 1-75 | 50 μg/ml | — |
| 9 | 1-104 | 50 μg/ml | 3 μg/ml (1:16 dilution) |
| 10 | 1-168 | 1 mg/ml | 1 μg/ml |
| 13 | 76-209 | 2.5 mg/ml | 5 μg/ml |
| 14 | 76-168 | 2 mg/ml | — |
| 15 | 105-209 | 5 mg/ml | 5-10 μg/ml |
| 17 | 105-168 | 250 μg/ml | — |
| 19 | 137-204 | 3.6 mg/ml | 3.5 μg/ml |
| 20 | 137-180 | 250 μg/ml | 16 μg/ml |

The truncated proteins deemed to be the most important in characterizing the hypersensitive response elicitor were chosen for large scale expression. The positive control (full length hypersensitive response elicitor) was expressed at a relatively high level at 3.7 mg/ml. All of the C-terminal proteins were expressed at relatively high levels from 2–5 mg/ml, except for fragment 343–403 as discussed earlier. The N-terminal fragments were expressed very well also; however, during the purification process, the protein precipitated and very little was resolubilized. The concentrations in Table 3 reflect only the solubilized protein. The internal fragments were expressed in the range of 2–3.6 mg/ml. It was extremely difficult to determine the concentration of fragment 105–168 (it was suspected that the concentration was much higher than indicated), as the protein bands on the SDS gel were large, but poorly stained. The negative control contained several background proteins as expected, but no obviously induced dominant protein.

Example 12

Induction of HR in Tobacco

The full length positive control protein elicited HR down to only 5–7 μg/ml. The negative control (pET 28) imidazole purified "protein"—which contained only background proteins—elicited an HR response down to the 1:2 dilution, which lowered the sensitivity of the assay as the 1:1 and 1:2 dilutions could not be used. This false HR was likely due to an affinity of the imidazole used in the purification process to bind to one or several of the background proteins, thereby not completely dialyzing out. Imidazole at a concentration of ca. 60 mM did elicit a false HR response.

One definitive domain encompassing a small internal region of the protein from aa. 137–180 (SEQ ID NO: 23), a mere 44 a.a, is identified as the smallest HR domain. The other potential HR domain is thought to be located in the N-terminus of the protein from a. a1–104 (possibly a.a 1–75) (SEQ ID NO: 23). It was difficult to confirm or narrow down the N-terminus HR domain due to the difficulties encountered in purifying these fragment proteins. The N-terminus fragment proteins had to be purified with urea as no protein was recovered when the native purification process was used. Consequently, these proteins precipitated during the renaturing process and were difficult or nearly impossible to get back into solution, thereby making it hard to run the proteins through the HR assay, as only soluble protein is able to elicit HR. Difficulty narrowing the N-terminus HR domain was only compounded by the fact that the negative control elicited false HR at the low dilution levels thereby reducing the sensitivity of the assay.

Surprisingly, when the internal HR domain was cleaved between a.a. 168 and 169 (fragments 76–168 and 105–168) (SEQ ID NO: 23) the fragment lost its HR activity. This suggests that the HR activity of fragment 1–168 (SEQ ID NO: 23) should not be attributed to the internal HR domain, but rather to some other domain, leading to the assumption that there was likely a second HR domain to be found in the N-terminal region of the protein. However, as discussed earlier it was difficult to confirm this assumption.

The hypersensitive response elicitor C-terminus (a.a. 210–403 (SEQ ID NO: 23)) did not contain an HR domain. It did not elicit HR at a detectable level using the current HR assay. Even the large C-terminal fragment from a.a. 169–403 (SEQ ID NO: 23) did not elicit HR even though it contained part of the internal HR domain. As stated above, cleaving the protein between amino acids 168 and 169 (SEQ ID NO: 23) causes a loss of HR activity.

Because some of the small cloned proteins with 61 a.a. or less were not expressed, several oligopeptides were synthesized with 30 a.a. to narrow down the functional region of the internal HR domain. The oligopeptides were synthesized within the range of a.a. 121–179 (SEQ ID NO: 23). However, these oligos did not elicit HR. It was not expected that there would be an HR from oligos 137–166, 121–150, and 137–156 (SEQ ID NO: 23) as these fragments did not contain the imperative amino acids 168 and 169 (SEQ ID NO: 23). It was expected that the oligo 150–179 (SEQ ID NO: 23) would elicit an HR. It is possible that 30 a.a. is too small for the protein to elicit any activity due to a lack of folding and, therefore, a lack of binding or that during the synthesis of the peptides important amino acids were missed (either in the process, or simply by the choice of which 30 amino acids to synthesize) and, therefore, the fragments would not be able to elicit HR.

Example 13

Induction of Plant Growth Enhancement (PGE)

The C-terminal fragments enhanced the growth of tomato by 9% to 2 1%. The N-terminal fragments enhanced the growth of tomato by 4% to 13%. The internal fragments enhanced growth by 9% to 20%. The 76–209 fragment enhanced growth by 18% at a concentration of 60 μg/ml, but not at the typical 20 μg/ml. This was attributed to the inaccuracy of the quantification process (Table 4).

TABLE 4

| Fragment # | Amino acids | PGE ht>buffer @10 μg/ml | PGE ht>buffer @20 μg/ml |
|---|---|---|---|
| 1(+control) | 1-403 | 12% | 11% |
| 2(−control) | — | −3% | −2% |
| 4 | 169-403 | 9% | 12% |
| 5 | 210-403 | 13% | 14%<br>16% @ 40 μg/ml |
| 6 | 267-403 | 21% | 21%<br>23% @ 40 μg/ml |
| 7 | 343-403 | 7% | 7% |
| 9 | 1-104 | 4% | 8% |
| 10 | 1-168 | 13% | 5% |
| 13 | 76-209 | 7% | 4%<br>18% @ μg/ml |
| 14 | 76-168 | 18% | 20% |
| 15 | 105-209 | 14% | 19% |
| 17 | 105-168 | 19% | 16% |
| 19 | 137-204 | 11% | 13% |
| 20 | 137-180 | — | 9% |

*A height greater than 10% above the buffer control was necessary to pass the PGE assay.

The oligopeptides enhanced growth from 7.4% to 17.3% (Table 5).

TABLE 5

| Fragment | Amino acids | Expression | HR titer | TMV efficacy | PGE ht>buffer |
|---|---|---|---|---|---|
| oligo | 150-179 | NA | — | 72.9% | 10.1% |
| oligo | 137-166 | NA | — | 61.2% | 12.0% |
| oligo | 121-150 | NA | — | 60.0% | 17.3% |
| oligo | 137-156 | NA | — | −87.7% | 7.4% |

The data suggests that there is more than one PGE domain, although the C-terminal and internal domains appear to be dominant over the N-terminal domain, as the N-terminal fragments enhanced growth the least amount.

Example 14

Induction of Systemic Acquired Resistance (SAR)

All of the hypersensitive response elicitor fragments tested to date appear to have 60% effilcacy or greater, except for the oligopeptide 137–156 (Tables 5 and 6).

TABLE 6

| Fragment # | Amino acids | Efficacy of TMV control |
|---|---|---|
| 1 (+control) | 1-403 | 84% & 72% |
| 2 (−control) | — | 40% & 31% |
| 4 | 169-403 | 64% & 79% |
| 5 | 210-403 | 77% and 78% |
| 6 | 267-403 | 70% and 72% |
| 9 | 1-104 | 82% |
| 10 | 1-168 | 69% |
| 13 | 76-209 | 44% and 84% |
| 14 | 76-168 | 83% & 87% |
| 15 | 105-209 | 57% and 67% |
| 17 | 105-168 | 89% |
| 19 | 137-204 | 89% & 77% |
| 20 | 137-180 | 64% & 58% |

These data suggest that there are multiple SAR domains within the protein.

Example 15

Relationship Between HR, PGE, and SAR

It is clear that the hypersensitive response activity is separable from the plant growth enhancement activity. The C-terminal fragments clearly enhance the growth of tomato by ca. 20% at a concentration of only 20 μg/ml, but these same fragments were not able to elicit HR in tobacco, even at higher concentrations than 200 μg/ml. The SAR activity also appears to be separable from the HR activity. This finding is highly significant for future work on transgenic applications of the hypersensitive response elicitor technology. The fragments that induce PGE and/or SAR but do not elicit HR will be imperative for this technology, as constitutive expression of even low levels of an HR elicitor might kill a plant.

Example 16

Non-HR Eliciting Fragments Derived from the Hypersensitive Response Elicitor from *Pseudomonas syringae* pv. *syringae* Induce Resistance in Tobacco to TMV and Promote the Growth of Tomato To test whether non-HR eliciting fragments derived from HrpZ, the hypersensitive response elicitor from *Pseudomo-*

*nas syringae* pv. *syringae*, is able to induce disease resistance, several fragment constructs were made and the expressed fragment proteins were tested for HR elicitation and disease resistance induction in tobacco and growth promotion in tomato.

The following segments of hrpZ, the gene encoding the hypersensitive response elicitor from *Pseudomonas syringae* pv. *syringae*, were amplified by PCR using Pfu Turbo (Stratagene): Regions coding for amino acids 152–190, aa 152–294, aa 190–294, aa 301–341, and full length HrpZ (aa 1–341). The DNA fragments were cloned into pCAL-n (Stratagene) to create C-terminal fusion proteins to the calmodulin-binding peptide. pCAL-n was chosen, because the fusion protein could be easily and gently purified on calmodulin resin. The DNA was transformed into *E. coil* DH5α, and the correct clones were identified. The clones were then transferred to *E. coil* BLR DE3 for protein expression. The bacteria were grown in Terrific Broth to an $OD_{620}$ of 0.8–1.0. Protein expression was then induced with IPTG and the bacteria were incubated for an additional 3 h. All of the HrpZ fragments were able to be expressed this way.

Amino acid fragments 152–294 and 190–294 were chosen for further analysis and characterization. It was expected that the fragment 152–294 contained a domain that elicited the HR, while fragment 190–294 contained no domain that elicited the HR. The cultures were spun down, and the bacteria resuspended in 40 ml of 10 mM Tris pH 8.0. Twenty μl of antifoam and 40 μl of 200 mM PMSF were added, and the bacteria was sonicated to break open the cells. The bacterial debris was removed by centrifugation, and the supernatant was placed in a boiling water bath for 10 min. The precipitate was removed by centrifugation and the supernatant, a crude protein preparation, was retained for tests.

Fifteen μl of each supernatant was run on a gel and stained to determine if the protein was present. It was estimated that about five times as much of the 152–294 fragment was present as the 190–294 fragment. Several dilutions of each preparation were infiltrated into tobacco leaves on two plants for HR tests (Table 7). As shown in Table 7, the 152–294 fragment elicited an HR, but the 190–294 fragment did not.

TABLE 7

HR test results of HrpZ fragments

| HrpZ Fragment | Dilution of Fragment Preparation[a] 1:2 | 1:5 | 1:25 | 1:125 |
|---|---|---|---|---|
| 152-294 | +,+[b] | +,+ | +,+ | –,– |
| 190-294 | –,– | –,– | –,– | –,– |

[a]The preparations were diluted with MilliQ water.
[b]The results are indicated for each of two plants. +, HR; –, no HR.

The fragment preparations were then tested for inducing resistance to TMV and for growth enhancement. Due to the difference in concentration of the HrpZ fragments, the 152–294 preparation was diluted 40-fold and the 190–294 preparation was diluted 8-fold. The results showed that the 190–294 aa fragment reduced the number of TMV lesions by 85% in comparison to buffer controls (Table 8). In contrast, the 152–294 aa fragment reduced the number of TMV lesions by only 55%. As also shown in Table 8, plants treated with the 152–294 aa fragment grew 4.64% more than buffer treated plants, while plants treated with the 190–294 aa fragment grew 2.62% more than the buffer treated plants.

TABLE 8

HR test, TMV, and PGE test results

| HrpZ Fragment | HR elicitation[a] | TMV (% efficacy)[b] | PGE(% > buffer ht)[c] |
|---|---|---|---|
| 152-294 | + | 54.64 | 4.64 |
| 190-294 | – | 85.25 | 2.62 |

[a]+, elicits HR in tobacco leaves; –, no HR in tobacco leaves.
[b]% reduction in TMV lesions in unsprayed leaf of tobacco.
[c]% greater height than buffer sprayed plants.

The results of these tests show that amino acids 152–190 appear to be involved in HR elicitation, because their removal eliminated the ability to elicit the HR. Both fragment preparations achieved disease control and growth enhancement. Thus, the ability to elicit the HR is not the determining factor for reduction in TMV infection and growth enhancement.

Example 17

Use of 13 Amino Acid Peptide Derived from *Phytophihora megasperma* Stimulates Tomato Seedling Growth Parsley leaves develop a typical resistance reaction against the soybean pathogen *Phytophthora megasperma* comprising hypersensitive cell death, defense related gene activation, and phytoalexin formulation. Several years ago, a 42 kDa glycoprotein elicitor was purified from the fungal culture filtrate of *Phytophthora megasperma* (Parker et al., "An Extracellular Glycoprotein from *Phytophthora megasperma* f.sp. glycinea Elicits Phytoalexin Synthesis in Cultured Parsley Cells and Protoplasts," *Mol. Plant Microbe Interact.* 4:19–27 (1991), which is hereby incorporated by reference). Then, an oligopeptide of 13 amino acid was identified within the 42 kDa glycoprotein. The 13 amino acids peptide appeared to have similar biological activity as that of the full length glycoprotein (42 kDa). It is sufficient to elicit a complex defense response in parsley cells including H+/Ca2+ influxes, K+/Cl– effluxes, active oxygen production, SAR gene induction, and phytoalexin compound accumulation (Numberger et al., "High Affinity Binding of a Fungal Oligopeptide Elicitor to Parsley Plasma Membranes Triggers Multiple Defense Response," *Cell* 78:449–460 (1994), which is hereby incorporated by reference).

To test if the 13 amino acid peptide derived from the 42 kDa protein also enhanced plant growth, 20 mg of the oligopeptide was synthesized from Biosynthesis Corp. The synthesized sequence of the peptide is NH2-Val-Trp-Asn-Gln-Pro-Val-Arg-Gly-Phe-Lys-Val-Tyr-Glu-COOH (SEQ ID NO: 39). The synthesized peptide was resuspended in 10 ml of 5 mM potassium phosphate buffer and, then, diluted to 1 and 100 ng/ml with the same buffer. About 100 tomato seeds (variety, Marglobe) were submerged in 20 ml of peptide solution overnight. The soaked seeds were planted in an 8 inch pot with artificial soil. Seeds soaked in the buffer without the peptide were used as a control. After seedlings emerged and the first two true leaves fully expanded, the height of the tomato seedlings was recorded. The peptide was not able to elicit the HR in tobacco and other tested plants. However, it had a profound effect on plant growth promotion. Table 9 shows that tomato seedlings treated with the peptide increased 12.6% in height, indicating that the fungal peptide derived from the 42 kDa glycroprotein can promote tomato seedling growth. Extended studies showed that the peptide also had similar growth effect in other crops including tobacco. Similar growth promotion effects were achieved by plants sprayed with the peptide solution.

TABLE 9

| Treatment | Height of seedlings (cm) | Average (cm) | % Change |
|---|---|---|---|
| Buffer | 6.0 6.0 6.0 5.5 5.5<br>5.5 5.5 5.0 5.0 5.5 | 5.55 | — |
| Peptide Solution (100 ng/ml) | 6.5 6.0 6.5 6.5 6.5<br>6.0 6.0 6.0 6.0 6.5 | 6.25 | 12.6 |

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. An isolated fragment of a hypersensitive response elicitor protein or polypeptide, wherein said fragment is selected from the group consisting of a C-terminal fragment of the amino acid sequence of SEQ ID NO: 23 consisting of the following amino acids of SEQ ID NO: 23: 169 to 403, 210 to 403, 267 to 403, or 343 to 403; an internal fragment of the amino acid sequence of SEQ ID NO: 23 consisting of the following amino acids of SEQ ID NO: 23: 150 to 179, 137 to 166, 121 to 150, 76 to 168, 105 to 168, or 137 to 156; and a fragment of the amino acid sequence of SEQ ID NO: 31 consisting of amino acids 190 to 294 of SEQ ID NO: 31.

2. An isolated fragment according to claim 1, wherein the fragment is a C-terminal fragment of the amino acid sequence of SEQ ID NO: 23 consisting of the following amino acids of SEQ ID NO: 23: 169 to 403, 210 to 403, 267 to 403, or 343 to 403.

3. An isolated fragment according to claim 1, wherein the fragment is an internal fragment of the amino acid sequence of SEQ ID NO: 23 consisting of the following amino acids of SEQ ID NO: 23: 150 to 179, 137 to 166, 121 to 150, 76 to 168, 105 to 168, or 137 to 156.

4. An isolated fragment according to claim 1, wherein the fragment consists of amino acids 190 to 294 of SEQ ID NO: 31.

5. A method of imparting disease resistance to plants comprising:

administering a fragment of a hypersensitive response elicitor protein or polypeptide according to claim 1 in a non-infectious form to a plant or plant seed under conditions effective to impart disease resistance to the plant or a plant grown from the plant seed.

6. A method according to claim 5, wherein plants are treated during said administering.

7. A method according to claim 5 further comprising:

planting the seeds treated with the fragment of the hypersensitive response elicitor in natural or artificial soil and propagating plants from the seeds planted in the soil.

8. A method of enhancing plant growth comprising:

administering a fragment of a hypersensitive response elicitor protein or polypeptide according to claim 1 in a non-infectious form to a plant or plant seed under conditions effective to enhance plant growth of the plant or of a plant grown from the plant seed.

9. A method according to claim 8, wherein plants are treated during said administering.

10. A method according to claim 8 further comprising:

planting the seeds treated with the fragment of the hypersensitive response elicitor in natural or artificial soil and propagating plants from the seeds planted in the soil.

11. A method of insect control for plants comprising:

administering a fragment of a hypersensitive response elicitor protein or polypeptide according to claim 1 in a non-infectious form to a plant or plant seed under conditions effective to control insects.

12. A method according to claim 11, wherein plants are treated during said administering.

13. A method according to claim 11 further comprising:

planting the seeds treated with the fragment of the hypersensitive response elicitor in natural or artificial soil and propagating plants from the seeds planted in the soil.

14. An isolated fragment according to claim 2, wherein the fragment has an amino acid sequence consisting of amino acids 169 to 403 of SEQ ID NO: 23.

15. An isolated fragment according to claim 2, wherein the fragment has an amino acid sequence consisting of amino acids 210 to 403 of SEQ ID NO: 23.

16. An isolated fragment according to claim 2, wherein the fragment has an amino acid sequence consisting of amino acids 267 to 403 of SEQ ID NO: 23.

17. An isolated fragment according to claim 2, wherein the fragment has an amino acid sequence consisting of amino acids 343 to 403 of SEQ ID NO: 23.

18. An isolated fragment according to claim 3, wherein the fragment has an amino acid sequence consisting of amino acids 150 to 179 of SEQ ID NO: 23.

19. An isolated fragment according to claim 3, wherein the fragment has an amino acid sequence consisting of amino acids 137 to 166 of SEQ ID NO: 23.

20. An isolated fragment according to claim 3, wherein the fragment has an amino acid sequence consisting of amino acids 121 to 150 of SEQ ID NO: 23.

21. An isolated fragment according to claim 3, wherein the fragment has an amino acid sequence consisting of amino acids 76 to 168 of SEQ ID NO: 23.

22. An isolated fragment according to claim 3, wherein the fragment has an amino acid sequence consisting of amino acids 105 to 168 of SEQ ID NO: 23.

23. An isolated fragment according to claim 3, wherein the fragment has an amino acid sequence consisting of amino acids 137 to 156 of SEQ ID NO: 23.

* * * * *

SEQUENCE LISTING

```
<160> NUMBER OF SEQ ID NOS: 39

<210> SEQ ID NO 1
<211> LENGTH: 31
<212> TYPE: DNA
<213> ORGANISM: Erwinia amylovora

<400> SEQUENCE: 1

gggaattcat atgagtctga atacaagtgg g                                      31


<210> SEQ ID NO 2
<211> LENGTH: 31
<212> TYPE: DNA
<213> ORGANISM: Erwinia amylovora

<400> SEQUENCE: 2

gggaattcat atgggcggtg gcttaggcgg t                                      31


<210> SEQ ID NO 3
<211> LENGTH: 29
<212> TYPE: DNA
<213> ORGANISM: Erwinia amylovora

<400> SEQUENCE: 3

ggcatatgtc gaacgcgctg aacgatatg                                         29


<210> SEQ ID NO 4
<211> LENGTH: 31
<212> TYPE: DNA
<213> ORGANISM: Erwinia amylovora

<400> SEQUENCE: 4

gggaattcat atgttaggcg gttcgctgaa c                                      31


<210> SEQ ID NO 5
<211> LENGTH: 29
<212> TYPE: DNA
<213> ORGANISM: Erwinia amylovora

<400> SEQUENCE: 5

ggcatatgct gaacacgctg ggctcgaaa                                         29


<210> SEQ ID NO 6
<211> LENGTH: 29
```

-continued

<212> TYPE: DNA
<213> ORGANISM: Erwinia amylovora

<400> SEQUENCE: 6
ggcatatgtc aacgtcccaa aacgacgat 29

<210> SEQ ID NO 7
<211> LENGTH: 27
<212> TYPE: DNA
<213> ORGANISM: Erwinia amylovora

<400> SEQUENCE: 7
ggcatatgtc cacctcagac tccagcg 27

<210> SEQ ID NO 8
<211> LENGTH: 34
<212> TYPE: DNA
<213> ORGANISM: Erwinia amylovora

<400> SEQUENCE: 8
gggaattcat atgcaaagcc tgtttggtga tggg 34

<210> SEQ ID NO 9
<211> LENGTH: 31
<212> TYPE: DNA
<213> ORGANISM: Erwinia amylovora

<400> SEQUENCE: 9
gggaattcat atgggtaatg gtctgagcaa g 31

<210> SEQ ID NO 10
<211> LENGTH: 31
<212> TYPE: DNA
<213> ORGANISM: Erwinia amylovora

<400> SEQUENCE: 10
gggaattcat atgaaagcgg gcattcaggc g 31

<210> SEQ ID NO 11
<211> LENGTH: 34
<212> TYPE: DNA
<213> ORGANISM: Erwinia amylovora

<400> SEQUENCE: 11
gggaattcat atgacaccag ccagtatgga gcag 34

<210> SEQ ID NO 12
<211> LENGTH: 31
<212> TYPE: DNA
<213> ORGANISM: Erwinia amylovora

<400> SEQUENCE: 12
gcaagcttaa cagcccacca ccgcccatca t 31

<210> SEQ ID NO 13
<211> LENGTH: 31
<212> TYPE: DNA
<213> ORGANISM: Erwinia amylovora

<400> SEQUENCE: 13
gcaagcttaa atcgttcagc gcgttcgaca g 31

<210> SEQ ID NO 14

-continued

<211> LENGTH: 34
<212> TYPE: DNA
<213> ORGANISM: Erwinia amylovora

<400> SEQUENCE: 14
gcaagcttaa tatctcgctg aacatcttca gcag 34

<210> SEQ ID NO 15
<211> LENGTH: 30
<212> TYPE: DNA
<213> ORGANISM: Erwinia amylovora

<400> SEQUENCE: 15
gcaagcttaa ggtgccatct tgcccatcac 30

<210> SEQ ID NO 16
<211> LENGTH: 34
<212> TYPE: DNA
<213> ORGANISM: Erwinia amylovora

<400> SEQUENCE: 16
gcaagcttaa atcagtgact cctttttat aggc 34

<210> SEQ ID NO 17
<211> LENGTH: 31
<212> TYPE: DNA
<213> ORGANISM: Erwinia amylovora

<400> SEQUENCE: 17
gcaagcttaa caggcccgac agcgcatcag t 31

<210> SEQ ID NO 18
<211> LENGTH: 31
<212> TYPE: DNA
<213> ORGANISM: Erwinia amylovora

<400> SEQUENCE: 18
gcaagcttaa accgataccg gtacccacgg c 31

<210> SEQ ID NO 19
<211> LENGTH: 34
<212> TYPE: DNA
<213> ORGANISM: Erwinia amylovora

<400> SEQUENCE: 19
gcaagcttaa tccgtcgtca tctggcttgc tcag 34

<210> SEQ ID NO 20
<211> LENGTH: 25
<212> TYPE: DNA
<213> ORGANISM: Erwinia amylovora

<400> SEQUENCE: 20
gcaagcttaa gccgcgccca gcttg 25

<210> SEQ ID NO 21
<211> LENGTH: 338
<212> TYPE: PRT
<213> ORGANISM: Erwinia chrysanthemi

<400> SEQUENCE: 21

Met Gln Ile Thr Ile Lys Ala His Ile Gly Gly Asp Leu Gly Val Ser
1 5 10 15

-continued

```
Gly Leu Gly Ala Gln Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
    50                  55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
        115                 120                 125

Leu Ala Asn Ser Met Leu Asn Ala Ser Gln Met Thr Gln Gly Asn Met
    130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
            180                 185                 190

Gly Asn Ala Ile Gly Met Gly Val Gly Gln Asn Ala Ala Leu Ser Ala
        195                 200                 205

Leu Ser Asn Val Ser Thr His Val Asp Gly Asn Asn Arg His Phe Val
    210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
            260                 265                 270

Pro Asp Asp Asp Gly Met Thr Gly Ala Ser Met Asp Lys Phe Arg Gln
        275                 280                 285

Ala Met Gly Met Ile Lys Ser Ala Val Ala Gly Asp Thr Gly Asn Thr
    290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala
```

<210> SEQ ID NO 22
<211> LENGTH: 2141
<212> TYPE: DNA
<213> ORGANISM: Erwinia chrysanthemi

<400> SEQUENCE: 22

```
cgattttacc cgggtgaacg tgctatgacc gacagcatca cggtattcga caccgttacg      60

gcgtttatgg ccgcgatgaa ccggcatcag gcggcgcgct ggtcgccgca atccggcgtc     120

gatctggtat ttcagtttgg ggacaccggg cgtgaactca tgatgcagat tcagccgggg     180

cagcaatatc ccggcatgtt gcgcacgctg ctcgctcgtc gttatcagca ggcggcagag     240

tgcgatggct gccatctgtg cctgaacggc agcgatgtat tgatcctctg gtggccgctg     300
```

-continued

```
ccgtcggatc ccggcagtta tccgcaggtg atcgaacgtt tgtttgaact ggcgggaatg    360
acgttgccgt cgctatccat agcaccgacg gcgcgtccgc agacagggaa cggacgcgcc    420
cgatcattaa gataaaggcg gctttttttta ttgcaaaacg gtaacggtga ggaaccgttt    480
caccgtcggc gtcactcagt aacaagtatc catcatgatg cctacatcgg gatcggcgtg    540
ggcatccgtt gcagatactt ttgcgaacac ctgacatgaa tgaggaaacg aaattatgca    600
aattacgatc aaagcgcaca tcggcggtga tttgggcgtc tccggtctgg ggctgggtgc    660
tcagggactg aaaggactga attccgcggc ttcatcgctg ggttccagcg tggataaact    720
gagcagcacc atcgataagt tgacctccgc gctgacttcg atgatgtttg gcggcgcgct    780
ggcgcagggg ctgggcgcca gctcgaaggg gctggggatg agcaatcaac tgggccagtc    840
tttcggcaat ggcgcgcagg gtgcgagcaa cctgctatcc gtaccgaaat ccggcggcga    900
tgcgttgtca aaaatgtttg ataaagcgct ggacgatctg ctgggtcatg acaccgtgac    960
caagctgact aaccagagca accaactggc taattcaatg ctgaacgcca gccagatgac   1020
ccagggtaat atgaatgcgt tcggcagcgg tgtgaacaac gcactgtcgt ccattctcgg   1080
caacggtctc ggccagtcga tgagtggctt ctctcagcct tctctggggg caggcggctt   1140
gcagggcctg agcggcgcgg gtgcattcaa ccagttgggt aatgccatcg gcatgggcgt   1200
ggggcagaat gctgcgctga gtgcgttgag taacgtcagc acccacgtag acggtaacaa   1260
ccgccacttt gtagataaag aagatcgcgg catggcgaaa gagatcggcc agtttatgga   1320
tcagtatccg gaaatattcg gtaaaccgga ataccagaaa gatggctgga gttcgccgaa   1380
gacggacgac aaatcctggg ctaaagcgct gagtaaaccg gatgatgacg gtatgaccgg   1440
cgccagcatg gacaaattcc gtcaggcgat gggtatgatc aaaagcgcgg tggcgggtga   1500
taccggcaat accaacctga acctgcgtgg cgcgggcggt gcatcgctgg gtatcgatgc   1560
ggctgtcgtc ggcgataaaa tagccaacat gtcgctgggt aagctggcca acgcctgata   1620
atctgtgctg gcctgataaa gcggaaacga aaaaagagac ggggaagcct gtctcttttc   1680
ttattatgcg gtttatgcgg ttacctggac cggttaatca tcgtcatcga tctggtacaa   1740
acgcacattt tcccgttcat tcgcgtcgtt acgcgccaca atcgcgatgg catcttcctc   1800
gtcgctcaga ttgcgcggct gatggggaac gccgggtgga atatagagaa actcgccggc   1860
cagatggaga cacgtctgcg ataaatctgt gccgtaacgt gtttctatcc gcccctttag   1920
cagatagatt gcggtttcgt aatcaacatg gtaatgcggt tccgcctgtg cgccggccgg   1980
gatcaccaca atattcatag aaagctgtct tgcacctacc gtatcgcggg agataccgac   2040
aaaatagggc agtttttgcg tggtatccgt ggggtgttcc ggcctgacaa tcttgagttg   2100
gttcgtcatc atctttctcc atctgggcga cctgatcggt t                       2141
```

<210> SEQ ID NO 23
<211> LENGTH: 403
<212> TYPE: PRT
<213> ORGANISM: Erwinia amylovora

<400> SEQUENCE: 23

```
Met Ser Leu Asn Thr Ser Gly Leu Gly Ala Ser Thr Met Gln Ile Ser
  1               5                  10                  15

Ile Gly Gly Ala Gly Gly Asn Asn Gly Leu Leu Gly Thr Ser Arg Gln
             20                  25                  30

Asn Ala Gly Leu Gly Gly Asn Ser Ala Leu Gly Leu Gly Gly Gly Asn
         35                  40                  45
```

-continued

```
Gln Asn Asp Thr Val Asn Gln Leu Ala Gly Leu Leu Thr Gly Met Met
     50                  55                  60

Met Met Met Ser Met Met Gly Gly Gly Gly Leu Met Gly Gly Gly Leu
 65                  70                  75                  80

Gly Gly Gly Leu Gly Asn Gly Leu Gly Gly Ser Gly Gly Leu Gly Glu
                 85                  90                  95

Gly Leu Ser Asn Ala Leu Asn Asp Met Leu Gly Gly Ser Leu Asn Thr
            100                 105                 110

Leu Gly Ser Lys Gly Gly Asn Asn Thr Thr Ser Thr Thr Asn Ser Pro
        115                 120                 125

Leu Asp Gln Ala Leu Gly Ile Asn Ser Thr Ser Gln Asn Asp Asp Ser
    130                 135                 140

Thr Ser Gly Thr Asp Ser Thr Ser Asp Ser Ser Asp Pro Met Gln Gln
145                 150                 155                 160

Leu Leu Lys Met Phe Ser Glu Ile Met Gln Ser Leu Phe Gly Asp Gly
                165                 170                 175

Gln Asp Gly Thr Gln Gly Ser Ser Ser Gly Gly Lys Gln Pro Thr Glu
            180                 185                 190

Gly Glu Gln Asn Ala Tyr Lys Lys Gly Val Thr Asp Ala Leu Ser Gly
        195                 200                 205

Leu Met Gly Asn Gly Leu Ser Gln Leu Leu Gly Asn Gly Gly Leu Gly
    210                 215                 220

Gly Gly Gln Gly Gly Asn Ala Gly Thr Gly Leu Asp Gly Ser Ser Leu
225                 230                 235                 240

Gly Gly Lys Gly Leu Gln Asn Leu Ser Gly Pro Val Asp Tyr Gln Gln
                245                 250                 255

Leu Gly Asn Ala Val Gly Thr Gly Ile Gly Met Lys Ala Gly Ile Gln
            260                 265                 270

Ala Leu Asn Asp Ile Gly Thr His Arg His Ser Ser Thr Arg Ser Phe
        275                 280                 285

Val Asn Lys Gly Asp Arg Ala Met Ala Lys Glu Ile Gly Gln Phe Met
    290                 295                 300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330                 335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
        355                 360                 365

Gly Asn Leu Gln Ala Arg Gly Ala Gly Gly Ser Ser Leu Gly Ile Asp
    370                 375                 380

Ala Met Met Ala Gly Asp Ala Ile Asn Asn Met Ala Leu Gly Lys Leu
385                 390                 395                 400

Gly Ala Ala
```

<210> SEQ ID NO 24
<211> LENGTH: 1288
<212> TYPE: DNA
<213> ORGANISM: Erwinia amylovora

<400> SEQUENCE: 24
aagcttcggc atggcacgtt tgaccgttgg gtcggcaggg tacgtttgaa ttattcataa     60

-continued

```
gaggaatacg ttatgagtct gaatacaagt gggctgggag cgtcaacgat gcaaatttct    120

atcggcggtg cgggcggaaa taacgggttg ctgggtacca gtcgccagaa tgctgggttg    180

ggtggcaatt ctgcactggg gctgggcggc ggtaatcaaa atgataccgt caatcagctg    240

gctggcttac tcaccggcat gatgatgatg atgagcatga tgggcggtgg tgggctgatg    300

ggcggtggct taggcggtgg cttaggtaat ggcttgggtg gctcaggtgg cctgggcgaa    360

ggactgtcga acgcgctgaa cgatatgtta ggcggttcgc tgaacacgct gggctcgaaa    420

ggcggcaaca ataccacttc aacaacaaat tccccgctgg accaggcgct gggtattaac    480

tcaacgtccc aaaacgacga ttccacctcc ggcacagatt ccacctcaga ctccagcgac    540

ccgatgcagc agctgctgaa gatgttcagc gagataatgc aaagcctgtt tggtgatggg    600

caagatggca cccagggcag ttcctctggg ggcaagcagc cgaccgaagg cgagcagaac    660

gcctataaaa aaggagtcac tgatgcgctg tcgggcctga tgggtaatgg tctgagccag    720

ctccttggca acgggggact gggaggtggt cagggcggta atgctggcac gggtcttgac    780

ggttcgtcgc tgggcggcaa agggctgcaa aacctgagcg ggccggtgga ctaccagcag    840

ttaggtaacg ccgtgggtac cggtatcggt atgaaagcgg gcattcaggc gctgaatgat    900

atcggtacgc acaggcacag ttcaacccgt tctttcgtca ataaaggcga tcgggcgatg    960

gcgaaggaaa tcggtcagtt catggaccag tatcctgagg tgtttggcaa gccgcagtac   1020

cagaaaggcc cgggtcagga ggtgaaaacc gatgacaaat catgggcaaa agcactgagc   1080

aagccagatg acgacggaat gacaccagcc agtatggagc agttcaacaa agccaagggc   1140

atgatcaaaa ggcccatggc gggtgatacc ggcaacggca acctgcaggc acgcggtgcc   1200

ggtggttctt cgctgggtat tgatgccatg atggccggtg atgccattaa caatatggca   1260

cttggcaagc tgggcgcggc ttaagctt                                      1288
```

<210> SEQ ID NO 25
<211> LENGTH: 1344
<212> TYPE: DNA
<213> ORGANISM: Erwinia amylovora

<400> SEQUENCE: 25

```
atgtcaattc ttacgcttaa caacaatacc tcgtcctcgc cgggtctgtt ccagtccggg     60

ggggacaacg ggcttggtgg tcataatgca aattctgcgt tggggcaaca acccatcgat    120

cggcaaacca ttgagcaaat ggctcaatta ttggcggaac tgttaaagtc actgctatcg    180

ccacaatcag gtaatgcggc aaccggagcc ggtggcaatg accagactac aggagttggt    240

aacgctggcg gcctgaacgg acgaaaaggc acagcaggaa ccactccgca gtctgacagt    300

cagaacatgc tgagtgagat gggcaacaac gggctggatc aggccatcac gcccgatggc    360

cagggcggcg ggcagatcgg cgataatcct ttactgaaag ccatgctgaa gcttattgca    420

cgcatgatgg acggccaaag cgatcagttt ggccaacctg gtacgggcaa caacagtgcc    480

tcttccggta cttcttcatc tggcggttcc ccttttaacg atctatcagg ggggaaggcc    540

ccttccggca actccccttc cggcaactac tctcccgtca gtaccttctc acccccatcc    600

acgccaacgt cccctacctc accgcttgat ttcccttctt ctcccaccaa agcagccggg    660

ggcagcacgc cggtaaccga tcatcctgac cctgttggta gcgcgggcat cggggccgga    720

aattcggtgg ccttcaccag cgccggcgct aatcagacgg tgctgcatga caccattacc    780

gtgaaagcgg gtcaggtgtt tgatggcaaa ggacaaacct tcaccgccgg ttcagaatta    840

ggcgatggcg gccagtctga aaaccagaaa ccgctgttta tactggaaga cggtgccagc    900
```

-continued

```
ctgaaaaacg tcaccatggg cgacgacggg gcggatggta ttcatcttta cggtgatgcc    960

aaaatagaca atctgcacgt caccaacgtg ggtgaggacg cgattaccgt taagccaaac   1020

agcgcgggca aaaaatccca cgttgaaatc actaacagtt ccttcgagca cgcctctgac   1080

aagatcctgc agctgaatgc cgatactaac ctgagcgttg acaacgtgaa ggccaaagac   1140

tttggtactt ttgtacgcac taacggcggt caacagggta actgggatct gaatctgagc   1200

catatcagcg cagaagacgg taagttctcg ttcgttaaaa gcgatagcga ggggctaaac   1260

gtcaatacca gtgatatctc actgggtgat gttgaaaacc actacaaagt gccgatgtcc   1320

gccaacctga aggtggctga atga                                          1344


<210> SEQ ID NO 26
<211> LENGTH: 447
<212> TYPE: PRT
<213> ORGANISM: Erwinia amylovora

<400> SEQUENCE: 26

Met Ser Ile Leu Thr Leu Asn Asn Asn Thr Ser Ser Ser Pro Gly Leu
  1               5                  10                  15

Phe Gln Ser Gly Gly Asp Asn Gly Leu Gly Gly His Asn Ala Asn Ser
             20                  25                  30

Ala Leu Gly Gln Gln Pro Ile Asp Arg Gln Thr Ile Glu Gln Met Ala
         35                  40                  45

Gln Leu Leu Ala Glu Leu Leu Lys Ser Leu Leu Ser Pro Gln Ser Gly
     50                  55                  60

Asn Ala Ala Thr Gly Ala Gly Gly Asn Asp Gln Thr Thr Gly Val Gly
 65                  70                  75                  80

Asn Ala Gly Gly Leu Asn Gly Arg Lys Gly Thr Ala Gly Thr Thr Pro
                 85                  90                  95

Gln Ser Asp Ser Gln Asn Met Leu Ser Glu Met Gly Asn Asn Gly Leu
            100                 105                 110

Asp Gln Ala Ile Thr Pro Asp Gly Gln Gly Gly Gly Gln Ile Gly Asp
        115                 120                 125

Asn Pro Leu Leu Lys Ala Met Leu Lys Leu Ile Ala Arg Met Met Asp
    130                 135                 140

Gly Gln Ser Asp Gln Phe Gly Gln Pro Gly Thr Gly Asn Asn Ser Ala
145                 150                 155                 160

Ser Ser Gly Thr Ser Ser Ser Gly Gly Ser Pro Phe Asn Asp Leu Ser
                165                 170                 175

Gly Gly Lys Ala Pro Ser Gly Asn Ser Pro Ser Gly Asn Tyr Ser Pro
            180                 185                 190

Val Ser Thr Phe Ser Pro Pro Ser Thr Pro Thr Ser Pro Thr Ser Pro
        195                 200                 205

Leu Asp Phe Pro Ser Ser Pro Thr Lys Ala Ala Gly Gly Ser Thr Pro
    210                 215                 220

Val Thr Asp His Pro Asp Pro Val Gly Ser Ala Gly Ile Gly Ala Gly
225                 230                 235                 240

Asn Ser Val Ala Phe Thr Ser Ala Gly Ala Asn Gln Thr Val Leu His
                245                 250                 255

Asp Thr Ile Thr Val Lys Ala Gly Gln Val Phe Asp Gly Lys Gly Gln
            260                 265                 270

Thr Phe Thr Ala Gly Ser Glu Leu Gly Asp Gly Gly Gln Ser Glu Asn
        275                 280                 285
```

-continued

```
Gln Lys Pro Leu Phe Ile Leu Glu Asp Gly Ala Ser Leu Lys Asn Val
    290                 295                 300

Thr Met Gly Asp Asp Gly Ala Asp Gly Ile His Leu Tyr Gly Asp Ala
305                 310                 315                 320

Lys Ile Asp Asn Leu His Val Thr Asn Val Gly Glu Asp Ala Ile Thr
                325                 330                 335

Val Lys Pro Asn Ser Ala Gly Lys Lys Ser His Val Glu Ile Thr Asn
            340                 345                 350

Ser Ser Phe Glu His Ala Ser Asp Lys Ile Leu Gln Leu Asn Ala Asp
        355                 360                 365

Thr Asn Leu Ser Val Asp Asn Val Lys Ala Lys Asp Phe Gly Thr Phe
    370                 375                 380

Val Arg Thr Asn Gly Gly Gln Gln Gly Asn Trp Asp Leu Asn Leu Ser
385                 390                 395                 400

His Ile Ser Ala Glu Asp Gly Lys Phe Ser Phe Val Lys Ser Asp Ser
                405                 410                 415

Glu Gly Leu Asn Val Asn Thr Ser Asp Ile Ser Leu Gly Asp Val Glu
            420                 425                 430

Asn His Tyr Lys Val Pro Met Ser Ala Asn Leu Lys Val Ala Glu
        435                 440                 445


<210> SEQ ID NO 27
<211> LENGTH: 5517
<212> TYPE: DNA
<213> ORGANISM: Erwinia amylovora

<400> SEQUENCE: 27

atggaattaa aatcactggg aactgaacac aaggcggcag tacacacagc ggcgcacaac      60

cctgtggggc atggtgttgc cttacagcag ggcagcagca gcagcagccc gcaaaatgcc     120

gctgcatcat tggcggcaga aggcaaaaat cgtgggaaaa tgccgagaat tcaccagcca     180

tctactgcgg ctgatggtat cagcgctgct caccagcaaa agaaatcctt cagtctcagg     240

ggctgtttgg ggacgaaaaa attttccaga tcggcaccgc agggccagcc aggtaccacc     300

cacagcaaag gggcaacatt gcgcgatctg ctggcgcggg acgacggcga aacgcagcat     360

gaggcggccg cgccagatgc ggcgcgtttg acccgttcgg gcggcgtcaa acgccgcaat     420

atggacgaca tggccgggcg gccaatggtg aaaggtggca gcggcgaaga taaggtacca     480

acgcagcaaa aacggcatca gctgaacaat tttggccaga tgcgccaaac gatgttgagc     540

aaaatggctc acccggcttc agccaacgcc ggcgatcgcc tgcagcattc accgccgcac     600

atcccgggta gccaccacga aatcaaggaa gaaccggttg gctccaccag caaggcaaca     660

acggcccacg cagacagagt ggaaatcgct caggaagatg acgacagcga attccagcaa     720

ctgcatcaac agcggctggc gcgcgaacgg gaaaatccac cgcagccgcc caaactcggc     780

gttgccacac cgattagcgc caggtttcag cccaaactga ctgcggttgc ggaaagcgtc     840

cttgagggga cagataccac gcagtcaccc cttaagccgc aatcaatgct gaaaggaagt     900

ggagccgggg taacgccgct ggcggtaacg ctggataaag gcaagttgca gctggcaccg     960

gataatccac ccgcgctcaa tacgttgttg aagcagacat tgggtaaaga cacccagcac    1020

tatctggcgc accatgccag cagcgacggt agccagcatc tgctgctgga caacaaaggc    1080

cacctgtttg atatcaaaag caccgccacc agctatagcg tgctgcacaa cagccacccc    1140

ggtgagataa agggcaagct ggcgcaggcg ggtactggct ccgtcagcgt agacggtaaa    1200

agcggcaaga tctcgctggg gagcggtacg caaagtcaca acaaaacaat gctaagccaa    1260
```

-continued

```
ccgggggaag cgcaccgttc cttattaacc ggcatttggc agcatcctgc tggcgcagcg   1320
cggccgcagg gcgagtcaat ccgcctgcat gacgacaaaa ttcatatcct gcatccggag   1380
ctgggcgtat ggcaatctgc ggataaagat acccacagcc agctgtctcg ccaggcagac   1440
ggtaagctct atgcgctgaa agacaaccgt accctgcaaa acctctccga taataaatcc   1500
tcagaaaagc tggtcgataa aatcaaatcg tattccgttg atcagcgggg gcaggtggcg   1560
atcctgacgg atactcccgg ccgccataag atgagtatta tgccctcgct ggatgcttcc   1620
ccggagagcc atatttccct cagcctgcat tttgccgatg cccaccaggg gttattgcac   1680
gggaagtcgg agcttgaggc acaatctgtc gcgatcagcc atgggcgact ggttgtggcc   1740
gatagcgaag gcaagctgtt tagcgccgcc attccgaagc aaggggatgg aaacgaactg   1800
aaaatgaaag ccatgcctca gcatgcgctc gatgaacatt ttggtcatga ccaccagatt   1860
tctggatttt tccatgacga ccacggccag cttaatgcgc tggtgaaaaa taacttcagg   1920
cagcagcatg cctgcccgtt gggtaacgat catcagtttc accccggctg gaacctgact   1980
gatgcgctgg ttatcgacaa tcagctgggg ctgcatcata ccaatcctga accgcatgag   2040
attcttgata tggggcattt aggcagcctg gcgttacagg agggcaagct tcactatttt   2100
gaccagctga ccaaagggtg gactggcgcg gagtcagatt gtaagcagct gaaaaaaggc   2160
ctggatggag cagcttatct actgaaagac ggtgaagtga aacgcctgaa tattaatcag   2220
agcacctcct ctatcaagca cggaacggaa aacgtttttt cgctgccgca tgtgcgcaat   2280
aaaccggagc cgggagatgc cctgcaaggg ctgaataaag acgataaggc ccaggccatg   2340
gcggtgattg ggtaaataa atacctggcg ctgacggaaa aaggggacat tcgctccttc   2400
cagataaaac ccggcaccca gcagttggag cggccggcac aaactctcag ccgcgaaggt   2460
atcagcggcg aactgaaaga cattcatgtc gaccacaagc agaacctgta tgccttgacc   2520
cacgagggag aggtgtttca tcagccgcgt gaagcctggc agaatggtgc cgaaagcagc   2580
agctggcaca aactggcgtt gccacagagt gaaagtaagc taaaaagtct ggacatgagc   2640
catgagcaca aaccgattgc cacctttgaa gacggtagcc agcatcagct gaaggctggc   2700
ggctggcacg cctatgcggc acctgaacgc gggccgctgg cggtgggtac cagcggttca   2760
caaaccgtct ttaaccgact aatgcagggg gtgaaaggca aggtgatccc aggcagcggg   2820
ttgacggtta agctctcggc tcagacgggg ggaatgaccg gcgccgaagg gcgcaaggtc   2880
agcagtaaat tttccgaaag gatccgcgcc tatgcgttca acccaacaat gtccacgccg   2940
cgaccgatta aaaatgctgc ttatgccaca cagcacggct ggcaggggcg tgaggggttg   3000
aagccgttgt acgagatgca gggagcgctg attaaacaac tggatgcgca taacgttcgt   3060
cataacgcgc cacagccaga tttgcagagc aaactggaaa ctctggattt aggcgaacat   3120
ggcgcagaat tgcttaacga catgaagcgc ttccgcgacg aactggagca gagtgcaacc   3180
cgttcggtga ccgttttagg tcaacatcag ggagtgctaa aaagcaacgg tgaaatcaat   3240
agcgaattta agccatcgcc cggcaaggcg ttggtccaga gctttaacgt caatcgctct   3300
ggtcaggatc taagcaagtc actgcaacag gcagtacatg ccacgccgcc atccgcagag   3360
agtaaactgc aatccatgct ggggcacttt gtcagtgccg gggtggatat gagtcatcag   3420
aagggcgaga tcccgctggg ccgccagcgc gatccgaatg ataaaaccgc actgaccaaa   3480
tcgcgtttaa ttttagatac cgtgaccatc ggtgaactgc atgaactggc cgataaggcg   3540
aaactggtat ctgaccataa acccgatgcc gatcagataa aacagctgcg ccagcagttc   3600
```

-continued

```
gatacgctgc gtgaaaagcg gtatgagagc aatccggtga agcattacac cgatatgggc   3660

ttcacccata ataaggcgct ggaagcaaac tatgatgcgg tcaaagcctt tatcaatgcc   3720

tttaagaaag agcaccacgg cgtcaatctg accacgcgta ccgtactgga atcacagggc   3780

agtgcggagc tggcgaagaa gctcaagaat acgctgttgt ccctggacag tggtgaaagt   3840

atgagcttca gccggtcata tggcgggggc gtcagcactg tctttgtgcc tacccttagc   3900

aagaaggtgc cagttccggt gatccccgga gccggcatca cgctggatcg cgcctataac   3960

ctgagcttca gtcgtaccag cggcggattg aacgtcagtt ttggccgcga cggcggggtg   4020

agtggtaaca tcatggtcgc taccggccat gatgtgatgc cctatatgac cggtaagaaa   4080

accagtgcag gtaacgccag tgactggttg agcgcaaaac ataaaatcag cccggacttg   4140

cgtatcggcg ctgctgtgag tggcaccctg caaggaacgc tacaaaacag cctgaagttt   4200

aagctgacag aggatgagct gcctggcttt atccatggct tgacgcatgg cacgttgacc   4260

ccggcagaac tgttgcaaaa ggggatcgaa catcagatga agcagggcag caaactgacg   4320

tttagcgtcg atacctcggc aaatctggat ctgcgtgccg gtatcaatct gaacgaagac   4380

ggcagtaaac caaatggtgt cactgcccgt gtttctgccg ggctaagtgc atcggcaaac   4440

ctggccgccg gctcgcgtga acgcagcacc acctctggcc agtttggcag cacgacttcg   4500

gccagcaata accgcccaac cttcctcaac ggggtcggcg cgggtgctaa cctgacggct   4560

gctttagggg ttgcccattc atctacgcat gaagggaaac cggtcgggat cttcccggca   4620

tttacctcga ccaatgtttc ggcagcgctg gcgctggata accgtacctc acagagtatc   4680

agcctggaat tgaagcgcgc ggagccggtg accagcaacg atatcagcga gttgacctcc   4740

acgctgggaa aacactttaa ggatagcgcc acaacgaaga tgcttgccgc tctcaaagag   4800

ttagatgacg ctaagcccgc tgaacaactg catattttac agcagcattt cagtgcaaaa   4860

gatgtcgtcg gtgatgaacg ctacgaggcg gtgcgcaacc tgaaaaaact ggtgatacgt   4920

caacaggctg cggacagcca cagcatggaa ttaggatctg ccagtcacag cacgacctac   4980

aataatctgt cgagaataaa taatgacggc attgtcgagc tgctacacaa acatttcgat   5040

gcggcattac cagcaagcag tgccaaacgt cttggtgaaa tgatgaataa cgatccggca   5100

ctgaaagata ttattaagca gctgcaaagt acgccgttca gcagcgccag cgtgtcgatg   5160

gagctgaaag atggtctgcg tgagcagacg gaaaaagcaa tactggacgg taaggtcggt   5220

cgtgaagaag tgggagtact tttccaggat cgtaacaact tgcgtgttaa atcggtcagc   5280

gtcagtcagt ccgtcagcaa aagcgaaggc ttcaataccc cagcgctgtt actggggacg   5340

agcaacagcg ctgctatgag catggagcgc aacatcggaa ccattaattt taaatacggc   5400

caggatcaga acaccccacg gcgatttacc ctggagggtg gaatagctca ggctaatccg   5460

caggtcgcat ctgcgcttac tgatttgaag aaggaagggc tggaaatgaa gagctaa      5517
```

<210> SEQ ID NO 28
<211> LENGTH: 1838
<212> TYPE: PRT
<213> ORGANISM: Erwinia amylovora

<400> SEQUENCE: 28

```
Met Glu Leu Lys Ser Leu Gly Thr Glu His Lys Ala Ala Val His Thr
  1               5                  10                  15

Ala Ala His Asn Pro Val Gly His Gly Val Ala Leu Gln Gln Gly Ser
             20                  25                  30

Ser Ser Ser Ser Pro Gln Asn Ala Ala Ala Ser Leu Ala Ala Glu Gly
```

-continued

```
            35                  40                  45

Lys Asn Arg Gly Lys Met Pro Arg Ile His Gln Pro Ser Thr Ala Ala
    50                  55                  60

Asp Gly Ile Ser Ala Ala His Gln Gln Lys Lys Ser Phe Ser Leu Arg
65                  70                  75                  80

Gly Cys Leu Gly Thr Lys Lys Phe Ser Arg Ser Ala Pro Gln Gly Gln
                85                  90                  95

Pro Gly Thr Thr His Ser Lys Gly Ala Thr Leu Arg Asp Leu Leu Ala
            100                 105                 110

Arg Asp Asp Gly Glu Thr Gln His Glu Ala Ala Ala Pro Asp Ala Ala
        115                 120                 125

Arg Leu Thr Arg Ser Gly Gly Val Lys Arg Arg Asn Met Asp Asp Met
    130                 135                 140

Ala Gly Arg Pro Met Val Lys Gly Gly Ser Gly Glu Asp Lys Val Pro
145                 150                 155                 160

Thr Gln Gln Lys Arg His Gln Leu Asn Asn Phe Gly Gln Met Arg Gln
                165                 170                 175

Thr Met Leu Ser Lys Met Ala His Pro Ala Ser Ala Asn Ala Gly Asp
            180                 185                 190

Arg Leu Gln His Ser Pro Pro His Ile Pro Gly Ser His His Glu Ile
        195                 200                 205

Lys Glu Glu Pro Val Gly Ser Thr Ser Lys Ala Thr Thr Ala His Ala
    210                 215                 220

Asp Arg Val Glu Ile Ala Gln Glu Asp Asp Asp Ser Glu Phe Gln Gln
225                 230                 235                 240

Leu His Gln Gln Arg Leu Ala Arg Glu Arg Glu Asn Pro Pro Gln Pro
                245                 250                 255

Pro Lys Leu Gly Val Ala Thr Pro Ile Ser Ala Arg Phe Gln Pro Lys
            260                 265                 270

Leu Thr Ala Val Ala Glu Ser Val Leu Glu Gly Thr Asp Thr Thr Gln
        275                 280                 285

Ser Pro Leu Lys Pro Gln Ser Met Leu Lys Gly Ser Gly Ala Gly Val
    290                 295                 300

Thr Pro Leu Ala Val Thr Leu Asp Lys Gly Lys Leu Gln Leu Ala Pro
305                 310                 315                 320

Asp Asn Pro Pro Ala Leu Asn Thr Leu Leu Lys Gln Thr Leu Gly Lys
                325                 330                 335

Asp Thr Gln His Tyr Leu Ala His His Ala Ser Ser Asp Gly Ser Gln
            340                 345                 350

His Leu Leu Leu Asp Asn Lys Gly His Leu Phe Asp Ile Lys Ser Thr
        355                 360                 365

Ala Thr Ser Tyr Ser Val Leu His Asn Ser His Pro Gly Glu Ile Lys
    370                 375                 380

Gly Lys Leu Ala Gln Ala Gly Thr Gly Ser Val Ser Val Asp Gly Lys
385                 390                 395                 400

Ser Gly Lys Ile Ser Leu Gly Ser Gly Thr Gln Ser His Asn Lys Thr
                405                 410                 415

Met Leu Ser Gln Pro Gly Glu Ala His Arg Ser Leu Leu Thr Gly Ile
            420                 425                 430

Trp Gln His Pro Ala Gly Ala Ala Arg Pro Gln Gly Glu Ser Ile Arg
        435                 440                 445

Leu His Asp Asp Lys Ile His Ile Leu His Pro Glu Leu Gly Val Trp
    450                 455                 460
```

-continued

```
Gln Ser Ala Asp Lys Asp Thr His Ser Gln Leu Ser Arg Gln Ala Asp
465                 470                 475                 480

Gly Lys Leu Tyr Ala Leu Lys Asp Asn Arg Thr Leu Gln Asn Leu Ser
                485                 490                 495

Asp Asn Lys Ser Ser Glu Lys Leu Val Asp Lys Ile Lys Ser Tyr Ser
            500                 505                 510

Val Asp Gln Arg Gly Gln Val Ala Ile Leu Thr Asp Thr Pro Gly Arg
        515                 520                 525

His Lys Met Ser Ile Met Pro Ser Leu Asp Ala Ser Pro Glu Ser His
    530                 535                 540

Ile Ser Leu Ser Leu His Phe Ala Asp Ala His Gln Gly Leu Leu His
545                 550                 555                 560

Gly Lys Ser Glu Leu Glu Ala Gln Ser Val Ala Ile Ser His Gly Arg
                565                 570                 575

Leu Val Val Ala Asp Ser Glu Gly Lys Leu Phe Ser Ala Ala Ile Pro
            580                 585                 590

Lys Gln Gly Asp Gly Asn Glu Leu Lys Met Lys Ala Met Pro Gln His
        595                 600                 605

Ala Leu Asp Glu His Phe Gly His Asp His Gln Ile Ser Gly Phe Phe
    610                 615                 620

His Asp Asp His Gly Gln Leu Asn Ala Leu Val Lys Asn Asn Phe Arg
625                 630                 635                 640

Gln Gln His Ala Cys Pro Leu Gly Asn Asp His Gln Phe His Pro Gly
                645                 650                 655

Trp Asn Leu Thr Asp Ala Leu Val Ile Asp Asn Gln Leu Gly Leu His
            660                 665                 670

His Thr Asn Pro Glu Pro His Glu Ile Leu Asp Met Gly His Leu Gly
        675                 680                 685

Ser Leu Ala Leu Gln Glu Gly Lys Leu His Tyr Phe Asp Gln Leu Thr
    690                 695                 700

Lys Gly Trp Thr Gly Ala Glu Ser Asp Cys Lys Gln Leu Lys Lys Gly
705                 710                 715                 720

Leu Asp Gly Ala Ala Tyr Leu Leu Lys Asp Gly Glu Val Lys Arg Leu
                725                 730                 735

Asn Ile Asn Gln Ser Thr Ser Ser Ile Lys His Gly Thr Glu Asn Val
            740                 745                 750

Phe Ser Leu Pro His Val Arg Asn Lys Pro Glu Pro Gly Asp Ala Leu
        755                 760                 765

Gln Gly Leu Asn Lys Asp Asp Lys Ala Gln Ala Met Ala Val Ile Gly
    770                 775                 780

Val Asn Lys Tyr Leu Ala Leu Thr Glu Lys Gly Asp Ile Arg Ser Phe
785                 790                 795                 800

Gln Ile Lys Pro Gly Thr Gln Gln Leu Glu Arg Pro Ala Gln Thr Leu
                805                 810                 815

Ser Arg Glu Gly Ile Ser Gly Glu Leu Lys Asp Ile His Val Asp His
            820                 825                 830

Lys Gln Asn Leu Tyr Ala Leu Thr His Glu Gly Glu Val Phe His Gln
        835                 840                 845

Pro Arg Glu Ala Trp Gln Asn Gly Ala Glu Ser Ser Ser Trp His Lys
    850                 855                 860

Leu Ala Leu Pro Gln Ser Glu Ser Lys Leu Lys Ser Leu Asp Met Ser
865                 870                 875                 880
```

-continued

```
His Glu His Lys Pro Ile Ala Thr Phe Glu Asp Gly Ser Gln His Gln
                885                 890                 895

Leu Lys Ala Gly Gly Trp His Ala Tyr Ala Ala Pro Glu Arg Gly Pro
            900                 905                 910

Leu Ala Val Gly Thr Ser Gly Ser Gln Thr Val Phe Asn Arg Leu Met
        915                 920                 925

Gln Gly Val Lys Gly Lys Val Ile Pro Gly Ser Gly Leu Thr Val Lys
    930                 935                 940

Leu Ser Ala Gln Thr Gly Gly Met Thr Gly Ala Glu Gly Arg Lys Val
945                 950                 955                 960

Ser Ser Lys Phe Ser Glu Arg Ile Arg Ala Tyr Ala Phe Asn Pro Thr
                965                 970                 975

Met Ser Thr Pro Arg Pro Ile Lys Asn Ala Ala Tyr Ala Thr Gln His
            980                 985                 990

Gly Trp Gln Gly Arg Glu Gly Leu Lys Pro Leu Tyr Glu Met Gln Gly
        995                 1000                1005

Ala Leu Ile Lys Gln Leu Asp Ala His Asn Val Arg His Asn Ala Pro
   1010                 1015                1020

Gln Pro Asp Leu Gln Ser Lys Leu Glu Thr Leu Asp Leu Gly Glu His
1025                1030                1035                1040

Gly Ala Glu Leu Leu Asn Asp Met Lys Arg Phe Arg Asp Glu Leu Glu
               1045                1050                1055

Gln Ser Ala Thr Arg Ser Val Thr Val Leu Gly Gln His Gln Gly Val
           1060                1065                1070

Leu Lys Ser Asn Gly Glu Ile Asn Ser Glu Phe Lys Pro Ser Pro Gly
       1075                1080                1085

Lys Ala Leu Val Gln Ser Phe Asn Val Asn Arg Ser Gly Gln Asp Leu
   1090                1095                1100

Ser Lys Ser Leu Gln Gln Ala Val His Ala Thr Pro Pro Ser Ala Glu
1105                1110                1115                1120

Ser Lys Leu Gln Ser Met Leu Gly His Phe Val Ser Ala Gly Val Asp
               1125                1130                1135

Met Ser His Gln Lys Gly Glu Ile Pro Leu Gly Arg Gln Arg Asp Pro
           1140                1145                1150

Asn Asp Lys Thr Ala Leu Thr Lys Ser Arg Leu Ile Leu Asp Thr Val
       1155                1160                1165

Thr Ile Gly Glu Leu His Glu Leu Ala Asp Lys Ala Lys Leu Val Ser
   1170                1175                1180

Asp His Lys Pro Asp Ala Asp Gln Ile Lys Gln Leu Arg Gln Gln Phe
1185                1190                1195                1200

Asp Thr Leu Arg Glu Lys Arg Tyr Glu Ser Asn Pro Val Lys His Tyr
               1205                1210                1215

Thr Asp Met Gly Phe Thr His Asn Lys Ala Leu Glu Ala Asn Tyr Asp
           1220                1225                1230

Ala Val Lys Ala Phe Ile Asn Ala Phe Lys Lys Glu His His Gly Val
       1235                1240                1245

Asn Leu Thr Thr Arg Thr Val Leu Glu Ser Gln Gly Ser Ala Glu Leu
   1250                1255                1260

Ala Lys Lys Leu Lys Asn Thr Leu Leu Ser Leu Asp Ser Gly Glu Ser
1265                1270                1275                1280

Met Ser Phe Ser Arg Ser Tyr Gly Gly Gly Val Ser Thr Val Phe Val
               1285                1290                1295

Pro Thr Leu Ser Lys Lys Val Pro Val Pro Val Ile Pro Gly Ala Gly
```

-continued 1300 1305 1310

Ile Thr Leu Asp Arg Ala Tyr Asn Leu Ser Phe Ser Arg Thr Ser Gly
1315 1320 1325

Gly Leu Asn Val Ser Phe Gly Arg Asp Gly Gly Val Ser Gly Asn Ile
1330 1335 1340

Met Val Ala Thr Gly His Asp Val Met Pro Tyr Met Thr Gly Lys Lys
1345 1350 1355 1360

Thr Ser Ala Gly Asn Ala Ser Asp Trp Leu Ser Ala Lys His Lys Ile
1365 1370 1375

Ser Pro Asp Leu Arg Ile Gly Ala Ala Val Ser Gly Thr Leu Gln Gly
1380 1385 1390

Thr Leu Gln Asn Ser Leu Lys Phe Lys Leu Thr Glu Asp Glu Leu Pro
1395 1400 1405

Gly Phe Ile His Gly Leu Thr His Gly Thr Leu Thr Pro Ala Glu Leu
1410 1415 1420

Leu Gln Lys Gly Ile Glu His Gln Met Lys Gln Gly Ser Lys Leu Thr
1425 1430 1435 1440

Phe Ser Val Asp Thr Ser Ala Asn Leu Asp Leu Arg Ala Gly Ile Asn
1445 1450 1455

Leu Asn Glu Asp Gly Ser Lys Pro Asn Gly Val Thr Ala Arg Val Ser
1460 1465 1470

Ala Gly Leu Ser Ala Ser Ala Asn Leu Ala Ala Gly Ser Arg Glu Arg
1475 1480 1485

Ser Thr Thr Ser Gly Gln Phe Gly Ser Thr Thr Ser Ala Ser Asn Asn
1490 1495 1500

Arg Pro Thr Phe Leu Asn Gly Val Gly Ala Gly Ala Asn Leu Thr Ala
1505 1510 1515 1520

Ala Leu Gly Val Ala His Ser Ser Thr His Glu Gly Lys Pro Val Gly
1525 1530 1535

Ile Phe Pro Ala Phe Thr Ser Thr Asn Val Ser Ala Ala Leu Ala Leu
1540 1545 1550

Asp Asn Arg Thr Ser Gln Ser Ile Ser Leu Glu Leu Lys Arg Ala Glu
1555 1560 1565

Pro Val Thr Ser Asn Asp Ile Ser Glu Leu Thr Ser Thr Leu Gly Lys
1570 1575 1580

His Phe Lys Asp Ser Ala Thr Thr Lys Met Leu Ala Ala Leu Lys Glu
1585 1590 1595 1600

Leu Asp Asp Ala Lys Pro Ala Glu Gln Leu His Ile Leu Gln Gln His
1605 1610 1615

Phe Ser Ala Lys Asp Val Val Gly Asp Glu Arg Tyr Glu Ala Val Arg
1620 1625 1630

Asn Leu Lys Lys Leu Val Ile Arg Gln Gln Ala Ala Asp Ser His Ser
1635 1640 1645

Met Glu Leu Gly Ser Ala Ser His Ser Thr Thr Tyr Asn Asn Leu Ser
1650 1655 1660

Arg Ile Asn Asn Asp Gly Ile Val Glu Leu Leu His Lys His Phe Asp
1665 1670 1675 1680

Ala Ala Leu Pro Ala Ser Ser Ala Lys Arg Leu Gly Glu Met Met Asn
1685 1690 1695

Asn Asp Pro Ala Leu Lys Asp Ile Ile Lys Gln Leu Gln Ser Thr Pro
1700 1705 1710

Phe Ser Ser Ala Ser Val Ser Met Glu Leu Lys Asp Gly Leu Arg Glu
1715 1720 1725

-continued

```
Gln Thr Glu Lys Ala Ile Leu Asp Gly Lys Val Gly Arg Glu Glu Val
   1730                1735                1740

Gly Val Leu Phe Gln Asp Arg Asn Asn Leu Arg Val Lys Ser Val Ser
1745                1750                1755                1760

Val Ser Gln Ser Val Ser Lys Ser Glu Gly Phe Asn Thr Pro Ala Leu
               1765                1770                1775

Leu Leu Gly Thr Ser Asn Ser Ala Ala Met Ser Met Glu Arg Asn Ile
           1780                1785                1790

Gly Thr Ile Asn Phe Lys Tyr Gly Gln Asp Gln Asn Thr Pro Arg Arg
       1795                1800                1805

Phe Thr Leu Glu Gly Gly Ile Ala Gln Ala Asn Pro Gln Val Ala Ser
   1810                1815                1820

Ala Leu Thr Asp Leu Lys Lys Glu Gly Leu Glu Met Lys Ser
1825                1830                1835


<210> SEQ ID NO 29
<211> LENGTH: 420
<212> TYPE: DNA
<213> ORGANISM: Erwinia amylovora

<400> SEQUENCE: 29

atgacatcgt cacagcagcg ggttgaaagg tttttacagt atttctccgc cgggtgtaaa      60

acgcccatac atctgaaaga cggggtgtgc gccctgtata acgaacaaga tgaggaggcg     120

gcggtgctgg aagtaccgca acacagcgac agcctgttac tacactgccg aatcattgag     180

gctgacccac aaacttcaat aaccctgtat tcgatgctat tacagctgaa ttttgaaatg     240

gcggccatgc gcggctgttg gctggcgctg gatgaactgc acaacgtgcg tttatgtttt     300

cagcagtcgc tggagcatct ggatgaagca agttttagcg atatcgttag cggcttcatc     360

gaacatgcgg cagaagtgcg tgagtatata gcgcaattag acgagagtag cgcggcataa     420


<210> SEQ ID NO 30
<211> LENGTH: 139
<212> TYPE: PRT
<213> ORGANISM: Erwinia amylovora

<400> SEQUENCE: 30

Met Thr Ser Ser Gln Gln Arg Val Glu Arg Phe Leu Gln Tyr Phe Ser
  1               5                  10                  15

Ala Gly Cys Lys Thr Pro Ile His Leu Lys Asp Gly Val Cys Ala Leu
             20                  25                  30

Tyr Asn Glu Gln Asp Glu Glu Ala Ala Val Leu Glu Val Pro Gln His
         35                  40                  45

Ser Asp Ser Leu Leu Leu His Cys Arg Ile Ile Glu Ala Asp Pro Gln
     50                  55                  60

Thr Ser Ile Thr Leu Tyr Ser Met Leu Leu Gln Leu Asn Phe Glu Met
 65                  70                  75                  80

Ala Ala Met Arg Gly Cys Trp Leu Ala Leu Asp Glu Leu His Asn Val
                 85                  90                  95

Arg Leu Cys Phe Gln Gln Ser Leu Glu His Leu Asp Glu Ala Ser Phe
            100                 105                 110

Ser Asp Ile Val Ser Gly Phe Ile Glu His Ala Ala Glu Val Arg Glu
        115                 120                 125

Tyr Ile Ala Gln Leu Asp Glu Ser Ser Ala Ala
    130                 135
```

-continued

<210> SEQ ID NO 31
<211> LENGTH: 341
<212> TYPE: PRT
<213> ORGANISM: Pseudomonas syringae

<400> SEQUENCE: 31

```
Met Gln Ser Leu Ser Leu Asn Ser Ser Ser Leu Gln Thr Pro Ala Met
  1               5                  10                  15

Ala Leu Val Leu Val Arg Pro Glu Ala Glu Thr Thr Gly Ser Thr Ser
             20                  25                  30

Ser Lys Ala Leu Gln Glu Val Val Val Lys Leu Ala Glu Glu Leu Met
         35                  40                  45

Arg Asn Gly Gln Leu Asp Asp Ser Ser Pro Leu Gly Lys Leu Leu Ala
     50                  55                  60

Lys Ser Met Ala Ala Asp Gly Lys Ala Gly Gly Gly Ile Glu Asp Val
 65                  70                  75                  80

Ile Ala Ala Leu Asp Lys Leu Ile His Glu Lys Leu Gly Asp Asn Phe
                 85                  90                  95

Gly Ala Ser Ala Asp Ser Ala Ser Gly Thr Gly Gln Gln Asp Leu Met
            100                 105                 110

Thr Gln Val Leu Asn Gly Leu Ala Lys Ser Met Leu Asp Asp Leu Leu
        115                 120                 125

Thr Lys Gln Asp Gly Gly Thr Ser Phe Ser Glu Asp Asp Met Pro Met
    130                 135                 140

Leu Asn Lys Ile Ala Gln Phe Met Asp Asp Asn Pro Ala Gln Phe Pro
145                 150                 155                 160

Lys Pro Asp Ser Gly Ser Trp Val Asn Glu Leu Lys Glu Asp Asn Phe
                165                 170                 175

Leu Asp Gly Asp Glu Thr Ala Ala Phe Arg Ser Ala Leu Asp Ile Ile
            180                 185                 190

Gly Gln Gln Leu Gly Asn Gln Gln Ser Asp Ala Gly Ser Leu Ala Gly
        195                 200                 205

Thr Gly Gly Gly Leu Gly Thr Pro Ser Ser Phe Ser Asn Asn Ser Ser
    210                 215                 220

Val Met Gly Asp Pro Leu Ile Asp Ala Asn Thr Gly Pro Gly Asp Ser
225                 230                 235                 240

Gly Asn Thr Arg Gly Glu Ala Gly Gln Leu Ile Gly Glu Leu Ile Asp
                245                 250                 255

Arg Gly Leu Gln Ser Val Leu Ala Gly Gly Gly Leu Gly Thr Pro Val
            260                 265                 270

Asn Thr Pro Gln Thr Gly Thr Ser Ala Asn Gly Gly Gln Ser Ala Gln
        275                 280                 285

Asp Leu Asp Gln Leu Leu Gly Gly Leu Leu Leu Lys Gly Leu Glu Ala
    290                 295                 300

Thr Leu Lys Asp Ala Gly Gln Thr Gly Thr Asp Val Gln Ser Ser Ala
305                 310                 315                 320

Ala Gln Ile Ala Thr Leu Leu Val Ser Thr Leu Leu Gln Gly Thr Arg
                325                 330                 335

Asn Gln Ala Ala Ala
            340
```

<210> SEQ ID NO 32
<211> LENGTH: 1026
<212> TYPE: DNA
<213> ORGANISM: Pseudomonas syringae -continued

<400> SEQUENCE: 32
atgcagagtc tcagtcttaa cagcagctcg ctgcaaaccc cggcaatggc ccttgtcctg 60
gtacgtcctg aagccgagac gactggcagt acgtcgagca aggcgcttca ggaagttgtc 120
gtgaagctgg ccgaggaact gatgcgcaat ggtcaactcg acgacagctc gccattggga 180
aaactgttgg ccaagtcgat ggccgcagat ggcaaggcgg gcggcggtat tgaggatgtc 240
atcgctgcgc tggacaagct gatccatgaa aagctcggtg acaacttcgg cgcgtctgcg 300
gacagcgcct cgggtaccgg acagcaggac ctgatgactc aggtgctcaa tggcctggcc 360
aagtcgatgc tcgatgatct tctgaccaag caggatggcg ggacaagctt ctccgaagac 420
gatatgccga tgctgaacaa gatcgcgcag ttcatggatg acaatcccgc acagtttccc 480
aagccggact cgggctcctg ggtgaacgaa ctcaaggaag acaacttcct tgatggcgac 540
gaaacggctg cgttccgttc ggcactcgac atcattggcc agcaactggg taatcagcag 600
agtgacgctg gcagtctggc agggacgggt ggaggtctgg gcactccgag cagtttttcc 660
aacaactcgt ccgtgatggg tgatccgctg atcgacgcca ataccggtcc cggtgacagc 720
ggcaataccc gtggtgaagc ggggcaactg atcggcgagc ttatcgaccg tggcctgcaa 780
tcggtattgg ccggtggtgg actgggcaca cccgtaaaca ccccgcagac cggtacgtcg 840
gcgaatggcg gacagtccgc tcaggatctt gatcagttgc tgggcggctt gctgctcaag 900
ggcctggagg caacgctcaa ggatgccggg caaacaggca ccgacgtgca gtcgagcgct 960
gcgcaaatcg ccaccttgct ggtcagtacg ctgctgcaag gcacccgcaa tcaggctgca 1020
gcctga 1026

<210> SEQ ID NO 33
<211> LENGTH: 1729
<212> TYPE: DNA
<213> ORGANISM: Pseudomonas syringae

<400> SEQUENCE: 33
tccacttcgc tgattttgaa attggcagat tcatagaaac gttcaggtgt ggaaatcagg 60
ctgagtgcgc agatttcgtt gataagggtg tggtactggt cattgttggt catttcaagg 120
cctctgagtg cggtgcggag caataccagt cttcctgctg gcgtgtgcac actgagtcgc 180
aggcataggc atttcagttc cttgcgttgg ttgggcatat aaaaaaagga acttttaaaa 240
acagtgcaat gagatgccgg caaaacggga accggtcgct gcgctttgcc actcacttcg 300
agcaagctca accccaaaca tccacatccc tatcgaacgg acagcgatac ggccacttgc 360
tctggtaaac cctggagctg gcgtcggtcc aattgcccac ttagcgaggt aacgcagcat 420
gagcatcggc atcacacccc ggccgcaaca gaccaccacg ccactcgatt tttcggcgct 480
aagcggcaag agtcctcaac caaacacgtt cggcgagcag aacactcagc aagcgatcga 540
cccgagtgca ctgttgttcg gcagcgacac acagaaagac gtcaacttcg gcacgcccga 600
cagcaccgtc cagaatccgc aggacgccag caagcccaac gacagccagt ccaacatcgc 660
taaattgatc agtgcattga tcatgtcgtt gctgcagatg ctcaccaact ccaataaaaa 720
gcaggacacc aatcaggaac agcctgatag ccaggctcct ttccagaaca acggcgggct 780
cggtacaccg tcggccgata gcgggggcgg cggtacaccg gatgcgacag gtggcggcgg 840
cggtgatacg ccaagcgcaa caggcggtgg cggcggtgat actccgaccg caacaggcgg 900
tggcggcagc ggtggcggcg gcacacccac tgcaacaggt ggcggcagcg gtggcacacc 960

-continued

```
cactgcaaca ggcggtggcg agggtggcgt aacaccgcaa atcactccgc agttggccaa   1020

ccctaaccgt acctcaggta ctggctcggt gtcggacacc gcaggttcta ccgagcaagc   1080

cggcaagatc aatgtggtga aagacaccat caaggtcggc gctggcgaag tctttgacgg   1140

ccacggcgca accttcactg ccgacaaatc tatgggtaac ggagaccagg gcgaaaatca   1200

gaagcccatg ttcgagctgg ctgaaggcgc tacgttgaag aatgtgaacc tgggtgagaa   1260

cgaggtcgat ggcatccacg tgaaagccaa aaacgctcag gaagtcacca ttgacaacgt   1320

gcatgcccag aacgtcggtg aagacctgat tacggtcaaa ggcgagggag gcgcagcggt   1380

cactaatctg aacatcaaga acagcagtgc caaaggtgca gacgacaagg ttgtccagct   1440

caacgccaac actcacttga aaatcgacaa cttcaaggcc gacgatttcg gcacgatggt   1500

tcgcaccaac ggtggcaagc agtttgatga catgagcatc gagctgaacg gcatcgaagc   1560

taaccacggc aagttcgccc tggtgaaaag cgacagtgac gatctgaagc tggcaacggg   1620

caacatcgcc atgaccgacg tcaaacacgc ctacgataaa acccaggcat cgacccaaca   1680

caccgagctt tgaatccaga caagtagctt gaaaaaaggg ggtggactc              1729
```

```
<210> SEQ ID NO 34
<211> LENGTH: 424
<212> TYPE: PRT
<213> ORGANISM: Pseudomonas syringae

<400> SEQUENCE: 34

Met Ser Ile Gly Ile Thr Pro Arg Pro Gln Gln Thr Thr Thr Pro Leu
  1               5                  10                  15

Asp Phe Ser Ala Leu Ser Gly Lys Ser Pro Gln Pro Asn Thr Phe Gly
             20                  25                  30

Glu Gln Asn Thr Gln Gln Ala Ile Asp Pro Ser Ala Leu Leu Phe Gly
         35                  40                  45

Ser Asp Thr Gln Lys Asp Val Asn Phe Gly Thr Pro Asp Ser Thr Val
     50                  55                  60

Gln Asn Pro Gln Asp Ala Ser Lys Pro Asn Asp Ser Gln Ser Asn Ile
 65                  70                  75                  80

Ala Lys Leu Ile Ser Ala Leu Ile Met Ser Leu Leu Gln Met Leu Thr
                 85                  90                  95

Asn Ser Asn Lys Lys Gln Asp Thr Asn Gln Glu Gln Pro Asp Ser Gln
            100                 105                 110

Ala Pro Phe Gln Asn Asn Gly Gly Leu Gly Thr Pro Ser Ala Asp Ser
        115                 120                 125

Gly Gly Gly Gly Thr Pro Asp Ala Thr Gly Gly Gly Gly Gly Asp Thr
    130                 135                 140

Pro Ser Ala Thr Gly Gly Gly Gly Gly Asp Thr Pro Thr Ala Thr Gly
145                 150                 155                 160

Gly Gly Gly Ser Gly Gly Gly Gly Thr Pro Thr Ala Thr Gly Gly Gly
                165                 170                 175

Ser Gly Gly Thr Pro Thr Ala Thr Gly Gly Gly Glu Gly Gly Val Thr
            180                 185                 190

Pro Gln Ile Thr Pro Gln Leu Ala Asn Pro Asn Arg Thr Ser Gly Thr
        195                 200                 205

Gly Ser Val Ser Asp Thr Ala Gly Ser Thr Glu Gln Ala Gly Lys Ile
    210                 215                 220

Asn Val Val Lys Asp Thr Ile Lys Val Gly Ala Gly Glu Val Phe Asp
225                 230                 235                 240
```

-continued

```
Gly His Gly Ala Thr Phe Thr Ala Asp Lys Ser Met Gly Asn Gly Asp
                245                 250                 255

Gln Gly Glu Asn Gln Lys Pro Met Phe Glu Leu Ala Glu Gly Ala Thr
            260                 265                 270

Leu Lys Asn Val Asn Leu Gly Glu Asn Glu Val Asp Gly Ile His Val
        275                 280                 285

Lys Ala Lys Asn Ala Gln Glu Val Thr Ile Asp Asn Val His Ala Gln
    290                 295                 300

Asn Val Gly Glu Asp Leu Ile Thr Val Lys Gly Glu Gly Gly Ala Ala
305                 310                 315                 320

Val Thr Asn Leu Asn Ile Lys Asn Ser Ser Ala Lys Gly Ala Asp Asp
                325                 330                 335

Lys Val Val Gln Leu Asn Ala Asn Thr His Leu Lys Ile Asp Asn Phe
            340                 345                 350

Lys Ala Asp Asp Phe Gly Thr Met Val Arg Thr Asn Gly Gly Lys Gln
        355                 360                 365

Phe Asp Asp Met Ser Ile Glu Leu Asn Gly Ile Glu Ala Asn His Gly
    370                 375                 380

Lys Phe Ala Leu Val Lys Ser Asp Ser Asp Asp Leu Lys Leu Ala Thr
385                 390                 395                 400

Gly Asn Ile Ala Met Thr Asp Val Lys His Ala Tyr Asp Lys Thr Gln
                405                 410                 415

Ala Ser Thr Gln His Thr Glu Leu
            420


<210> SEQ ID NO 35
<211> LENGTH: 344
<212> TYPE: PRT
<213> ORGANISM: Pseudomonas solanacearum
<220> FEATURE:
<223> OTHER INFORMATION: Description of Unknown Organism:  Pseudomonas
      solanacearum

<400> SEQUENCE: 35

Met Ser Val Gly Asn Ile Gln Ser Pro Ser Asn Leu Pro Gly Leu Gln
  1               5                  10                  15

Asn Leu Asn Leu Asn Thr Asn Thr Asn Ser Gln Gln Ser Gly Gln Ser
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly Asn Thr Gly
     50                  55                  60

Asn Thr Gly Asn Ala Pro Ala Lys Asp Gly Asn Ala Asn Ala Gly Ala
 65                  70                  75                  80

Asn Asp Pro Ser Lys Asn Asp Pro Ser Lys Ser Gln Ala Pro Gln Ser
                 85                  90                  95

Ala Asn Lys Thr Gly Asn Val Asp Asp Ala Asn Asn Gln Asp Pro Met
            100                 105                 110

Gln Ala Leu Met Gln Leu Leu Glu Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gly Gln Gly Gly Leu Ala
145                 150                 155                 160

Glu Ala Leu Gln Glu Ile Glu Gln Ile Leu Ala Gln Leu Gly Gly Gly
                165                 170                 175
```

-continued

```
Gly Ala Gly Ala Gly Gly Ala Gly Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205

Asp Gly Gly Asn Gly Val Asn Gly Asn Gln Ala Asn Gly Pro Gln Asn
    210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
                245                 250                 255

Ala Leu Val Gln Met Met Gln Gln Gly Gly Leu Gly Gly Gly Asn Gln
            260                 265                 270

Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
    290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
                325                 330                 335

Gln Ser Thr Ser Thr Gln Pro Met
            340
```

<210> SEQ ID NO 36
<211> LENGTH: 1035
<212> TYPE: DNA
<213> ORGANISM: Pseudomonas solanacearum

<400> SEQUENCE: 36

```
atgtcagtcg gaaacatcca gagcccgtcg aacctcccgg gtctgcagaa cctgaacctc      60

aacaccaaca ccaacagcca gcaatcgggc cagtccgtgc aagacctgat caagcaggtc     120

gagaaggaca tcctcaacat catcgcagcc ctcgtgcaga aggccgcaca gtcggcgggc     180

ggcaacaccg gtaacaccgg caacgcgccg gcgaaggacg gcaatgccaa cgcgggcgcc     240

aacgacccga gcaagaacga cccgagcaag agccaggctc cgcagtcggc caacaagacc     300

ggcaacgtcg acgacgccaa caaccaggat ccgatgcaag cgctgatgca gctgctggaa     360

gacctggtga agctgctgaa ggcggccctg cacatgcagc agcccggcgg caatgacaag     420

ggcaacggcg tgggcggtgc caacggcgcc aagggtgccg gcggccaggg cggcctggcc     480

gaagcgctgc aggagatcga gcagatcctc gcccagctcg gcggcggcgg tgctggcgcc     540

ggcggcgcgg gtggcggtgt cggcggtgct ggtggcgcgg atggcggctc cggtgcgggt     600

ggcgcaggcg gtgcgaacgg cgccgacggc ggcaatggcg tgaacggcaa ccaggcgaac     660

ggcccgcaga acgcaggcga tgtcaacggt gccaacggcg cggatgacgg cagcgaagac     720

cagggcggcc tcaccggcgt gctgcaaaag ctgatgaaga tcctgaacgc gctggtgcag     780

atgatgcagc aaggcggcct cggcggcggc aaccaggcgc agggcggctc gaagggtgcc     840

ggcaacgcct cgccggcttc cggcgcgaac ccgggcgcga accagcccgg ttcggcggat     900

gatcaatcgt ccggccagaa caatctgcaa tcccagatca tggatgtggt gaaggaggtc     960

gtccagatcc tgcagcagat gctggcggcg cagaacggcg gcagccagca gtccacctcg    1020

acgcagccga tgtaa                                                     1035
```

-continued

```
<210> SEQ ID NO 37
<211> LENGTH: 26
<212> TYPE: PRT
<213> ORGANISM: Xanthomonas campestris pv. glycines

<400> SEQUENCE: 37

Thr Leu Ile Glu Leu Met Ile Val Val Ala Ile Ile Ala Ile Leu Ala
  1               5                  10                  15

Ala Ile Ala Leu Pro Ala Tyr Gln Asp Tyr
             20                  25


<210> SEQ ID NO 38
<211> LENGTH: 20
<212> TYPE: PRT
<213> ORGANISM: Xanthomonas campestris pv. pelargonii

<400> SEQUENCE: 38

Ser Ser Gln Gln Ser Pro Ser Ala Gly Ser Glu Gln Gln Leu Asp Gln
  1               5                  10                  15

Leu Leu Ala Met
             20


<210> SEQ ID NO 39
<211> LENGTH: 13
<212> TYPE: PRT
<213> ORGANISM: Phytophthora megasperma

<400> SEQUENCE: 39

Val Trp Asn Gln Pro Val Arg Gly Phe Lys Val Tyr Glu
  1               5                  10
```